(12) United States Patent
Fitzgerald et al.

(10) Patent No.: US 10,828,412 B2
(45) Date of Patent: Nov. 10, 2020

(54) SYSTEMS AND METHODS FOR PERITONEAL DIALYSIS HAVING POINT OF USE DIALYSIS FLUID PREPARATION INCLUDING MIXING AND HEATING THEREFORE

(71) Applicant: GAMBRO LUNDIA AB, Lund (SE)

(72) Inventors: Jane E. Fitzgerald, Chicago, IL (US); Ryan P. Marry, Gurnee, IL (US); John S. Norman, Gurnee, IL (US); James D. Ascenzo, Glen Ellyn, IL (US); Meng-Yang Chen, Chicago, IL (US); Anders Wellings, Belleair Beach, FL (US); Edward S. Szpara, St. Charles, IL (US); Olof Jansson, Vellinge (SE)

(73) Assignee: Gambro Lundia AB, Lund (SE)

( * ) Notice: Subject to any disclaimer, the term of this patent is extended or adjusted under 35 U.S.C. 154(b) by 516 days.

(21) Appl. No.: 15/588,454

(22) Filed: May 5, 2017

(65) Prior Publication Data
US 2017/0319770 A1    Nov. 9, 2017

Related U.S. Application Data

(60) Provisional application No. 62/332,617, filed on May 6, 2016, provisional application No. 62/332,623, filed
(Continued)

(51) Int. Cl.
*A61M 1/28* (2006.01)
*A61M 1/16* (2006.01)
(Continued)

(52) U.S. Cl.
CPC .......... *A61M 1/287* (2013.01); *A61M 1/1605* (2014.02); *A61M 1/166* (2014.02);
(Continued)

(58) Field of Classification Search
CPC .............. A61M 1/166; A61M 2205/36; A61M 2205/3368; A61M 1/287
See application file for complete search history.

(56) References Cited

U.S. PATENT DOCUMENTS

| 3,563,381 A | 2/1971 | Edelson et al. |
| 3,685,680 A | 8/1972 | Tenckhoff et al. |

(Continued)

FOREIGN PATENT DOCUMENTS

| EP | 0171550 A1 | 2/1986 |
| EP | 0749328 A1 | 12/1996 |

(Continued)

OTHER PUBLICATIONS

International Search Report for corresponding International Application PCT/US2009/031809 dated Oct. 19, 2009.
(Continued)

*Primary Examiner* — Bradley J Osinski
(74) *Attorney, Agent, or Firm* — K&L Gates LLP

(57) ABSTRACT

A peritoneal dialysis system includes a cycler including a pump actuator, a heater and a heating pan operable with the heater, and a disposable set operable with the cycler. The heating pan includes a sidewall forming a slot. The disposable set includes a pumping cassette and a heater/mixing container. The pumping cassette includes a pump chamber configured to be actuated by the pump actuator. Additionally, the heater/mixing container is in fluid communication with the pumping cassette and is sized to be received at the heating pan. The heater/mixing container includes a port configured such that when the port is slid into the slot of the heater pan sidewall, the port is prevented from rotating about an axis transverse to a direction of flow through the port.

8 Claims, 29 Drawing Sheets

Related U.S. Application Data on May 6, 2016, provisional application No. 62/332,630, filed on May 6, 2016.

(51) Int. Cl.
*C02F 1/00* (2006.01)
*C02F 1/44* (2006.01)
*C02F 103/02* (2006.01)

(52) U.S. Cl.
CPC ........ *A61M 1/1656* (2013.01); *A61M 1/1666* (2014.02); *A61M 1/28* (2013.01); *A61M 1/281* (2014.02); *A61M 1/282* (2014.02); *A61M 1/284* (2014.02); *C02F 1/008* (2013.01); *C02F 1/444* (2013.01); *A61M 2205/12* (2013.01); *A61M 2205/18* (2013.01); *A61M 2205/3317* (2013.01); *A61M 2205/3331* (2013.01); *A61M 2205/3337* (2013.01); *A61M 2205/3368* (2013.01); *A61M 2205/3569* (2013.01); *A61M 2205/36* (2013.01); *A61M 2205/3653* (2013.01); *A61M 2205/50* (2013.01); *A61M 2205/502* (2013.01); *A61M 2205/6054* (2013.01); *A61M 2205/6072* (2013.01); *A61M 2205/702* (2013.01); *A61M 2205/705* (2013.01); *A61M 2205/75* (2013.01); *A61M 2205/7518* (2013.01); *C02F 2103/026* (2013.01); *C02F 2209/03* (2013.01); *C02F 2209/40* (2013.01)

(56) References Cited

U.S. PATENT DOCUMENTS

| | | | |
|---|---|---|---|
| 3,744,636 A | 7/1973 | Commarmot |
| 3,814,249 A | 6/1974 | Eaton |
| 3,878,095 A | 4/1975 | Frasier et al. |
| 3,915,802 A | 10/1975 | Kominek |
| 4,060,485 A | 11/1977 | Eaton |
| 4,067,803 A | 1/1978 | Quentin |
| 4,209,402 A | 6/1980 | Gentles |
| 4,348,280 A | 9/1982 | George et al. |
| 4,360,323 A | 11/1982 | Anderson |
| 4,655,941 A | 4/1987 | Suzuki |
| 4,664,891 A | 5/1987 | Cosentino et al. |
| 4,734,198 A | 3/1988 | Harm et al. |
| 4,955,508 A | 9/1990 | Capanna et al. |
| 4,976,683 A | 12/1990 | Gauthier et al. |
| 5,032,265 A | 7/1991 | Jha et al. |
| 5,122,516 A | 6/1992 | Watanabe et al. |
| 5,236,476 A | 8/1993 | Klick |
| 5,256,371 A | 10/1993 | Pippert |
| 5,259,954 A | 11/1993 | Taylor |
| 5,274,434 A | 12/1993 | Morioka et al. |
| 5,295,505 A | 3/1994 | Polaschegg et al. |
| 5,318,750 A | 6/1994 | Lascombes |
| 5,326,473 A | 7/1994 | Lascombes et al. |
| 5,385,564 A | 1/1995 | Slater et al. |
| 5,498,338 A | 3/1996 | Kruger et al. |
| 5,540,842 A | 7/1996 | Aoyama et al. |
| 5,591,344 A | 1/1997 | Kenley et al. |
| 5,616,248 A | 4/1997 | Schal |
| 5,658,456 A | 8/1997 | Kenley et al. |
| 5,866,880 A | 2/1999 | Seitz et al. |
| 5,895,578 A | 4/1999 | Simard et al. |
| 5,906,978 A | 5/1999 | Ash |
| 5,945,449 A | 8/1999 | Purcell et al. |
| 5,948,251 A | 9/1999 | Brugger |
| 5,954,958 A | 9/1999 | Folden |
| 6,146,536 A | 11/2000 | Twardowski |
| 6,210,803 B1 | 4/2001 | Backhaus et al. |
| 6,228,047 B1 | 5/2001 | Dadson |
| 6,251,279 B1 | 6/2001 | Peterson et al. |
| 6,254,567 B1 | 7/2001 | Tau et al. |
| 6,274,103 B1 | 8/2001 | Taylor |
| 6,277,815 B1 | 8/2001 | Knerr |
| 6,280,634 B1 | 8/2001 | Shah et al. |
| 6,348,162 B1 | 2/2002 | Ash |
| 6,361,201 B1 | 3/2002 | Russell et al. |
| 6,364,143 B1 | 4/2002 | Knierbein |
| 6,419,825 B1 | 7/2002 | Hahmann et al. |
| 6,426,056 B2 | 7/2002 | Taylor |
| 6,429,294 B1 | 8/2002 | Masuda et al. |
| 6,464,977 B2 | 10/2002 | Kai et al. |
| 6,485,479 B1 | 11/2002 | Knierbein |
| 6,489,301 B1 | 12/2002 | Kobira et al. |
| 6,572,641 B2 | 6/2003 | Brugger et al. |
| 6,582,385 B2 | 6/2003 | Burbank et al. |
| 6,595,944 B2 | 7/2003 | Balschat et al. |
| 6,623,709 B2 | 9/2003 | Taylor |
| 6,635,179 B1 | 10/2003 | Summerton et al. |
| 6,645,191 B1 | 11/2003 | Knerr et al. |
| 6,656,355 B2 | 12/2003 | Sano |
| 6,673,376 B1 | 1/2004 | Knerr et al. |
| 6,685,831 B2 | 2/2004 | Donig et al. |
| 6,689,393 B1 | 2/2004 | Knerr |
| 6,745,903 B2 | 6/2004 | Grandics |
| 6,749,818 B2 | 6/2004 | Sano et al. |
| 6,752,928 B2 | 6/2004 | Pfeil et al. |
| 6,758,975 B2 | 7/2004 | Peabody et al. |
| 6,787,032 B2 | 9/2004 | Kurome et al. |
| 6,796,971 B2 | 9/2004 | Anderson et al. |
| 6,814,869 B2 | 11/2004 | Brandl et al. |
| 6,861,033 B2 | 3/2005 | Mullins et al. |
| 6,890,157 B2 | 5/2005 | Pfeil et al. |
| 6,902,670 B2 | 6/2005 | Ho |
| 6,908,546 B2 | 6/2005 | Smith |
| 6,923,987 B2 | 8/2005 | Kai et al. |
| 6,986,872 B2 | 1/2006 | Taylor |
| 7,029,456 B2 | 4/2006 | Ware et al. |
| 7,045,061 B2 | 5/2006 | Nishimura et al. |
| 7,077,956 B2 | 7/2006 | Rovatti |
| 7,108,790 B2 | 9/2006 | Collins et al. |
| 7,208,092 B2 | 4/2007 | Micheli |
| 7,250,619 B2 | 7/2007 | Taylor et al. |
| 7,290,680 B2 | 11/2007 | Henry et al. |
| 7,300,674 B2 | 11/2007 | Tobe |
| 7,311,886 B2 | 12/2007 | Dumont D'Ayot et al. |
| 7,345,029 B2 | 3/2008 | Zimmeck |
| 7,419,587 B2 | 9/2008 | Vaibjoern et al. |
| 7,419,597 B2 | 9/2008 | Brugger et al. |
| 7,544,300 B2 | 6/2009 | Brugger et al. |
| 7,550,446 B2 | 6/2009 | Henning |
| 7,563,244 B2 | 7/2009 | Kent et al. |
| 7,699,806 B2 | 4/2010 | Ware et al. |
| 7,749,393 B2 | 7/2010 | Brugger et al. |
| 7,758,082 B2 | 7/2010 | Weigel et al. |
| 7,790,043 B2 | 9/2010 | Brugger et al. |
| 7,798,997 B2 | 9/2010 | Kamen et al. |
| 7,828,786 B2 | 11/2010 | Ramella |
| 7,837,666 B2 | 11/2010 | Jensen et al. |
| 7,857,802 B2 | 12/2010 | Brandenburger et al. |
| 7,875,015 B2 | 1/2011 | Pahlberg et al. |
| 7,875,016 B2 | 1/2011 | Paulberg et al. |
| 7,892,423 B2 | 2/2011 | Rohde et al. |
| 7,976,711 B2 | 7/2011 | Bragger et al. |
| 7,985,212 B2 | 7/2011 | Jensen et al. |
| 8,052,631 B2 | 8/2011 | Jensen et al. |
| 8,071,055 B2 | 12/2011 | Newcombe |
| 8,128,611 B2 | 3/2012 | Watts et al. |
| 8,162,915 B2 | 4/2012 | Brandenburger et al. |
| 8,177,977 B2 | 5/2012 | Gaignet |
| 8,192,387 B2 | 6/2012 | Brugger et al. |
| 8,202,420 B2 | 6/2012 | Brugger et al. |
| 8,216,452 B2 | 7/2012 | Rohde et al. |
| 8,246,826 B2 | 8/2012 | Wilt et al. |
| 8,251,971 B2 | 8/2012 | Graf et al. |
| 8,317,750 B2 | 11/2012 | Ware et al. |
| 8,328,784 B2 | 12/2012 | Jensen et al. |
| 8,354,029 B2 | 1/2013 | Hank |
| 8,357,298 B2 | 1/2013 | Demers et al. |
| 8,409,441 B2 | 4/2013 | Wilt et al. |
| 8,409,445 B2 | 4/2013 | Levin et al. |

(56) References Cited

U.S. PATENT DOCUMENTS

| | | |
|---|---|---|
| 8,425,767 B2 | 4/2013 | Fava et al. |
| 8,460,228 B2 | 6/2013 | Burbank et al. |
| 8,460,558 B2 | 6/2013 | Brugger et al. |
| 8,469,331 B2 | 6/2013 | Burbank et al. |
| 8,496,824 B2 | 7/2013 | Remkes et al. |
| 8,501,009 B2 | 8/2013 | Peterson et al. |
| 8,517,597 B2 | 8/2013 | Shreve |
| 8,524,086 B2 | 9/2013 | Peterson et al. |
| 8,529,766 B2 | 9/2013 | Minami et al. |
| 8,540,875 B2 | 9/2013 | Levin et al. |
| 8,545,428 B2 | 10/2013 | Burbank et al. |
| 8,585,681 B2 | 11/2013 | Boenig et al. |
| 8,585,907 B2 | 11/2013 | Raiford et al. |
| 8,597,223 B2 | 12/2013 | Dumon D'Ayot et al. |
| 8,617,134 B2 | 12/2013 | Brehm et al. |
| 8,617,393 B2 | 12/2013 | Remkes et al. |
| 8,622,986 B2 | 1/2014 | Ramella et al. |
| 8,671,996 B2 | 3/2014 | Weilhoefer et al. |
| 8,673,139 B2 | 3/2014 | Hedmann et al. |
| 8,678,224 B2 | 3/2014 | Dumont D'Ayot et al. |
| 8,679,348 B2 | 3/2014 | Burbank et al. |
| 8,685,251 B2 | 4/2014 | Smejtek et al. |
| 8,715,214 B2 | 5/2014 | Kopperschmidt |
| 8,758,626 B2 | 6/2014 | Wong |
| 8,771,749 B2 | 7/2014 | Oda et al. |
| 8,791,078 B2 | 7/2014 | Kirschner |
| 8,813,769 B2 | 8/2014 | Gastauer et al. |
| 8,821,719 B2 | 9/2014 | Becker |
| 8,870,811 B2 | 10/2014 | Gavin et al. |
| 8,882,737 B2 | 11/2014 | Grab et al. |
| 8,906,240 B2 | 12/2014 | Cmkovich et al. |
| 8,961,872 B2 | 2/2015 | Fehr et al. |
| 9,005,150 B2 | 4/2015 | Ware et al. |
| 9,011,765 B2 | 4/2015 | Rahn et al. |
| 9,022,765 B2 | 4/2015 | Rahn et al. |
| 9,084,855 B2 | 7/2015 | Ware et al. |
| 9,095,499 B2 | 8/2015 | Kugelmann et al. |
| 9,132,220 B2 | 9/2015 | Kugelmann et al. |
| 9,138,526 B2 | 9/2015 | Ware et al. |
| 9,155,824 B2 | 10/2015 | Eyrard et al. |
| 9,180,069 B2 | 11/2015 | Jensen et al. |
| 9,220,800 B2 | 12/2015 | Shenberg |
| 9,220,828 B2 | 12/2015 | Coates |
| 9,249,345 B2 | 2/2016 | Schweitzer et al. |
| 9,265,874 B2 | 2/2016 | Kloeffel |
| 9,274,073 B2 | 3/2016 | Nier et al. |
| 9,375,524 B2 | 6/2016 | Levin et a. |
| 9,388,059 B2 | 7/2016 | Burbank et al. |
| 9,399,069 B2 | 7/2016 | Nikolic et al. |
| 2003/0135250 A1 | 7/2003 | Lauman et al. |
| 2003/0220605 A1 | 11/2003 | Bowman et al. |
| 2005/0008505 A1 | 1/2005 | Capp et al. |
| 2007/0163965 A1 | 7/2007 | Wolfe |
| 2007/0237835 A1 | 10/2007 | Passlick-Deetjen et al. |
| 2007/0278155 A1 | 12/2007 | Lo et al. |
| 2008/0045877 A1 | 2/2008 | Levin et al. |
| 2008/0058697 A1* | 3/2008 | Kamen ............ F04B 43/0054 604/6.13 |
| 2008/0203023 A1 | 8/2008 | Burbank et al. |
| 2008/0210606 A1 | 9/2008 | Burbank |
| 2008/0230450 A1 | 9/2008 | Burbank et al. |
| 2009/0008318 A1 | 1/2009 | Anes et al. |
| 2009/0008331 A1 | 1/2009 | Wilt et al. |
| 2009/0012460 A1 | 1/2009 | Steck et al. |
| 2009/0012655 A1 | 1/2009 | Kienman et al. |
| 2009/0045121 A1 | 2/2009 | Kabayama et al. |
| 2009/0218285 A1 | 9/2009 | Hank |
| 2010/0018923 A1 | 1/2010 | Rohde et al. |
| 2010/0051546 A1 | 3/2010 | Vuong et al. |
| 2010/0078092 A1 | 4/2010 | Weilhoefer et al. |
| 2010/0137693 A1 | 6/2010 | Porras et al. |
| 2010/0326916 A1 | 12/2010 | Wrazel et al. |
| 2010/0332149 A1 | 12/2010 | Scholpp |
| 2011/0100913 A1 | 5/2011 | Minami et al. |
| 2011/0180480 A1 | 7/2011 | Kloeffel et al. |
| 2011/0186521 A1 | 8/2011 | Burbank et al. |
| 2011/0192796 A1 | 8/2011 | Smejtek et al. |
| 2011/0315611 A1 | 12/2011 | Fulkerson et al. |
| 2012/0074060 A1 | 3/2012 | Lass |
| 2012/0095392 A1 | 4/2012 | Jensen et al. |
| 2012/0138533 A1 | 6/2012 | Curtis et al. |
| 2012/0310150 A1 | 6/2012 | Brandl et al. |
| 2012/0199205 A1 | 8/2012 | Eyrard et al. |
| 2013/0004593 A1 | 1/2013 | Kloeffel et al. |
| 2013/0008854 A1 | 1/2013 | Wallace et al. |
| 2013/0020237 A1 | 1/2013 | Wilt et al. |
| 2013/0062265 A1 | 3/2013 | Balschat et al. |
| 2013/0105025 A1 | 5/2013 | Fehr et al. |
| 2013/0195717 A1 | 8/2013 | Fehr et al. |
| 2013/0228505 A1 | 9/2013 | Burbank et al. |
| 2013/0240441 A1 | 9/2013 | Terpin et al. |
| 2013/0333795 A1 | 12/2013 | Balschat et al. |
| 2014/0018727 A1 | 1/2014 | Burbank et al. |
| 2014/0034657 A1 | 2/2014 | Eyrard et al. |
| 2014/0076058 A1 | 3/2014 | Brugger et al. |
| 2014/0091022 A1 | 4/2014 | Raiford et al. |
| 2014/0144794 A1 | 5/2014 | Eyrard et al. |
| 2014/0191501 A1 | 7/2014 | Brugger et al. |
| 2014/0209520 A1 | 7/2014 | Koch et al. |
| 2014/0220699 A1 | 8/2014 | Pudil et al. |
| 2014/0224737 A1 | 8/2014 | Fichert et al. |
| 2014/0230923 A1 | 8/2014 | Brehm et al. |
| 2014/0238912 A1 | 8/2014 | Vincent |
| 2014/0316332 A1 | 10/2014 | Lo et al. |
| 2015/0005699 A1 | 1/2015 | Burbank et al. |
| 2015/0008183 A1 | 1/2015 | Cmkovich et al. |
| 2015/0041377 A1 | 2/2015 | Heyes |
| 2016/0038522 A1 | 2/2016 | Carlson et al. |
| 2016/0058933 A1 | 3/2016 | Ballantyne et al. |
| 2016/0101227 A1 | 4/2016 | Norris et al. |
| 2016/0213832 A1 | 7/2016 | Eyrard et al. |
| 2016/0340214 A1 | 11/2016 | Turk et al. |
| 2017/0001887 A1 | 1/2017 | Weigel et al. |
| 2017/0182237 A1 | 6/2017 | Burbank et al. |
| 2017/0203022 A1 | 7/2017 | Burbank et al. |
| 2017/0203024 A1 | 7/2017 | Burbank et al. |
| 2017/0203025 A1 | 7/2017 | Burbank et al. |
| 2017/0203026 A1 | 7/2017 | Burbank et al. |
| 2017/0203027 A1 | 7/2017 | Burbank et al. |

FOREIGN PATENT DOCUMENTS

| | | |
|---|---|---|
| EP | 1614437 | 1/2006 |
| EP | 2180908 | 5/2010 |
| EP | 2181965 | 5/2010 |
| EP | 2190552 | 6/2010 |
| EP | 1349632 | 2/2011 |
| EP | 1765254 | 2/2012 |
| EP | 2501357 | 4/2014 |
| EP | 2765971 | 8/2014 |
| EP | 2569028 | 9/2015 |
| EP | 2670373 | 2/2016 |
| EP | 2387422 | 10/2016 |
| WO | 1992018048 | 10/1992 |
| WO | 9625214 | 8/1996 |
| WO | 96/40318 | 12/1996 |
| WO | 9906082 | 2/1999 |
| WO | 2006005391 | 1/2006 |
| WO | 2008-138311 | 11/2008 |
| WO | 2008138311 | 11/2008 |
| WO | WO/2009/025545 | 2/2009 |
| WO | WO2010081672 | 7/2010 |
| WO | 2011/069110 | 6/2011 |
| WO | 2011101428 | 8/2011 |
| WO | 2011/141186 | 11/2011 |
| WO | WO/2012/104405 | 8/2012 |
| WO | 2013/055283 | 4/2013 |
| WO | 2013141896 | 9/2013 |

(56) References Cited

FOREIGN PATENT DOCUMENTS

| WO | 2013/173349 | 11/2013 |
|----|-------------|---------|
| WO | 2016057982  | 4/2016  |

OTHER PUBLICATIONS

Written Opinion for corresponding International Application PCT/US2009/031809 dated Oct. 19, 2009.
U.S. Appl. No. 60/903,582, filed Feb. 27, 2007.
U.S. Appl. No. 60/904,024, filed Feb. 27, 2007.
U.S. Appl. No. 61/092,239, filed Aug. 27, 2008.
U.S. Appl. No. 61/489,544, filed May 24, 2011.
U.S. Appl. No. 61/498,394, filed Jun. 17, 2011.
U.S. Appl. No. 62/003,374, filed May 27, 2014.
U.S. Appl. No. 62/004,567, filed May 29, 2014.
Search Report Issued in French application No. 1452117, dated Mar. 31, 2016, 2 pages.
Written Opinion Issued in French application No. 1452117, dated Mar. 31, 2016, 5 pages.
European Communication dated Mar. 20, 2015 for Application No. 09 710 209.9—1662, 6 pages.
Search and Examination Report dated Jul. 29, 2014 for related GB Appl. No. 1322331.8.
Office Action for Mexican Patent Application No. Mx/a/2010/008961 dated Jul. 1, 2013.
Manns et al., "The acu-menTM: A new device for continuous renal replacement therapy in acute renal failure", Kidney International, 1998, pp. 268-274, vol. 54.
European Search Report dated Mar. 21, 2017—Appl. 16176496.4—1664 (10 pages).
International Search Report and Written Opinion dated Sep. 26, 2017 issued in corresponding PCT Application No. PCT/US2017/031405.

\* cited by examiner

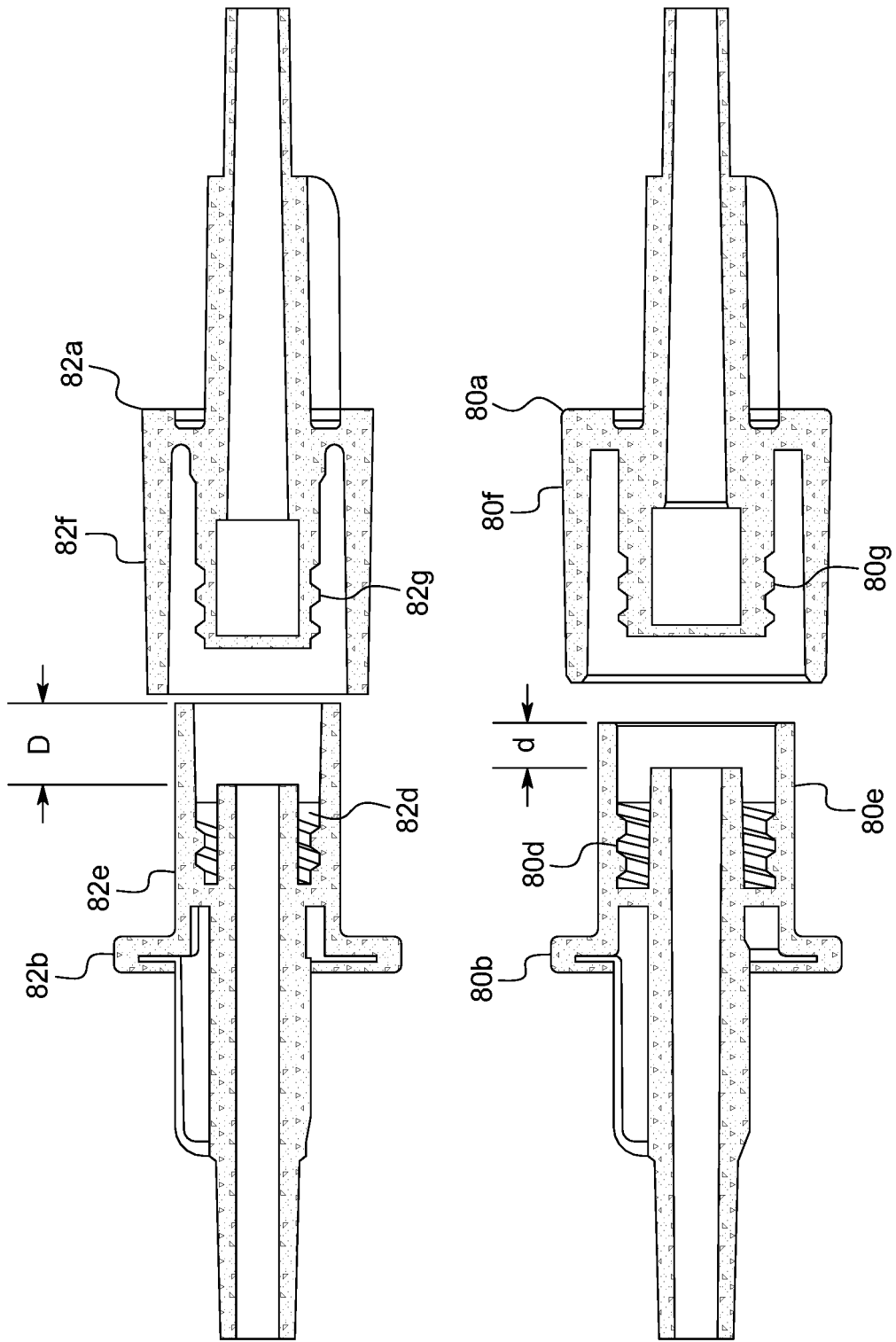

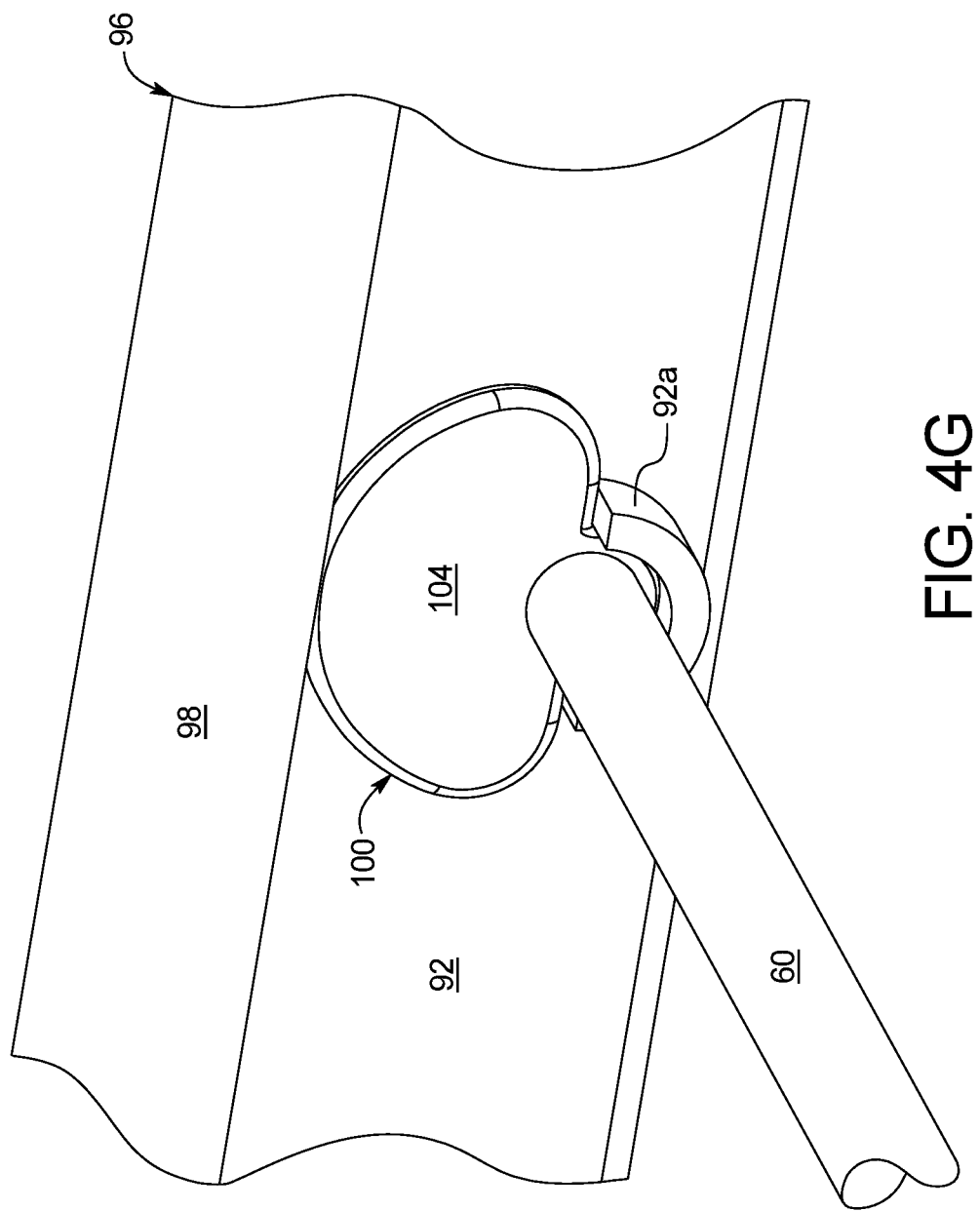

SYSTEMS AND METHODS FOR PERITONEAL DIALYSIS HAVING POINT OF USE DIALYSIS FLUID PREPARATION INCLUDING MIXING AND HEATING THEREFORE

PRIORITY

This application claims priority to and the benefit of U.S. Provisional Application Ser. No. 62/332,617, entitled, "Apparatus for Proportioning Fluids II", filed May 6, 2016; U.S. Provisional Application Ser. No. 62/332,623, entitled, "Apparatus for Proportioning Fluids II", filed May 6, 2016; and U.S. Provisional Application Ser. No. 62/332,630, entitled, "Apparatus for Proportioning Fluids III", filed May 6, 2016, the entire contents of each of which are incorporated herein by reference and relied upon.

BACKGROUND

The present invention relates to the field of fluid compounding for preparing fluids particularly for the treatment of renal insufficiency. More specifically, it relates to an apparatus for the treatment of renal insufficiency configured for compounding finished fluids from two or more constituent fluids for use as a kidney dialyzing fluid.

In particular, the invention may be used for preparing fluids for peritoneal dialysis, particularly for preparing fluids on-site (e.g. at patient's home).

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonate, phosphate, chloride) and the regulation of the acid/base equilibrium within the body, which is obtained in particular by the removal of weak acids (phosphates, monosodium acids) and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In the treatment of patients suffering acute or chronic renal insufficiency, dialysis therapy is employed. The two general categories of dialysis therapy are hemodialysis and peritoneal dialysis.

In hemodialysis, the patient's blood is cleansed by passage through an artificial kidney in an extracorporeal membrane system.

The blood treatment involves extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

In peritoneal dialysis, dialyzing fluid is infused into the patient's peritoneal cavity. This cavity is lined by the peritoneal membrane which is highly vascularized. The metabolites are removed from the patient's blood by diffusion across the peritoneal membrane into the dialyzing fluid. Excess fluid, i.e. water is also removed by osmosis induced by a hypertonic dialyzing fluid.

When an aqueous solution is instilled into the peritoneal cavity, the solute composition equilibrates with that of plasma water by passive diffusion along electrochemical concentration gradients. In addition the flux of fluid across the peritoneum in response to an osmotic agent moves solutes in the absence of a concentration gradient, leading to the concept that solute transport occurs partly by convection or 'solvent drag'. Removal of excess fluid is achieved by adding to the solution various concentrations of an osmotic agent (usually dextrose). Ultrafiltration continues until the dialysate becomes virtually isotonic, after which the rate that fluid is absorbed into the circulation exceeds that of the ultrafiltration induced by transcapillary hydrostatic pressure gradient alone. Net solute and water removal during peritoneal dialysis have been shown to be reduced by dialysate absorption. Through these two processes, diffusion and osmotic ultrafiltration, appropriate quantities of solute metabolites and fluid need to be removed to maintain the patient's body fluid volumes and composition within appropriate limits.

There are various types of peritoneal dialysis therapies, including continuous ambulatory peritoneal dialysis ("CAPD"), automated peritoneal dialysis ("APD"), including tidal flow APD, and continuous flow peritoneal dialysis ("CFPD").

CAPD is a manual dialysis treatment. The patient connects manually an implanted catheter to a drain, allowing spent dialysate fluid to drain from the peritoneal cavity. The patient then connects the catheter to a bag of fresh dialyzing fluid, infusing fresh dialyzing fluid through the catheter and into the patient. The patient disconnects the catheter from the fresh dialyzing fluid bag and allows the dialyzing fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialyzing fluid and to a fluid drain. APD machines pump fresh dialyzing fluid from the dialyzing fluid source, through the catheter, into the patient's peritoneal cavity and allow the dialyzing fluid to dwell within the cavity and the transfer of waste, toxins and excess water to take place. APD machines pump spent dialysate from the peritoneal cavity, through the catheter, to the drain. As with the manual process, several drain, fill and dwell cycles occur during APD. A "last fill" occurs often at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all the fluid from the patient over a longer period of time, a portion of the fluid is removed and replaced after smaller increments of time.

Continuous flow or CFPD systems clean or regenerate spent dialysate instead of discarding it. The systems flow fluid into or out of the patient, through a loop. Dialyzing fluid flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialyzing fluid into the peritoneal cavity. CFPD systems are more complicated typically than batch systems.

CAPD, APD (including tidal flow) and CFPD systems can employ a pumping cassette. The pumping cassette typically includes a flexible membrane that is moved mechanically to push and pull dialysis fluid out of and into, respectively, the cassette.

Peritoneal dialysis requires the maintenance of aseptic technique for connection because of the high risk of peritoneal infection. The risk of infection is particularly high due to the high number of exchanges of dialyzing fluid which the patient is exposed to.

In one form of peritoneal dialysis, an automated cycler is used to infuse and drain dialyzing fluid. This form of treatment may be done automatically at night while the patient sleeps The cycler measures the amount of fluid infused and the amount removed to compute the net fluid removal. The treatment sequence usually begins with an initial drain cycle to empty the peritoneal cavity of spent dialysate. The cycler then performs a series of fill, dwell, and drain cycles, typically finishing with a fill cycle.

Peritoneal dialysis generally requires large volumes of dialyzing fluid. Generally, at each application, or exchange, a given patient will infuse 2 to 3 liters of dialyzing fluid into the peritoneal cavity. The fluid is allowed to dwell for approximately 1 to 3 hours, at which time it is drained out and exchanged for fresh fluid. Generally, four such exchanges are performed daily. Therefore, approximately 8 to 20 liters of dialyzing fluid is required per day, 7 days a week, 365 days a year for each patient.

Dialyzing fluids have traditionally been provided in sealed, heat sterilized form, ready for use. Peritoneal dialysis is typically performed using bags with three different concentration of dextrose. The bags are being delivered to a patient's home as 1 liter to 6 liter bags with different dextrose concentrations and a normal daily consumption is around 8 to 20 liters of fluid.

In light of above, several problems become apparent. Shipping and storage of the sheer volume of fluids required is space consuming. Additionally, the use of multiple pre-filled bags produces waste materials in the form of empty containers and packaging.

An improved peritoneal dialysis system is needed accordingly.

SUMMARY

The present disclosure sets forth sub-systems, methods and structures for an overall peritoneal dialysis ("PD") system that creates dialysis solution at the point of use, e.g., at the PD machine. PD fluid is delivered directly to the patient's peritoneal cavity. PD fluid therefore needs to have a level of sterilization suitable for being introduced into the patient's peritoneum. PD dialysis fluid is accordingly pre-mixed and sterilized typically prior to delivery to the location of use, usually the patient's home.

A typical daily patient consumption of PD dialysis fluid is eight to twenty liters. The fluid is provided in sterilized bags of sizes up to six liters, which are packed into boxes and delivered, e.g., monthly, for use to the patient's home. The boxes of fluid may be cumbersome and heavy for PD patients to handle, and consume a substantial area in a room of their homes. The bags and boxes also produce a relatively large amount of waste disposed of on a weekly or monthly basis. The present PD system reduces significantly both the amount of dialysis solution stored and handled by PD patients and the amount of waste produced.

The overall system in an embodiment includes three primary components, namely, a PD cycler, a water purifier and a disposable set operating with both the cycler and the water purifier. The PD cycler may for example be an Amia® or HomeChoice® cycler marketed by Baxter International Inc. The disposable set in an embodiment includes a disposable cassette operated by the cycler and various tubes and connectors attached to the cassette. As described in detail below, the disposable set in an embodiment also includes a heating/mixing container and a water for peritoneal dialysis ("WFPD") accumulation container. The disposable set additionally includes at least one, and in one preferred embodiment two, concentrate containers that hold ingredients needed to prepare fresh dialysis fluid for treatment. In an embodiment, one of the concentrate containers holds a glucose solution, while the other concentrate container holds a buffer solution. Concentrate lines extend from the cassette and the concentrate containers and are mated together via concentrate connectors. In one embodiment, the concentrate connectors for the first concentrate, e.g., glucose, are physically different than the concentrate connectors for the second concentrate, e.g., buffer, so that the patient or user cannot connect the concentrate container line for the first concentrate to the cassette line for the second concentrate, and vice versa.

The disposable set in various embodiments also includes at least one, and in one embodiment two sterile sterilizing grade filters placed in series with each other. The sterile sterilizing grade filters may be pass-through filters with pores having average diameters suitable to produce sterile fluid, e.g., 0.22 micron, including the capability of removing endotoxins, resulting in water quality suitable for PD. The sterile sterilizing grade filters provide the final stage of sterilization for the water that is used to mix with the one or more concentrate to provide a dialysis fluid suitable for PD.

The overall system includes a water purifier and multiple components leading to the water purifier. The multiple components include, for example, a water softener, a particulate pre-filter, a carbon filter, an ion-exchange resin cartridge and a regenerating salts cartridge. The components are located between the water purifier and a source of potable or drinkable water. A bacterial growth inhibiting agent container may also be fluidly connected to the water purifier. The water purifier itself includes water purification equipment, such as one or more reverse osmosis unit, an electrodionization unit (optional), one or more pump to move water within the water purifier and one or more heater to heat the water within the water purifier. The water purifier also includes at least one reservoir for holding a quantity of water to be purified and for mixing with an anti-bacterial growth agent if provided. The water purifier may also include a deaerator for removing air from the water being purified. The water purifier may further include or operate with pretreatment equipment, e.g., a water softener module, connected to the patient's pottable water supply.

The water purifier may in an alternative embodiment include one or more ultrafilter to help bring the water exiting the water purifier to a WFPD level. For example, multiple ultrafilters may be provided to bring the water exiting the water purifier to a WFPD quality level, wherein the sterile sterilizing grade filters discussed above for the disposable set are not needed and accordingly not provided. In another embodiment, the water purifier includes a single ultrafilter, while the disposable set includes a single sterilizing filter, the combination of which brings the water to a level of sterilization suitable for being delivered to the patient's peritoneal cavity. In the embodiment in which the disposable set includes two or more sterile sterilizing grade filters, no ultrafilters are needed in the water purifier. For redundancy, however, it is contemplated to provide one or more ultrafilter in the water purifier in combination with one or more sterile sterilizing grade filters in the disposable set.

It is also contemplated for the cycler to command the water purifier to provide WFPD at a heated temperature. PD is performed with the dialysis fluid heated to body temperature or 35° C. to 37° C. It is accordingly contemplated to ask the water purifier to deliver water at some elevated temperature below 35° C. to 37° C., such as 10° C. to 40° C., more particularly in one embodiment 20° C. to 25° C., reducing the heating burden and heating time at the cycler.

The PD cycler is in one embodiment configured to operate the cassette of the disposable set pneumatically. Here, the PD cycler may include one or more positive pressure tank and one or more negative pressure tank. Electrically actuated solenoid valves are located between the pressure tanks and the disposable cassette. A control unit of the PD cycler electrically controls the solenoid valves to selectively allow positive or negative pneumatic pressure to reach the valves and pump chambers of the disposable cassette. Positive pressure is applied to close a valve of the cassette or to perform a pump-out or expel stroke at a pump chamber of the cassette. Negative pressure on the other hand is applied to open a valve of the cassette or to perform a pump-in or fill stroke at a pump chamber of the cassette.

The pressures used to operate the disposable cassette, e.g., up to 48.3 kPa (7 psig) positive pressure and −34.5 kPa (−5 psig) suction pressure, are typically less than the pressure needed to push purified water through the sterile sterilizing grade filters, which can be on the order of 138.9 to 275.8 kPa (20 to 40 psig) positive pressure. If the sterile sterilizing grade filters somehow become compromised such that they do not offer their normal flow resistance, leading to the disposable cassette seeing the, e.g., 138.9 to 275.8 kPa (20 to 40 psig) positive pressure from the water purifier for driving purified water through the filters, problems may arise. In particular, a valve chamber of the disposable cassette being closed under, e.g., 48.3 kPa (7 psig) positive pressure will be opened by the, e.g., 138.9 to 275.8 kPa (20 to 40 psig) purified water pressure. A pump chamber of the disposable cassette being closed in a pump-out stroke under, e.g., 20.7 kPa (3 psig) positive pressure will also be opened from the inside of the cassette by the, e.g., 138.9 to 275.8 kPa (20 to 40 psig) purified water pressure. The pumping membrane of the disposable cassette would be stuck against the operating surface of the cycler, and the cycler would be unable to remedy the situation.

The present disclosure sets forth multiple solutions for solving the above-described problem. In one preferred embodiment, a disposable set water line having the two sterile filters in series and configured to connect to the water purifier is provided with a water accumulator, e.g., a three liter bag, connected to the water line between the sterile sterilizing grade filters and the disposable cassette. The bag could be a separate bag or be provided as a single compartment of a two compartment bag, wherein the other compartment provides a heater/mixing container.

In an embodiment, the water line extends from the sterile sterilizing grade filters to the water accumulator at an inlet and then from an outlet of the water accumulator to the disposable cassette, such that all WFPD (as used herein, water upstream of the sterile sterilizing grade filters will be termed "purified", while water downstream from the sterile sterilizing grade filters will be termed water for peritoneal dialysis of "WFPD") is forced to flow through the water accumulator. From a pressure standpoint, the water accumulator decouples the water purifier from the disposable cassette. The water purifier is able to supply water to the water accumulator without affecting the cycler, while the cycler is able to push or pull WFPD to or from the heater/mixing bag of the disposable cassette without affecting the water accumulator.

Thus, if the sterile sterilizing grade filters somehow become compromised, the water accumulator absorbs the overpressure from the water purifier, leaving the disposable cassette and cycler unaffected. The water accumulator also provides time for one or more pressure sensor located within the water purifier to detect a pressure drop on its outlet line and for a control unit of the water purifier operating with the pressure sensor to shut down its pumps and provide an alarm (at the water purifier and/or sending a signal for the cycler to alarm) indicating a likely breech in sterilizing filter integrity. The water accumulator further provides an additional benefit by allowing the water purifier to fill the water accumulator with WFPD during all phases of operation by the PD cycler. The PD cycler operates in three phases, typically including a fill phase, a dwell phase, and a drain phase. The water accumulator may be refilled during all three phases, namely, while the cycler (i) pulls fresh dialysis fluid from the heater/mixing bag into the disposable cassette and pushes the fresh dialysis fluid to the patient, (ii) dwells, and (iii) pulls used dialysis fluid from the patient into the disposable cassette and pushes the used dialysis fluid to drain. The accumulator bag may therefore be smaller because it only needs to hold one fill volume's worth of WFPD (usually up to two liters) at a time.

In an embodiment, the control unit of the cycler sends a wired or wireless signal to the water purifier requesting a desired amount of WFPD, upon receipt of which the water purifier prepares and supplies the requested amount of WFPD to the water accumulator. In an embodiment, the water purifier delivers the requested amount of WFPD to the water accumulator while the cycler is draining used dialysis fluid from the patient and/or while delivering fresh dialysis fluid to the patient. Then, during the dwell phase, the cycler pulls the WFPD from the accumulator bag, mixes fresh dialysis fluid (described in detail below including a waffling sequence), and delivers the fresh dialysis fluid to the heater/mixing bag at the end of the waffling sequence, so that the disposable cassette is free to perform the upcoming drain.

A further advantage of the accumulator bag is that because the accumulator bag stores a supply of WFPD, and can do so when convenient, the pressure needed to drive purified water through the sterile sterilizing grade filters and the flowrate needed to provide the requested amount of WFPD may both be lower, such that the sterile sterilizing grade filters may be lower rated pressure and flowrate-wise, and thus be more economical. Lower operating pressure within the water purifier also creates less stress on its components, yielding another advantage provided by the water accumulator.

In another embodiment, the water accumulator is not provided. Instead, a water recirculation loop is created, which includes a water line extending from the water purifier to the disposable cassette and a line merging with the water line prior to the cassette to run back to the water purifier, creating a loop. The loop allows for a constant flow of WFPD to be created, which is maintained at a pressure lower than the operating pressure of the cycler. The cycler via the disposable cassette may pull WFPD from the recirculation loop as needed. If the sterile sterilizing grade filters fail, the overpressure is distributed throughout the loop, lessening the pressure impact on the cassette, and providing time for one or more pressure sensor in the water purifier to detect a pressure drop in its outlet line upstream of the sterile sterilizing grade filters, and for a control unit of the water purifier operating with the pressure sensor to shut down its pumps and provide an alarm (at the water purifier and/or sending a signal for the cycler to alarm) indicating a likely breech in sterilizing filter integrity.

As mentioned above, the present overall system prepares PD dialysis fluid at the point of use. To do so, the control unit causes the cycler to operate the disposable cassette to pump precise amounts of WFPD and at least one concentrate, such as a glucose and a buffer concentrate together for mixing and forming a dialysis fluid having a sterilization level suitable for being delivered to the peritoneal cavity of the patient. Structures to aid the mixing are discussed below. But even assuming that the resulting fluid has been mixed homogeneously, it still needs to be tested. In one embodiment, the mixed dialysis fluid is tested using one or more sensor, e.g., a conductivity sensor. For PD, the doctor typically prescribes a type of dialysis fluid to be used for treating a particular patient. Different PD dialysis fluids are typically differentiated by dextrose or glucose levels. For example, the assignee of the present disclosure provides different PD dialysis fluids having the following dextrose and glucose levels:

1.5% dextrose monohydrate (or glucose monohydrate) =1.36% anhydrous dextrose (or anhydrous glucose), 2.5% dextrose monohydrate (or glucose monohydrate) =2.27% anhydrous dextrose (or anhydrous glucose), and 4.25% dextrose monohydrate (or glucose monohydrate) =3.86% anhydrous dextrose (or anhydrous glucose). This last dialysis fluid (4.25% dextrose) may have a corresponding and repeatable conductivity measurement of 11.64 mS/cm. The 11.64 mS/cm is an example used for this description and has been found via experimentation. The conductivity setpoint for 4.25% dextrose dialysis fluid may vary based on factors such as its chemistry. Thus a resulting look-up table stored at the control unit of the cycler will need to be specific as to not only dextrose/glucose level, but to other factors such as dialysis fluid chemistry. It should be appreciated however that the other two dialysis fluid types listed above (1.5% dextrose and 2.5% dextrose) will produce different corresponding and repeatable conductivity measurements.

It is therefore contemplated to use one or more conductivity cell or sensor to confirm that the point of use dialysis solution has been mixed to the correct proportions. In one embodiment, the conductivity cell is located in the water purifier, where it may be reused. When the cycler has completed its mixing, the cycler sends a sample of the mixture down the drain line from the disposable cassette to the water purifier, which is connected to a distal end of the drain line. The sample is pushed past the one or more conductivity sensor located at the water purifier, which reads the conductivity of the sample. One or more conductivity reading is received by the control unit of the water purifier and either (i) the control unit of the water purifier analyzes the one or more reading, determines a "solution good" or "solution bad" result and sends the result wired or wirelessly to the control unit of the cycler, which either proceeds with treatment or takes an alternative action or (ii) the control unit of the water purifier sends the one or more reading to the cycler, which analyzes the one or more reading, determines a "solution good" or "solution bad" result and either proceeds with treatment or takes an alternative action. The alternative action may be either one or both of alarming or getting rid of the improperly proportioned dialysis fluid and trying again to hopefully produce a desired volume of properly mixed dialysis solution before the next fill cycle.

It should be appreciated from above that the present system may provide different dextrose or glucose level dialysis fluids for different fill procedures of the same treatment. Also, the present system may blend a particular dextrose or glucose level dialysis fluid, which has been optimized for the patient instead of having to use one of the standards dialysis fluids listed above The drain line may be a relatively long line, for example, over ten feet long. The longer drain line enables placement of the water purifier in location distant from the cycler, thereby reducing any noise from the purifier at the location where the patient is being treated. A longer drain line is advantageous in one respect because the end of the drain line is connected to the non-sterile, albeit disinfected, water purifier. Nevertheless, a long drain line means a long sample is needed to reach the one or more conductivity sensor within the water purifier. It is therefore contemplated not to pump mixed dialysis fluid all the way along the drain line to the one or more conductivity sensor inside the water purifier and to instead send only the amount of mixed dialysis fluid necessary to ensure that a proper conductivity sensor reading is, or readings are, taken. The rest of the line is filled using WFPD from the water accumulator.

In a configuration in which the water accumulator is used, when the cycler has completed the dialysis fluid preparation, the dialysis fluid resides in the heater/mixing bag. The cycler closes the cassette valve to the heater/mixing bag, opens the cassette valve to the water accumulator and pumps enough WFPD down the drain line and to the water purifier to ensure that the conductivity sensor is seeing water only, which can be checked by comparing a sensor reading to a conductivity reading expected for water only. Next, the cycler closes the cassette valve to the water accumulator, opens the cassette valve to the heater/mixing bag and pumps the necessary amount of mixed fluid (to produce a good reading(s) at the conductivity sensor) from the heater/mixing bag into the drain line. The amount of mixed fluid pumped will very likely not reach the conductivity sensor in the water purifier, so its reading(s) should not change. Then, the cycler closes the cassette valve to the heater/mixing bag, opens the cassette valve to the water accumulator and pumps enough WFPD to the water purifier to ensure that the entire amount of mixed dialysis fluid has been pumped to the sensor, and then an additional amount of WFPD to show in the sensor readings a clear end to the mixed fluid.

In a configuration in which the water accumulator is not used, the drain line may be merged with the water line just prior to the two lines mating with the disposable cassette. The drain line again runs to a conductivity sensor located inside the water purifier. Here, instead of the cycler pumping WFPD to clear the drain line prior to the pumping of the mixed fluid slug, the cycler closes the cassette valve to the combined water and drain line, and the water purifier pumps enough WFPD down the water line and into the drain line to fully prime the drain line past the one or more conductivity sensor with WFPD. Next, the cycler opens the cassette valve to the heater/mixing bag and pumps the necessary amount of mixed fluid (to produce a good reading(s) at the conductivity sensor) from the heater/mixing bag into the drain line. The amount of mixed fluid pumped will again very likely not reach the conductivity sensor in the water purifier, so its reading(s) should not change. Then, the cycler closes the cassette valve to the heater/mixing bag, and with the cassette valve to the combined water and drain line still closed, the water purifier pumps enough WFPD through the water and drain lines to ensure that the entire amount of mixed dialysis fluid has been pumped to the sensor, and then an additional amount of WFPD to show in the sensor readings a clear end to the mixed fluid.

In either configuration above, the mixed fluid will intermingle with the water at either end within the drain tube, but the majority of the mixed fluid slug between the ends will be pure mixed fluid and provide a true reading. The mixed fluid slug bound on both ends by WFPD provides good contrast marking the beginning and end of the mixed fluid readout from the one or more conductivity sensor over time. The readout is used to determine if the mixed fluid has the correct proportion as described herein.

To reduce the amount of mixed fluid that the conductivity sensor needs to see to produce a true or full reading, an estimating function may be used to estimate the conductivity value of the sensor. The estimating function enables an asymptotic value of the conductivity signal to be estimated instead of having to use the amount of mixed fluid needed to actually reach the sensed asymptotic value. The estimating function may, for example, reduce the amount of mixed fluid needed by twenty-five percent.

In one alternative embodiment, the conductivity sensor is placed inside of the cycler instead of the water purifier. Here, in one implementation the drain line runs in a first section from the cassette to the cycler, past the one or more conductivity sensor inside the cycler, and in a second section from the cycler to a house or container drain. In another implementation, an additional sample line runs in a first section from a sample port of the disposable cassette to the cycler, past the one or more conductivity sensor inside the cycler, and in a second section of the sample line from the cycler to a sample container or bag, e.g., provided as a separate chamber of a two chamber bag, the other chamber being the heater/mixing chamber. In another alternative embodiment, one or more conductivity probe is placed in the disposable cassette. The one or more probe mates with a conductivity sensor provided with the cycler when the cassette is installed in the cycler.

The conductivity readings for any of the conductivity sensor embodiments discussed herein may be temperature compensated, and thus a temperature sensor, e.g., a thermistor or thermocouple, may be provided with any of the conductivity sensor embodiments described herein. Also, in any of the conductivity sensor embodiments discussed herein, the line leading to the conductivity sensor, e.g., the drain line or a sample line, may have a one-way valve, e.g., a duck-billed check valve, that helps to prevent contaminants from migrating counter-flow up into the disposable cassette.

As discussed herein, mixing is performed at least in part inside the heater/mixing container or bag provided as part of the disposable set. The heater of the cycler is located at the top of the cycler in one embodiment, so that the heater/mixing bag may simply be placed on top of the cycler for treatment. In an embodiment, the cycler includes a lid that is closed over the heater/mixing bag to help improve heating efficiency. When the heater/mixing container is filled with fluid, the bag port that transitions the heater/mixing line to the bag itself can be bent or rotated upwardly such that the port points upwardly towards the top of the bag instead of straight out towards the far edge of the heater/mixing bag. In an embodiment, the mixing takes place as follows: the cycler delivers a smaller percentage, such as ten percent, of the prescribed WFPD to the bag, the entire glucose concentrate volume to the bag, the entire buffer concentrate volume to the bag, then the remaining, e.g., ninety, percent of the prescribed WFPD to the bag. Also, the glucose and buffer concentrates are heavier than WFPD. Thus if the bag port is rotated upwardly when providing the remaining ninety percent of the prescribed WFPD, the water can tend to shoot over the heavier concentrates and not mix homogeneously.

To solve this problem, the bag port is provided in one embodiment with first and second flanges that extend out from the port and transversely to the axis of the bag port. When the port is properly mounted into a slot formed in a sidewall of the heater tray located at the top of the cycler, the flanges extend in a sort of semicircle above the top of the bag port. The flanges are spaced apart from each other a distance corresponding to the wall thickness of the heater tray sidewall, so that one flange resides on the outside of the heater tray sidewall, while the second flange resides on the inside of the heater tray sidewall when the port is properly mounted into the sidewall slot. The flanges accordingly abut either side of the sidewall and prevent the bag port from being rotated either up towards the top of the heater/mixing bag or down towards the bottom of the heater/mixing bag. In an embodiment, a key is provided between the flanges and extends vertically up the center of the flanges, so that the heater/mixing bag cannot be loaded upside down onto the heater tray.

It is also contemplated to configure the heater lid to close onto some portion of the bag port, either onto one or both of the flanges and/or onto the tubing portion of the bag port, to clamp the bag port in place. The clamping prevents the bag port from translating upwardly within the slot of the heater tray sidewall while the heater/mixing bag is filled.

In another embodiment, the mixing takes place as follows. A sample of the first concentrate is pumped past a conductivity sensor to verify that it is the correct first concentrate. If so, a desired volume of the first concentrate is pumped to the heater/mixing bag. A sample of the second concentrate is pumped past the conductivity sensor to verify that it is the correct second concentrate. If so, a desired volume of the second concentrate is pumped to the heater/mixing bag. Next, a large percentage of the desired volume, e.g., 90 to 95%, of the WFPD is pumped to the heater/mixing bag to mix with the first and second concentrates. Once mixed, a sample of the mixture is pumped past the conductivity sensor and a reading of its conductivity is taken. The reading is compared to a desired conductivity level to determine how much more WFPD is needed to reach the desired conductivity level. That amount of WFPD is then pumped to the heater/mixing bag. A sample of the resulting mixture is then pumped past the conductivity sensor to verify that the desired conductivity level has been reached.

For any of the mixing embodiments discussed herein, to further aid the homogeneous mixing of the dialysis fluid, the control unit of the cycler is in one embodiment programmed to perform a "waffling" sequence. The waffling sequence is performed for example after the remaining ninety percent of the prescribed WFPD is added to the bag to mix with the concentrates already in the bag. The disposable cassette is in one embodiment provided with two pumping chambers, so what while one pump chamber is filling with a fluid, the other pump chamber can expel fluid to provide a relatively continuous flow of fluid to or from the cassette. The waffling sequence in one embodiment involves the cycler causing the pump chambers to pull the dialysis fluid to be mixed from the heater/mixing bag into the pump chambers and then push the dialysis fluid to be mixed back into the heater/mixing bag. This procedure is repeated over and over until, for example, 200 percent of the heater/mixing bag volume is pumped back and forth. The pump chambers may be caused to fill and expel together or to have one pump chamber fill, while the other pump chamber expels. Having one pump chamber fill while the other expels might be possible at the same time through a single heater/mixing line, but if not, having one pump chamber fill while the other expels could be performed at alternating times.

The waffling sequence is performed in one embodiment while the mixing fluid is being heated in the heater/mixing bag. In an embodiment, pumping to the heater/mixing bag is performed at about 24.8 kPa (3.6 psig). The electrically operated valves controlling pneumatic pressure to the pump chambers are in one embodiment variable pneumatic valves. It is accordingly contemplated to vary the input signal to the variable pneumatic valves during the waffling sequence, e.g., in a pulse, cyclic or sinewave like manner, such as 3.5 kPa (0.5 psig) up and down from the 24.8 kPa (3.6 psig) pumping pressure. The pulsed pressure output may further promote turbulent flow and thus mixing.

The disposable set including the one or more sterilizing filter is discarded after each use in one embodiment. In alternative embodiments, the disposable set including the cassette, associated lines, heater/mixing bag, water accumulator (if provided) and one or more sterilizing filter are reused for one or more additional treatment. To do so, it is contemplated to flush the disposable cassette with WFPD at the end of treatment to push residual used dialysis fluid from the cassette and the drain line to drain. The patient disconnects the patient line from the patient's transfer set (which leads to the patient's indwelling peritoneal catheter) and caps the transfer set and patient line each with a cap, e.g., a cap containing a disinfectant. In an alternative embodiment, the drain line, for example, is provided with a port for connecting to the end of the patient line between treatments to create a patient line loop that may be more effectively flushed or disinfected. The concentrate lines of the cassette are left connected to the concentrate containers. The water line from the cassette is left connected to the water purifier. The drain line from the cassette is left connected to drain, e.g., via a drain line connection to the water purifier having the at least one conductivity sensor as discussed herein.

In an embodiment, the number of times that the disposable set may be reused is keyed off of the level of concentrates in the concentrate containers. For example, the concentrate containers may be configured to hold and provide three treatment's worth of concentrate (plus some extra to ensure three full treatments). It is therefore intended that the disposable set be reused two times, so that at the end of three treatments, the patient may simply remove the disposable set with concentrate containers connected from the cycler for disposal, and reconnect a new disposable set along with two new concentrate containers. As discussed herein, however, it is possible that the cycler may prepare a batch of mixed dialysis fluid whose conductivity reading does not meet a designated conductivity (or fall with a designated range of conductivities) for the prescribed dextrose or glucose level concentrate, such that the batch is thereafter discarded. Here, an amount of concentrate may be consumed so that three full treatments are no longer possible. It is contemplated therefore that the control unit of the cycler keep track of the amount of each concentrate consumed over the three treatment period so that the control unit may (i) prevent the user from beginning a treatment when there is not enough of either concentrate to complete the treatment and/or (ii) provide an option to the user to perform a treatment with one or more less cycles.

In an embodiment, when the user installs a new set with new concentrate containers, the control unit may know that the concentrate containers are new by (i) input indicating same from the patient or user, (ii) sensing/reading a new barcode, 3d barcode, radio frequency identifier ("RFID") tag, or other sensed identifier provided with the new concentrate containers, e.g., provided on a connecter extending from the containers, or (iii) a combination of (i) and (ii). When the control unit of the cycler senses the new containers, the control unit resets the amount of each concentrate consumed to zero.

To aid in the reuse of the disposable set, it is contemplated to use a supply of a bacterial growth prevention agent, such as citric acid, citrate, or a derivative thereof. In an embodiment, the supply of the bacterial growth prevention agent is connected as an input to the water purifier. The water purifier as a last step at the end of treatment mixes a desired amount of the bacterial growth prevention agent into the purified water, which is then brought to a sterilization level suitable for being delivered to the peritoneal cavity of the patient via the sterile sterilizing grade filters and delivered to the water accumulator in one embodiment. The cycler in its last step at the end of treatment pulls WFPD including the growth inhibitor from the water accumulator and pumps the water and inhibitor into and through the cassette, drain line and possibly even the heater/mixing container. In a further alternative embodiment, hot water heated at the water purifier, e.g., to 70° C., may be used to disinfect the disposable set between treatments.

In light of the present disclosure, and without limiting the disclosure in any way, in a first aspect, which may be combined with any other aspect listed herein unless specified otherwise, a peritoneal dialysis system includes: a cycler including a pump actuator, a heater and a heating pan operable with the heater, wherein the heating pan includes a sidewall forming a slot; and a disposable set operable with the cycler, the disposable set including a pumping cassette including a pump chamber configured to be actuated by the pump actuator, a heater/mixing container in fluid communication with the pumping cassette and sized to be received at the heating pan, the heater/mixing container including a port configured such that when the port is slid into the slot of the heater pan sidewall, the port is prevented from rotating about an axis transverse to a direction of flow through the port.

In a second aspect of the present disclosure, which may be combined with any other aspect listed herein unless specified otherwise, the slot includes an angled or V-shaped section through which a portion of the port is inserted and a circular section for receiving the portion of the port.

In a third aspect of the present disclosure, which may be combined with any other aspect listed herein unless specified otherwise, a transition from the angled or V-shaped section to the circular section of the second aspect is sized so that the portion of the port press-fits through the transition to provide tactile feedback.

In a fourth aspect of the present disclosure, which may be combined with any other aspect listed herein unless specified otherwise, the port includes first and second flanges which abut first and second sides of the sidewall when the port is slid into the slot to prevent the port from rotating about an axis transverse to the direction of flow through the port.

In a fifth aspect of the present disclosure, which may be combined with any other aspect listed herein unless specified otherwise, the port includes a member that abuts first and second sides of the slot when the port is slid into the slot to prevent the port from rotating about an axis inline with the direction of flow through the port.

In a sixth aspect of the present disclosure, which may be combined with any other aspect listed herein unless specified otherwise, the member of the fifth aspect is positioned and arranged to prevent the heater/mixing container from being loaded upside down onto the heating pan.

In a seventh aspect of the present disclosure, which may be combined with any other aspect listed herein unless specified otherwise, a disposable set for a peritoneal dialysis system is provided including a cycler having a heater and a heating pan operable with the heater, wherein the heating pan includes a sidewall forming a slot, the disposable set including: a heater/mixing container sized to be received at the heating pan, the heater/mixing container including a port configured such that when the port is slid into the slot of the heater pan sidewall, the port is prevented from rotating about an axis transverse to a direction of flow through the port.

In an eighth aspect of the present disclosure, which may be combined with any other aspect listed herein unless specified otherwise, the port includes first and second flanges which abut first and second sides of the sidewall when the port is slid into the slot to prevent the port from rotating about an axis transverse to the direction of flow through the port.

In a ninth aspect of the present disclosure, which may be combined with any other aspect listed herein unless specified otherwise, the port includes a member that abuts first and second sides of the slot when the port is slid into the slot to prevent the port from rotating about an axis inline with the direction of flow through the port.

In a tenth aspect of the present disclosure, which may be combined with any other aspect listed herein unless specified otherwise, the member is positioned and arranged to prevent the heater/mixing container from being loaded upside down onto the heating pan.

In an eleventh aspect of the present disclosure, which may be combined with any other aspect listed herein unless specified otherwise, a peritoneal dialysis system includes: a cycler including a control unit and a pump actuator under control of the control unit; and a disposable set operable with the cycler, the disposable set including a pumping cassette having a pump chamber configured to be actuated by the pump actuator, and a mixing container in fluid communication with the pumping cassette, wherein the control unit is programmed to promote mixing of at least two fluids by (i) causing the pump actuator to operate the pump chamber to pull the at least two fluids from the mixing container into the pump chamber, (ii) thereafter causing the pump actuator to operate the pump chamber to push the at least two fluids from the pump chamber to the mixing container, and (iii) repeating (i) and (ii) at least one time.

In a twelfth aspect of the present disclosure, which may be combined with any other aspect listed herein unless specified otherwise, the control unit is configured such that after (i), (ii) and (iii) of the eleventh aspect are performed, a sample of the mixed at least two fluids is caused to undergo a test using a sensor, and wherein at least one of prior to or after the test the sensor is bypassed or used for a different purpose.

In a thirteenth aspect of the present disclosure, which may be combined with any other aspect listed herein unless specified otherwise, wherein after (i), (ii) and (iii) of the eleventh aspect are performed, the control unit is configured to cause a sample of the mixed at least two fluids to undergo a test and to cause (i), (ii) and (iii) to be performed again if the sample does not pass the test.

In a fourteenth aspect of the present disclosure, which may be combined with any other aspect listed herein unless specified otherwise, the test of the thirteenth aspect includes comparing a measured property of the sample to a setpoint for the property.

In a fifteenth aspect of the present disclosure, which may be combined with any other aspect listed herein unless specified otherwise, the mixed at least two fluids form a volume, and wherein in (iii), (i) and (ii) are repeated until a certain percentage of the volume is pulled and pushed by the pump chamber.

In a sixteenth aspect of the present disclosure, which may be combined with any other aspect listed herein unless specified otherwise, the certain percentage of the volume of the fifteenth aspect is greater than 100 percent.

In a seventeenth aspect of the present disclosure, which may be combined with any other aspect listed herein unless specified otherwise, the pump actuator is a first pump actuator and the pump chamber is a first pump chamber, wherein the cycler includes a second pump actuator under control of the control unit, wherein the pumping cassette has a second pump chamber configured to be actuated by the second pump actuator, and wherein the control unit is programmed to promote mixing of the at least two fluids by (i) causing the first and second pump actuators to simultaneously operate the first and second pump chambers to pull the at least two fluids from the mixing container into the first and second pump chambers, and (ii) thereafter causing the first and second pump actuators to simultaneously operate the first and second pump chambers to push the at least two fluids from the pump chamber to the mixing container.

In an eighteenth aspect of the present disclosure, which may be combined with any other aspect listed herein unless specified otherwise, the mixing container is a heater/mixing bag.

In a nineteenth aspect of the present disclosure, which may be combined with any other aspect listed herein unless specified otherwise, a peritoneal dialysis system includes: a source of water made suitable for peritoneal dialysis ("WFPD"); at least one source of concentrate; a cycler including a control unit and a pump actuator under control of the control unit; and a disposable set operable with the cycler and in fluid communication with the source of water and the at least one source of concentrate, the disposable set including a pumping cassette including a pump chamber configured to be actuated by the pump actuator, and a mixing container in fluid communication with the pumping cassette, wherein the control unit is programmed to mix the WFPD and the at least one concentrate by causing (i) the pump actuator to operate the pump chamber to pump a first amount of the WFPD to the mixing container, (ii) the pump actuator to operate the pump chamber to pump a prescribed amount of the at least one concentrate from the at least one concentrate source to the mixing container, and (iii) the pump actuator to operate the pump chamber to pump a second amount of the WFPD to the mixing container.

In a twentieth aspect of the present disclosure, which may be combined with any other aspect listed herein unless specified otherwise, the control unit is configured to cause a sample of the mixed WFPD and the at least one concentrate to undergo a test using a sensor, and wherein at least one of prior to or after the test the sensor is bypassed or used for a different purpose.

In a twenty-first aspect of the present disclosure, which may be combined with any other aspect listed herein unless specified otherwise, the sensor of the twentieth aspect is located at the source of water.

In a twenty-second aspect of the present disclosure, which may be combined with any other aspect listed herein unless specified otherwise, the system includes plural sources of concentrate, and wherein in (ii) the pump actuator operates the pump chamber to pump prescribed amounts of each concentrate from its concentrate source to the mixing container.

In a twenty-third aspect of the present disclosure, which may be combined with any other aspect listed herein unless specified otherwise, the prescribed amount of the at least one concentrate is a total amount needed for the at least one concentrate.

In a twenty-fourth aspect of the present disclosure, which may be combined with any other aspect listed herein unless specified otherwise, the first and second amounts of the WFPD add to a total amount needed for the WFPD.

In a twenty-fifth aspect of the present disclosure, which may be combined with any other aspect listed herein unless specified otherwise, the water is made suitable for peritoneal dialysis, at least in part, at the source of water.

In a twenty-sixth aspect of the present disclosure, which may be combined with any other aspect listed herein unless specified otherwise, a peritoneal dialysis system includes: a cycler including a control unit and a pump actuator under control of the control unit; and a disposable set operable with the cycler, the disposable set including (i) a pumping cassette having a pump chamber configured to be actuated by the pump actuator, and (ii) a mixing container in fluid communication with the pumping cassette, wherein the control unit is programmed to disinfect the disposable set between treatment by (i) causing the pump actuator to operate the pump chamber to pull the at least one of hot water and a growth inhibiting agent from the mixing container into the pump chamber, (ii) thereafter causing the pump actuator to operate the pump chamber to push the at least one of hot water and a growth inhibiting agent to the mixing container, and (iii) repeating (i) and (ii) at least one time.

In a twenty-seventh aspect of the present disclosure, which may be combined with any other aspect listed herein unless specified otherwise, the growth inhibiting agent of the twenty-sixth aspect include citric acid, citrate or a derivative thereof.

In a twenty-eighth aspect of the present disclosure, any of the structure, functionality and alternatives described in connection with any one of FIGS. 1 to 20 may be used in combination with any of the structure, functionality and alternatives described in connection with any other ones of FIGS. 1 to 20.

It is accordingly an advantage of the present disclosure to provide an improved peritoneal dialysis system.

It is another advantage of the present disclosure to provide a peritoneal dialysis system that prepares dialysis fluid having a sterilization level suitable for being delivered to the peritoneal cavity of the patient at the point of use.

It is a further advantage of the present disclosure to provide a peritoneal dialysis system that prepares dialysis fluid having a sterilization level suitable for being delivered to the peritoneal cavity of the patient at the point of use safely.

It is still a further advantage of the present disclosure to provide a peritoneal dialysis system that mixes dialysis fluid having a sterilization level suitable for being delivered to the peritoneal cavity of the patient at the point of use effectively.

It is still another advantage of the present disclosure to provide a peritoneal dialysis system that effectively tests the proportional accuracy of dialysis fluid made at the point of use.

It is yet a further advantage of the present disclosure to provide a peritoneal dialysis system that allows for the reuse of disposable components.

Further still, it is an advantage of the present disclosure to provide dialysis fluids having dextrose or glucose levels optimized for the patient.

Still further, it is an advantage of the present disclosure to provide dialysis fluid treatments that optimally provide different dextrose or glucose level dialysis fluids for different fill procedures of a same treatment.

Moreover, it is an advantage of the present disclosure to use a disinfection procedure performed routinely at a water purifier between treatments to aid in the formation of water suitable for peritoneal dialysis at the time of treatment.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIGS. 3A to 3D are various views of one embodiment for concentrate connectors used with any of the disposable sets of the present disclosure including the disposable set of FIG. 2.

FIGS. 4A to 4G illustrate various views of one embodiment of a heater/mixing bag port and associated heater/mixing pan sidewall of the present disclosure.

DETAILED DESCRIPTION

Cycler and Disposable Set

Figure 1:
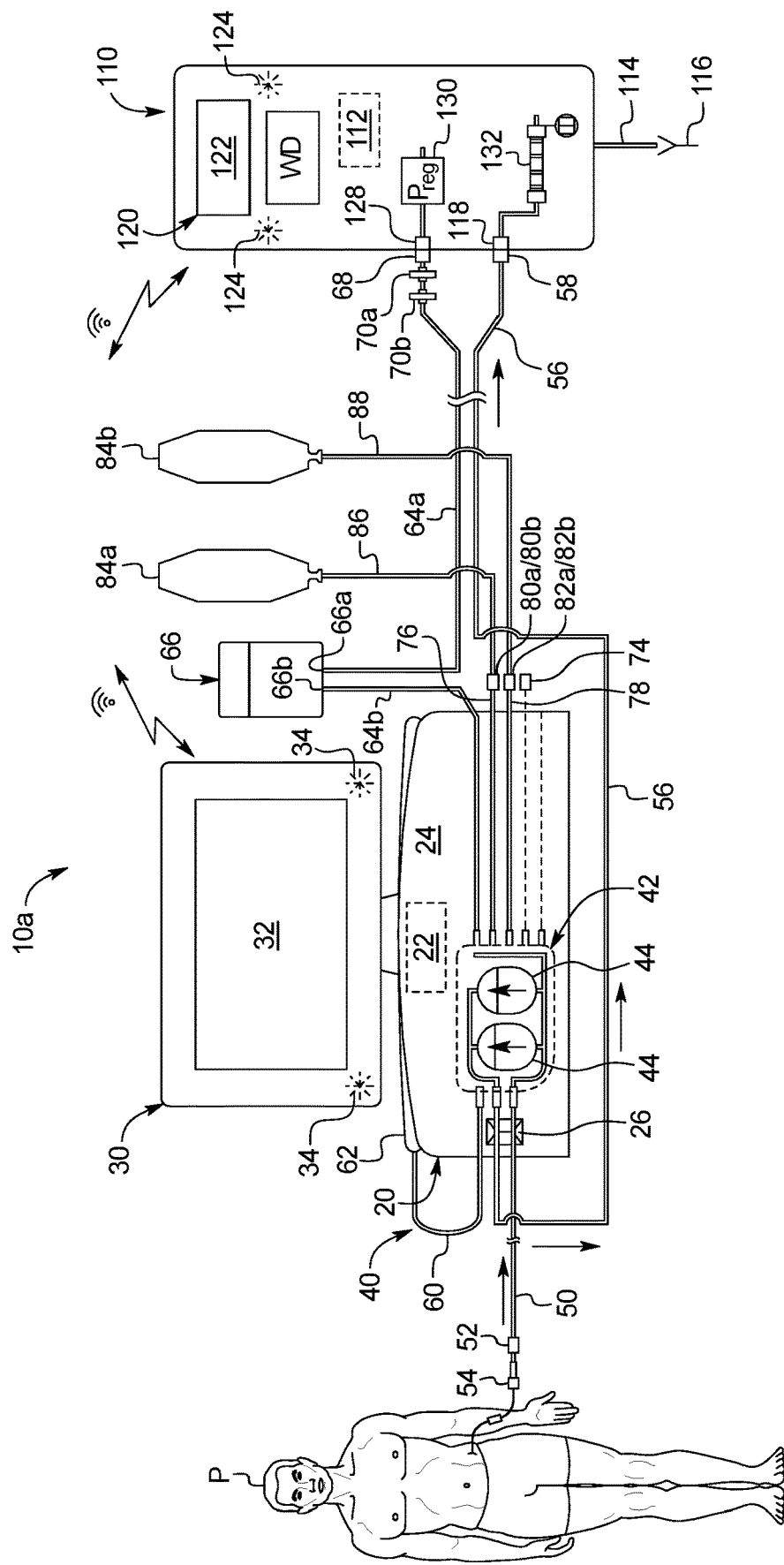
FIG. 1 is a front elevation view of one embodiment of a peritoneal dialysis system having point of use dialysis fluid production of the present disclosure.

Referring now to the drawings and in particular to FIG. 1, one embodiment of a peritoneal dialysis system having point of use dialysis fluid production of the present disclosure is illustrated by system 10a. System 10a includes a cycler 20 and a water purifier 110. Suitable cyclers for cycler 20 include, e.g., the Amia® or HomeChoice® cycler marketed by Baxter International Inc., with the understanding that those cyclers need updated programming to perform and use the point of use dialysis fluid produced according to system 10a. To this end, cycler 20 includes a control unit 22 having at least one processor and at least one memory. Control unit 22 further includes a wired or wireless transceiver for sending information to and receiving information from a water purifier 110. Water purifier 110 also includes a control unit 112 having at least one processor and at least one memory. Control unit 112 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier includes a drain line 114 leading to a drain 116, which can be a housing drain or drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, for providing positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off solenoid pneumatic valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (viii) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 110 in the illustrated embodiment also includes a user interface 120. Control unit 112 of water purifier 110 in an embodiment includes a video controller, which may have its own processing and memory for interacting with primary control processing and memory of control unit 112. User interface 120 includes a video monitor 122, which may likewise operate with a touch screen overlay placed onto video monitor 122 for inputting commands into control unit 112. User interface 120 may also include one or more electromechanical input device, such as a membrane switch or other button. Control unit 112 may further include an audio controller for playing sound files, such as alarm or alert sounds, at one or more speaker 124 of water purifier 110.

Figure 2:
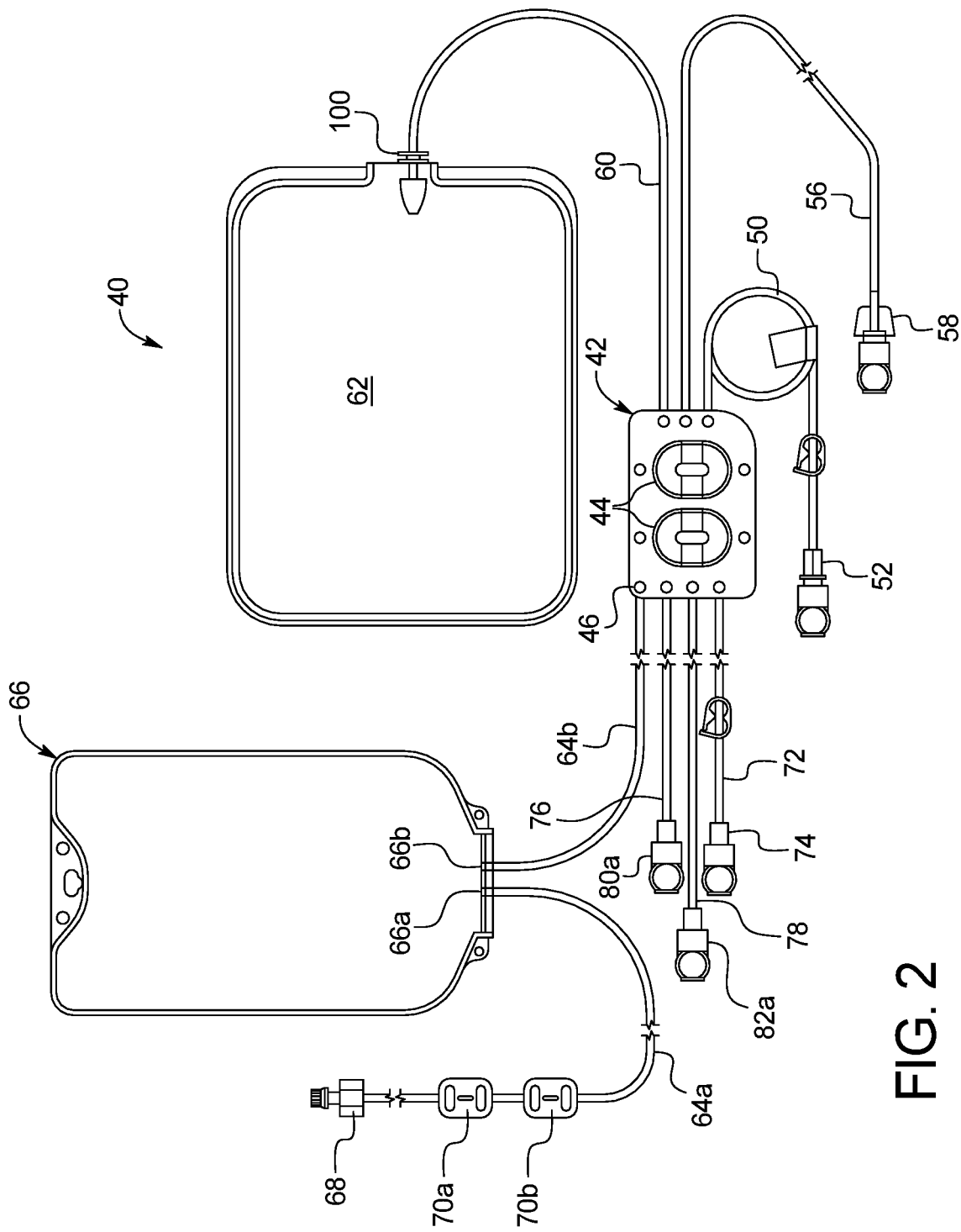
FIG. 2 is an elevation view of one embodiment of a disposable set used with the system illustrated in FIG. 1.

Referring additionally to FIG. 2, one embodiment of disposable set 40 illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 illustrates that drain line connector 58 connects removeably to a drain connector 118 of water purifier 110.

FIGS. 1 and 2 further illustrate that disposable set 40 includes a heater/mixing line 60 that extends from a heater/mixing line port of cassette 42 and terminates at a heater/mixing bag 62 discussed in more detail below. Disposable set 40 includes an upstream water line segment 64a that extends to a water inlet 66a of water accumulator 66. A downstream water line segment 64b extends from a water outlet 66b of water accumulator 66 to cassette 42. In the illustrated embodiment, upstream water line segment 64a begins at a water line connector 68 and is located upstream from water accumulator 66. FIG. 1 illustrates that water line connector 68 is removeably connected to a water outlet connector 128 of water purifier 110.

Water purifier 110 outputs water and possibly water suitable for peritoneal dialysis ("WFPD"). To ensure WFPD, however, a sterile sterilizing grade filter 70a is placed upstream from a downstream sterile sterilizing grade filter 70b, respectively. Filters 70a and 70b may be placed in water line segment 64a upstream of water accumulator 66. Sterile sterilizing grade filters 70a and 70b may be pass-through filters that do not have a reject line. Pore sizes for sterilizing filter may, for example, be less than a micron, such as 0.1 or 0.2 micron. Suitable sterile sterilizing grade filters 70a and 70b may, for example, be Pall IV-5 or GVS Speedflow filters, or be filters provided by the assignee of the present disclosure. In an embodiment, only one upstream or downstream sterilizing filter 70a and 70b is needed to produce WFPD, that is, water suitable for making dialysis fluid for delivery to the peritoneal cavity of patient P, nevertheless, two sterile sterilizing grade filters 70a and 70b are provided for redundancy in case one fails.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first, e.g., glucose, concentrate line 76 extending from a first concentrate port of cassette 42 and terminates at a first, e.g., glucose, cassette concentrate connector 80a. A second, e.g., buffer, concentrate line 78 extends from a second concentrate port of cassette 42 and terminates at a second, e.g., buffer, cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing bag 62 onto cycler 20, (ii) connects upstream water line segment 64a to water outlet connector 128 of water purifier 110, (iii) connects drain line 56 to drain connector 118 of water purifier 110, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared and verified as described in detail below, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyletser ether ("PCCE") and may be of one or more layer. Any of the tubing or lines may be made for example of polyvinyl chloride ("PVC"). Any of the connectors may be made for example of acrylonitrile-butadiene-styrene ("ABS", e.g., for concentrate connectors 80a, 80b, 82a, 82b and heater/mixing bag connector 100 discussed below), acrylic (e.g., for drain line connector 58) or PVC (e.g., for water line connector water line connector 68). Any of the bags or containers may be made of PVC. The materials for any of the above components may be changed over time.

Fail Safe Connection of Concentrate Connectors and Water Purifier Connectors

Referring now to FIGS. 3A to 3D, example embodiments for first cassette concentrate connector 80a, first container concentrate connector 80b, second cassette concentrate connector 82a and second container concentrate connector 82b are illustrated. In general, the inner workings of the connectors are sized differently, so that (i) first cassette concentrate connector 80a cannot be connected to second container concentrate connector 82b, and (ii) second cassette concentrate connector 82a cannot be connected to first container concentrate connector 80b. And because (i) first cassette concentrate connector 80a and second cassette concentrate connector 82a are permanently attached to cassette 42 via their respective 76, 78, and (ii) first container concentrate connector 80b and second container concentrate connector 82b are permanently attached to their respective concentrate container 84a, 84b via their respective lines 86, 88, patient P cannot connect concentrate containers 84a, 84b to cassette 42 improperly.

Figure 3A:
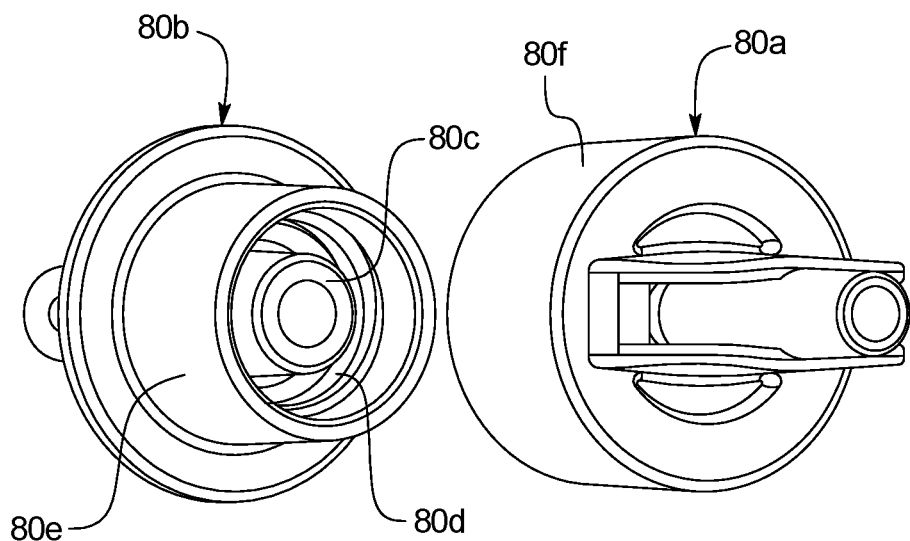
Figure 3A:
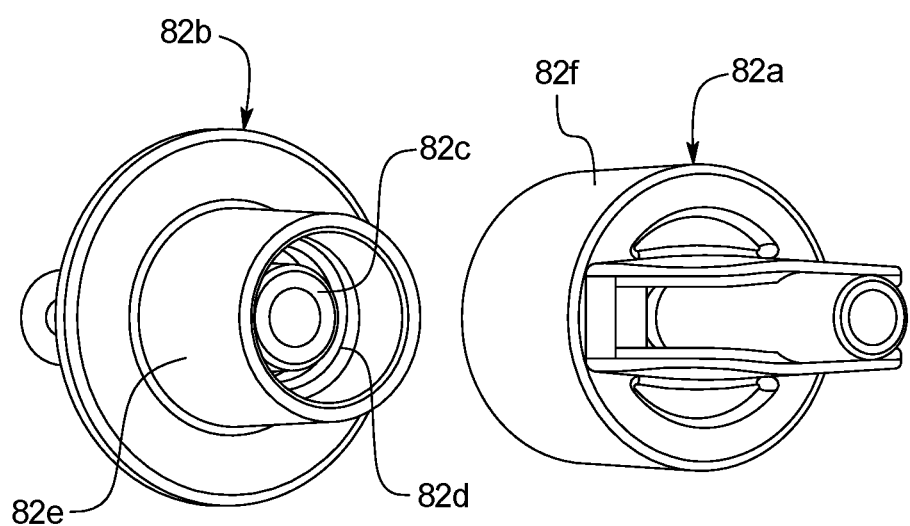

FIGS. 3A to 3D in general illustrate that glucose connectors 80a/80b are larger in multiple respects than buffer connectors 82a/82b. In an alternative embodiment, the buffer connectors are larger in multiple respects than the glucose connectors. In either case, FIG. 3A illustrates that male luer port 80c of male luer connector 80b has a larger outer diameter than male luer port 82c of male luer connector 82b FIG. 3A also illustrates that female threads 80d of male luer connector 80b have a larger inner diameter than the inner diameter of female threads 82d of male luer connector 82b. FIGS. 3A to 3D further illustrate that outer annular wall 80e of male luer connector 80b has a larger inner diameter than the inner diameter of outer annular wall 82e of male luer connector 82b, while outer annular wall 80f of female luer connector 80a has a larger inner diameter than the inner diameter of outer annular wall 82f of female luer connector 82a.

Figure 3B:
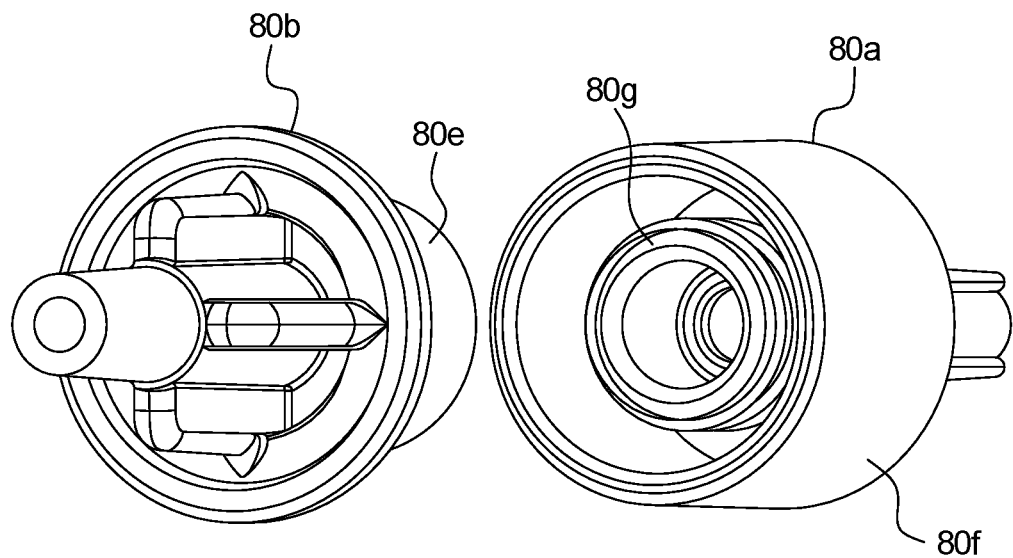
Figure 3B:
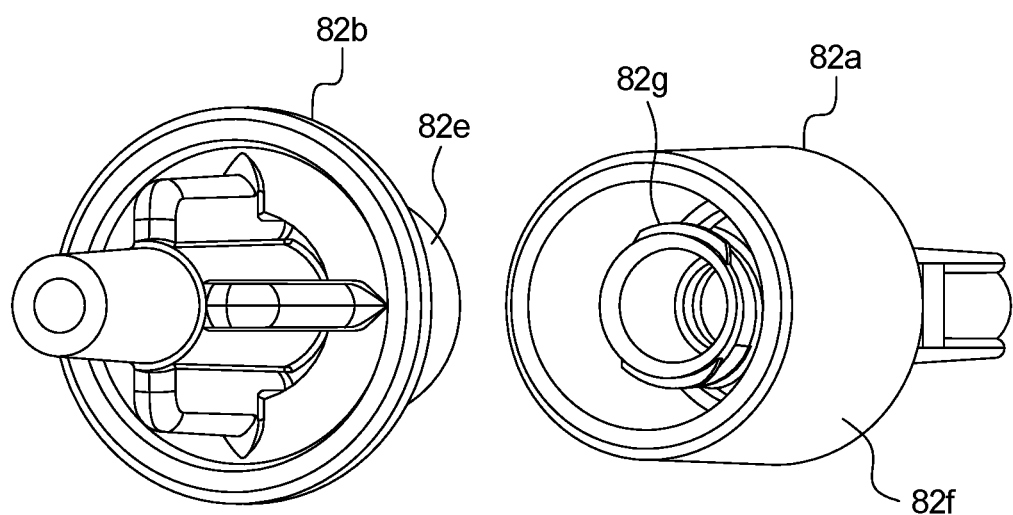
Figure 3C:
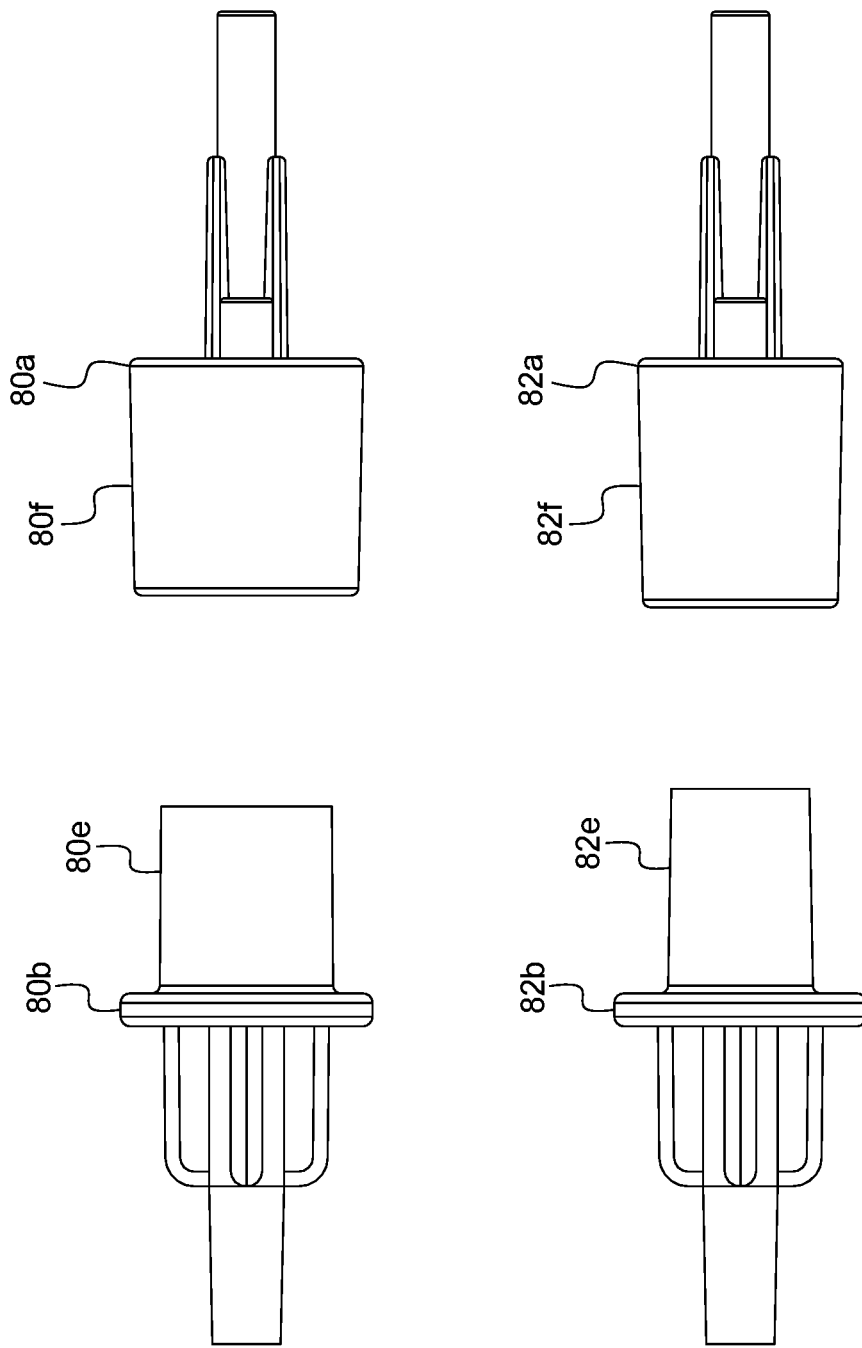

FIG. 3B further illustrates that male threads 80g of female luer connector 80a are larger in outer diameter than the outer diameter of male threads 82g of female luer connector 82a. The cross-section of FIG. 3D confirms everything above, including (i) female threads 80d of male luer connector 80b having a larger inner diameter than the inner diameter of female threads 82d of male luer connector 82b, and (ii) male threads 80g of female luer connector 80a having a larger outer diameter than the outer diameter of male threads 82g of female luer connector 82a. FIG. 3D also illustrates that the shroud differential "D" provided by outer annular wall 82e of male luer connector 82b is longer than shroud differential "d" provided by outer annular wall 80e of male luer connector 80b. The differently sized threads and the different shroud differentials D and d, in particular, prevent patient P from connecting the concentrate containers 84a, 84b to cassette 42 improperly.

It should be appreciated that differently sized mating connectors, such as differently sized luer mating connectors 80a/80b versus 82a/82b, may also be used for other connector pairs, including water line connector 68/water outlet connector 128 and drain line connector 58/drain connector 118 at the connection to water purifier 110. Here, the differently sized connector pairs prevent patient P or other user from connecting (i) upstream water line segment 64a to drain connector 118 and/or (ii) drain line 56 to water outlet connector 128.

In one preferred embodiment, drain line connector 58 and water line connector 68 are threaded but are not true luer connectors, so they cannot mate with any of differently sized luer mating connectors 80a/80b and 82a/82b. Connectors 58 and 68 also cannot mate with transfer set 54, so the connectors may only be connected to water purifier 110. In an embodiment, drain line connector 58 and water line connector 68 are configured to be connected together, so that after treatment, patient P or other user may remove disposable set 40 from cycler 20 and water purifier 110 and connect upstream water line segment 64a and drain line 56 together via the connection of water line connector 68 to drain line connector 58. By doing so, WFPD in upstream water line segment 64a and effluent dialysis fluid in drain line 56 cannot spill from those lines upon disconnection after treatment. Configuring drain line connector 58 and water line connector 68 to be connected together also prevents patient P or other user from (i) connecting drain line connector 58 to water outlet connector 128 because they are the same (male or female) connector and (ii) connecting water line connector 68 to drain connector 118 because they are also the same (female or male) connector.

Different concentrate connectors 80a/80b and 82a/82b and/or configuring drain line connector 58 and water line connector 68 to be connected together may, including any alternative embodiments described in connection with FIGS. 3A to 3D, be used for any of the different peritoneal dialysis systems 10a to 10d having point of use dialysis fluid preparation described herein.

Heater/Mixing Bag Connector

Figure 4A:
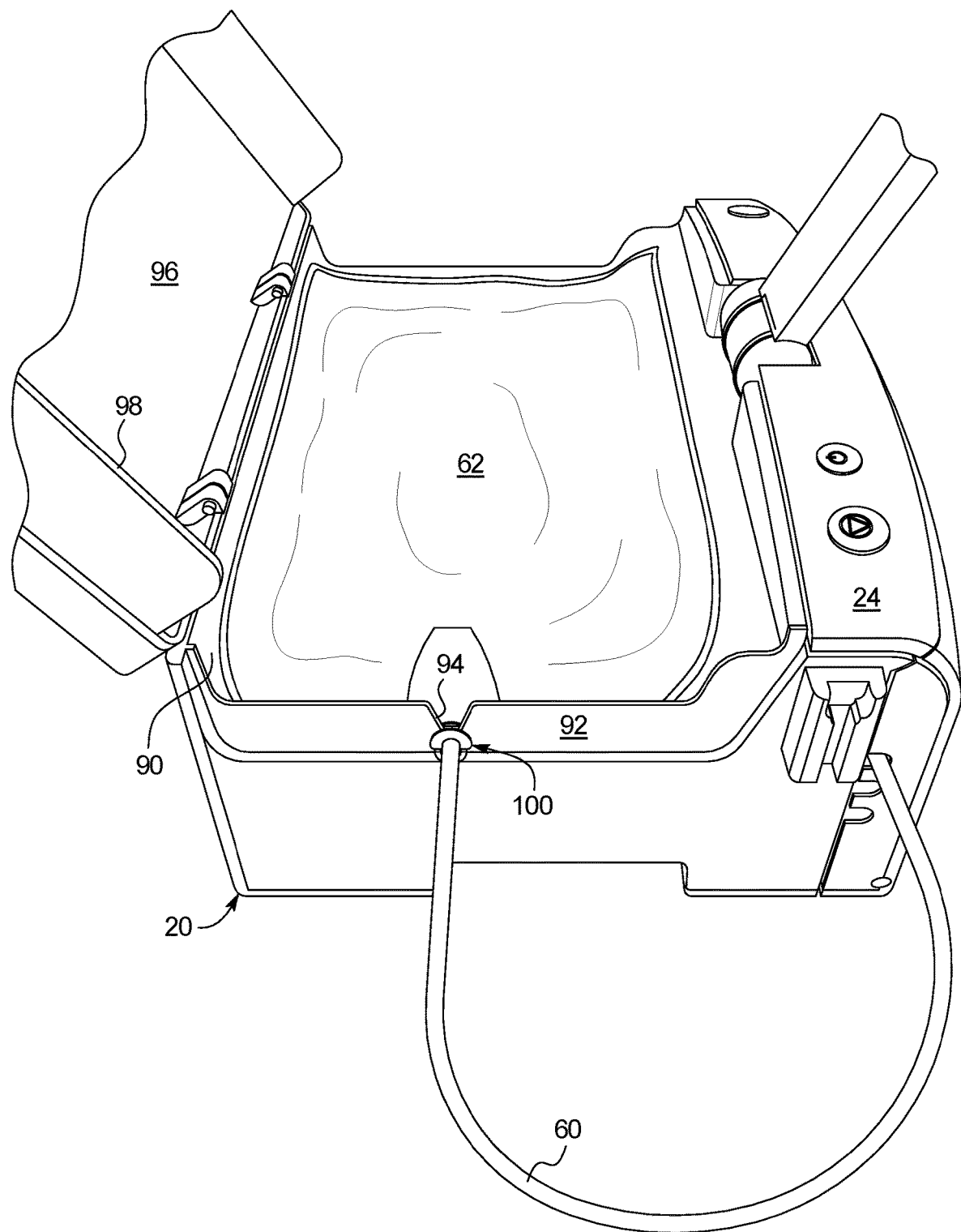

Referring now to FIGS. 4A to 4G in light of FIG. 1, the placement of heater/mixing bag 62 for operation is illustrated in detail. FIG. 4A illustrates a heating/mixing portion of housing 24 of cycler 20. Housing 24 includes a heater/mixing tray 90 located at the top of housing 24 for receiving heater/mixing bag 62. The heater of cycler 20, under control of control unit 22, is located beneath heater/mixing tray 90 and in one embodiment includes heating elements that contact heater/mixing tray 90. Heater/mixing tray 90 includes plural sidewalls including sidewall 92 that defines a slot 94 for receiving a heater/mixing bag connector 100 described in detail below. Housing 24 also defines a lid 96 connected hingedly to the back of housing 24 at the top of heater heater/mixing tray 90. Lid 96 may be hinged open to locate and remove heater/mixing bag 62 and hinged closed onto housing 24 for insulation during heating. Lid 96 includes a sidewall 98 that mates with sidewall 92 as described in more detail below. Lid 96 and sidewall 92 of housing 24 may be made of metal or plastic, while heater/mixing tray 90 is made of metal, such as aluminum, for conducting and withstanding heat.

Figure 4B:
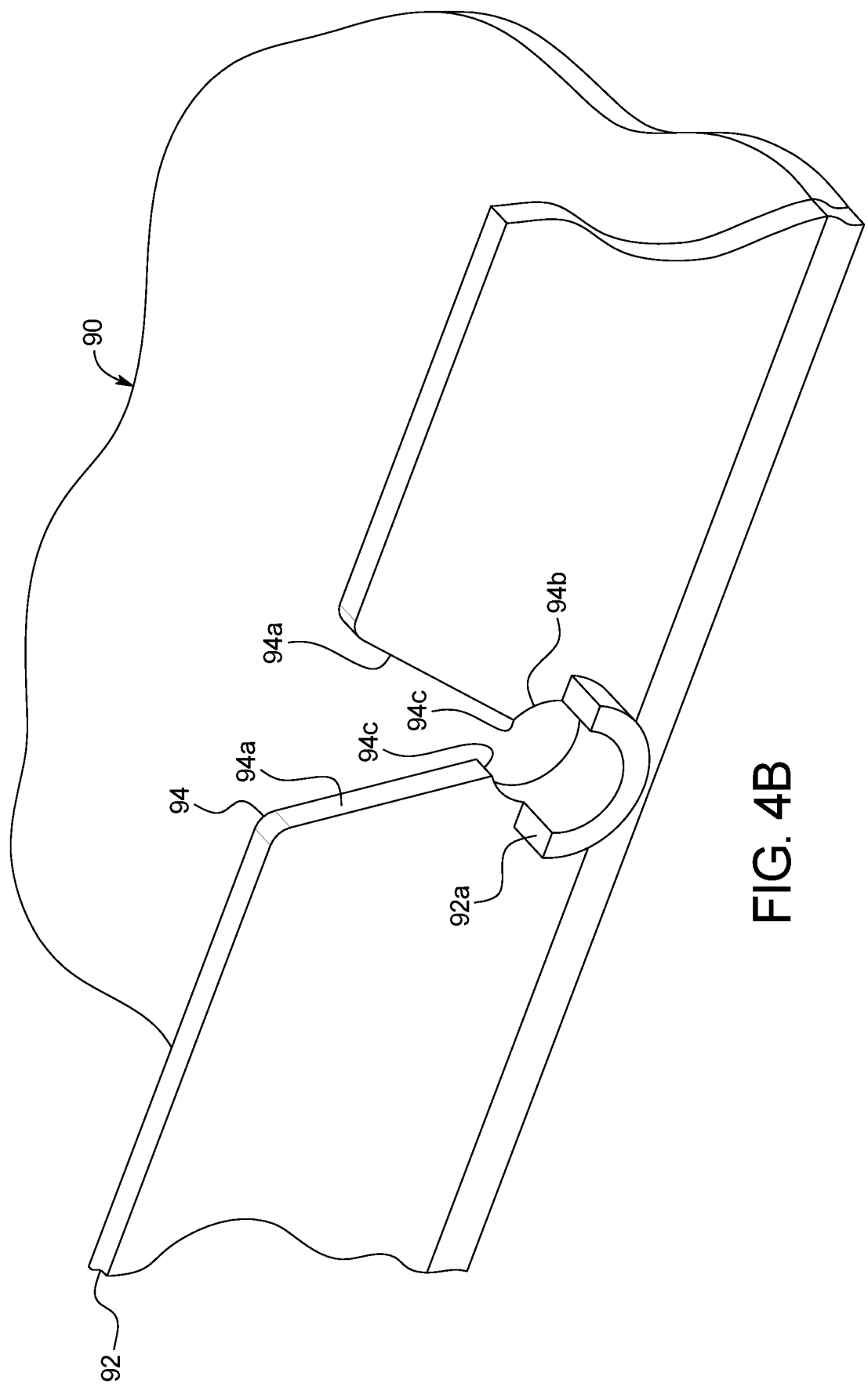

FIG. 4B illustrates the pertinent section of sidewall 92 including slot 94 in more detail. A sectioned semi-circular flange 92a extends from sidewall 92. Semi-circular flange 92a may be formed with or welded to sidewall 92. Semi-circular flange 92a helps to align heater/mixing bag connector 100, so that the port extends horizontally through sidewall 92 and roughly parallel with the bottom of heater/mixing tray 90. Slot 94 in the illustrated embodiment includes an introductory V-shaped section 94a, which extends to a resting circular section 94b. A pinch point 94c separating V-shaped section 94a and circular section 94b is smaller than the contacting diameter of heater/mixing bag connector 100 in one embodiment. Patient P or other user accordingly feels a tactile "snap" when installing heater/mixing bag connector 100 into resting circular section 94b, indicating a proper and final installation. Pinch point 94c also tends to hold heater/mixing bag connector 100 in place, preventing the port from translating upwardly within slot 94, e.g., while heater/mixing bag 62 is being filled.

Figure 4C:
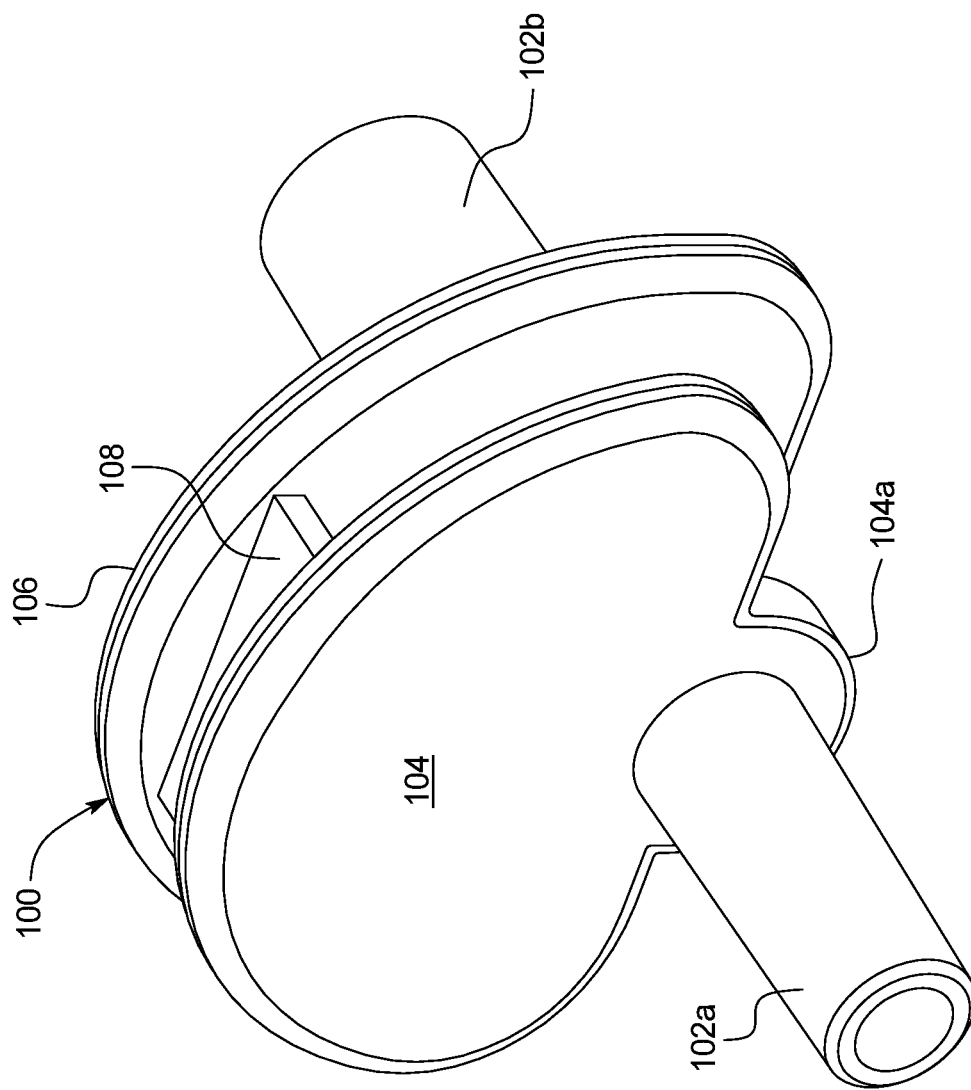

FIG. 4C illustrates one embodiment for heater/mixing bag connector 100. Heater/mixing bag connector 100 may be made of a material having a sufficiently low physiological impact on the patient fluid and thereby on patient P. Heater/mixing bag connector 100 may be molded as a single piece or as multiple pieces fitted sealingly together. Heater/mixing bag connector 100 includes a tube connection port 102a for sealingly attaching to heater/mixing line 60 (FIG. 1). Tube connection port 102a extends to an outer flange 104. Outer flange 104 is offset from an inner flange 106 via an anti-rotation key 108. A bag introduction port 102b extends from inner flange 106 into heater/mixing bag 62. In an embodiment, heater/mixing bag 62 is sealed to bag introduction port 102b via heat sealing, sonic welding or solvent bonding.

The interior lumen of bag introduction port 102b may have a constant diameter cylindrical shape or be nozzled. If nozzled, the axis or centerline of the nozzle may point horizontally or point downwardly towards the bottom of heater/mixing tray 90. The concentrates, such as glucose and buffer, are generally heavier than the WFPD with which the concentrates are mixed. It may accordingly be desirable to point the direction of concentrates and water entering heater/mixing bag 62 downwardly, so that the concentrates and water have more time to mix before the lighter water separates upwardly from the heavier concentrates.

In an embodiment, there is no tube extending off of the distal end of introduction port 102b, so that concentrates and water exit introduction port 102b freely into heater/mixing bag 62. In an alternative embodiment, a diffusing manifold (not illustrated) may be attached sealingly to the distal end of introduction port 102b. The diffusing manifold may, for example, be a rigid or flexible tube that is capped at its distal end. The tube includes multiple openings or apertures spaced along its length, which allow the concentrates and water to exit into heater/mixing bag 62. The diffusing manifold in this way distributes the concentrates more evenly across the entire length of heater/mixing bag 62 and forces the concentrates and the WFPD to mix as they exit the openings or apertures spaced along the length of the diffusing manifold.

Figure 4D:
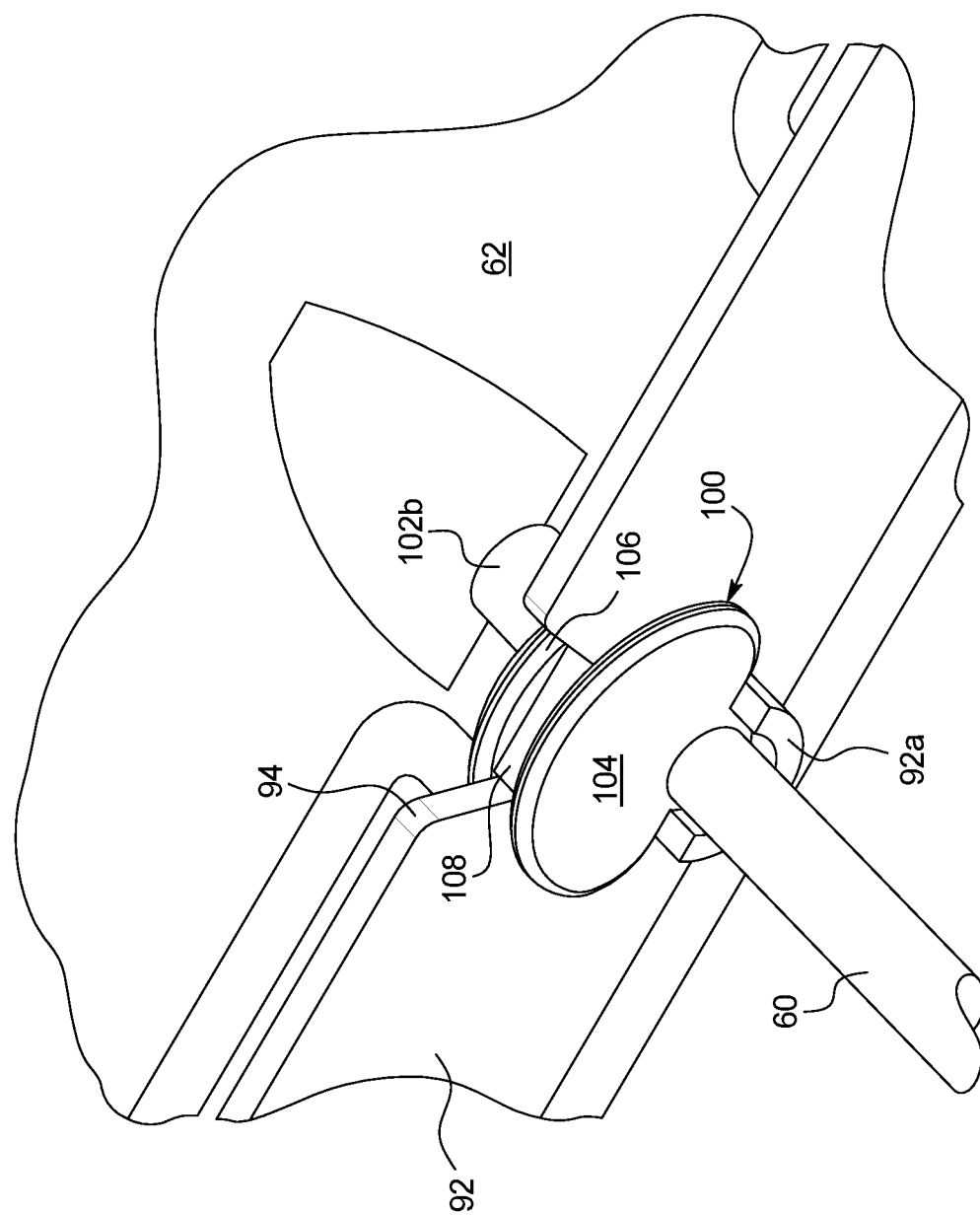
Figure 4E:
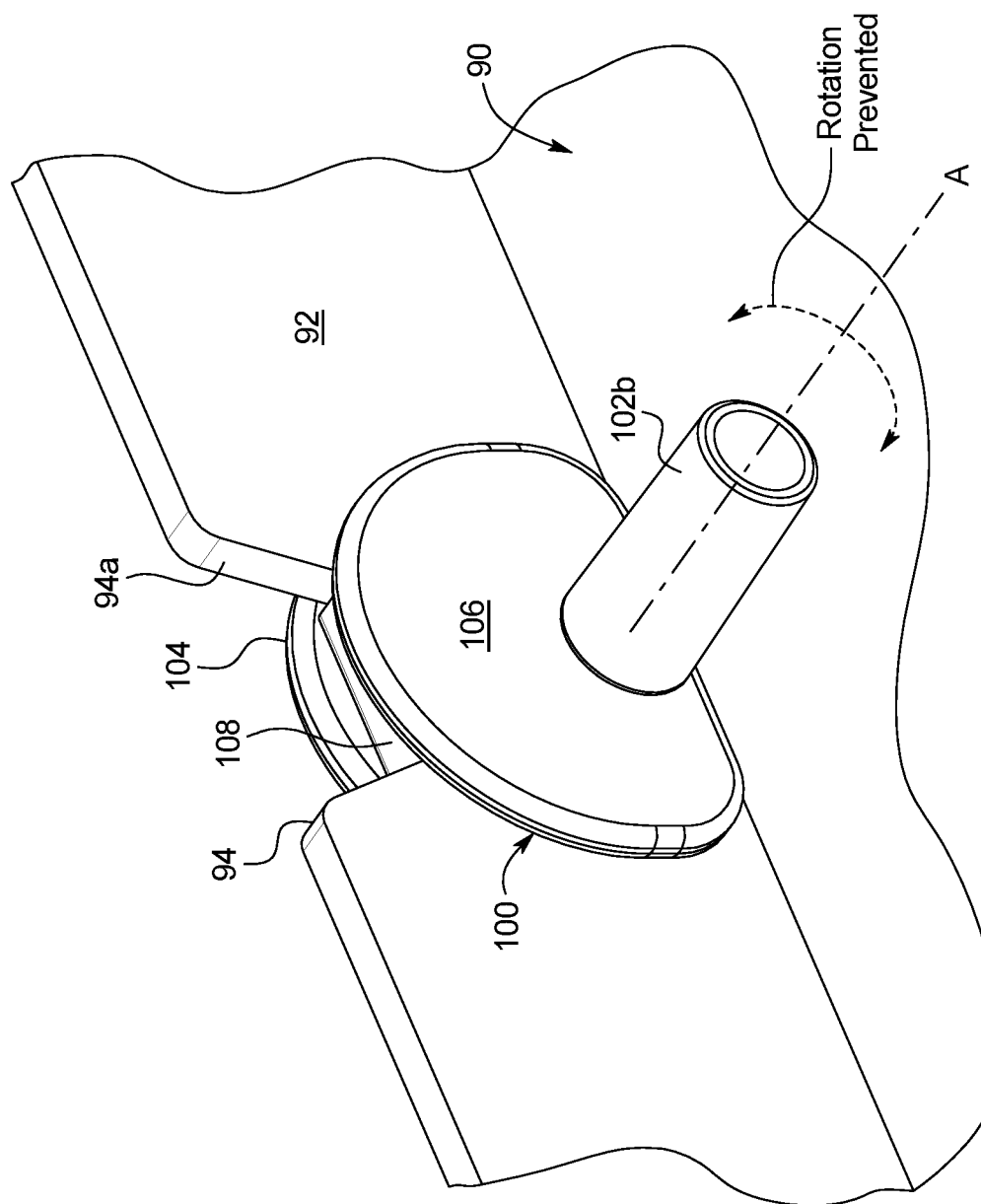

FIGS. 4D and 4E illustrate heater/mixing bag connector 100 inserted into slot 94 of sidewall 92. FIG. 4D shows heater/mixing bag connector 100 from the outside of heater pan 90, highlighting outer flange 104, while FIG. 4E shows heater/mixing bag connector 100 from the inside of heater pan 90, highlighting inner flange 106. In FIG. 4D, a bottom 104a (FIG. 4C) of outer flange 104 of heater/mixing bag connector 100 is bottomed out against semi-circular flange 92a extending from sidewall 92. FIGS. 4D and 4E show that outer flange 104 and inner flange 106 of heater/mixing bag connector 100 are abutted against outer and inner surfaces, respectively, of sidewall 92. Anti-rotation key 108 resides within slot 94 as illustrated in more detail below. Introduction port 102b of heater/mixing bag connector 100 is illustrated as being sealed to a section of heater/mixing bag 62. Tube connection port 102a of heater/mixing bag connector 100 is not viewable in FIG. 4D because it is covered by and sealed to heater/mixing line 60.

Outer flange 104 and inner flange 106 prevent heater/mixing bag connector 100 from being rotated about an axis perpendicular to the central axis A (FIG. 4E) through tube connection port 102a when heater/mixing bag 62 is being filled with concentrates and WFPD for heating and mixing. As discussed above, the concentrates are heavier than the WFPD. Thus, if heater/mixing bag connector 100 is rotated such that the distal end of introduction port 102b is pointed up towards the top of heater/mixing bag 62 during filling, the lighter water can flow over the heavier and falling concentrate, tending to prevent proper mixing. Outer flange 104 and inner flange 106 prevent such rotating and tilting from occurring, helping to ensure that the concentrates and WFPD are injected straight across the inside of heater/mixing bag 62, towards the far side of the bag 62.

Figure 4F:
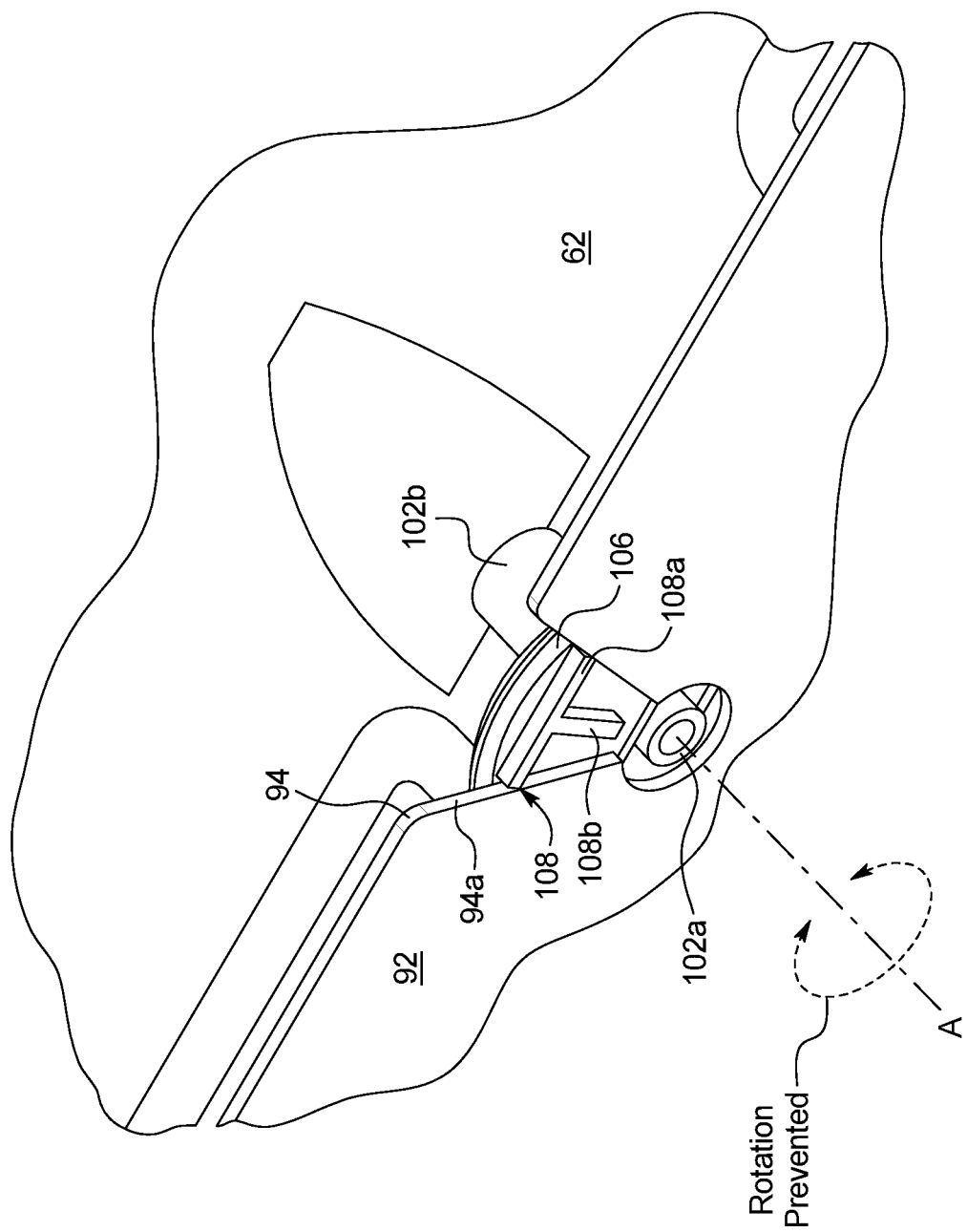

In FIG. 4F, outer flange 104 shown in FIG. 4D has been removed so that anti-rotation key 108 may be seen in full. FIG. 4F illustrates an internal section of heater/mixing bag connector 100 to highlight anti-rotation key 108, which resides within V-shaped section 94a of slot 94 when heater/mixing bag 62 is loaded into heater/mixing tray 90. As illustrated, anti-rotation key 108 includes an upper horizontal member 108a and a vertical, centrally located member 108b, forming a "T" shape. Upper horizontal member 108a extends to each edge of V-shaped section 94a, preventing the rotation of heater/mixing bag connector 100 in either a clockwise or counterclockwise direction about the central axis A (FIG. 4F) through tube connection port 102a. Centrally located vertical member 108b adds rigidity to heater/mixing bag connector 100. Anti-rotation key 108 serves the additional purpose of preventing heater/mixing bag 62 from being loaded upside down into heater/mixing tray 90. If patient P or another user attempts to load heater/mixing bag 62 upside down into heater/mixing tray 90, upper horizontal member 108a becomes wedged within V-shaped section 94a of slot 94, so that tube connection port 102a cannot snap-fit into circular section 94b of slot 94. Patient P or other user senses the improper fit and reloads heater/mixing bag 62 in the proper orientation within heater/mixing tray 90.

FIG. 4G illustrates that once patient P or other user loads heater/mixing bag 62 properly into heater/mixing tray 90, patient P or other user closes (e.g., hingedly closes) lid 96, such that sidewall 98 of lid 96 meets sidewall 92 of heater/mixing tray 90. In the illustrated embodiment, lid 96 is sized and positioned such that when lid is closed, the bottom edge 98a of sidewall 98 closes onto outer flange 104 of heater/mixing bag connector 100. This closure, along with the snap-fitting of tube connection port 102a into circular section 94b of slot 94 prevents the upward vertical translation or displacement of heater/mixing bag connector 100 within slot 94, e.g., due to the filling of heater/mixing bag 62 with concentrates and WFPD.

In an alternative embodiment (not illustrated), the heater/mixing bag connector is configured such that patient P or other user loads the port into slot 94 as before. Patient P or the other user then rotates the port, e.g., 45° clockwise, until a handle provided by the port is approximately horizontal, which in turn orients internal diameter ribs of the alternative connector residing within circular section 94b of slot 94, such that the ribs abut the wall of resting circular section 94b to resist vertical displacement of the alternative port within slot 94 during the filling of heater/mixing bag 62.

Heater/mixing bag connector 100 or the alternative heater/mixing bag connector just described, including any alternative embodiments described in connection with FIGS. 4A to 4G, may be used for any of the different dialysis systems 10a to 10d having point of use dialysis fluid preparation described herein.

Mixing Regime, Dialysis Fluid Testing, and Treatment

Figure 5:
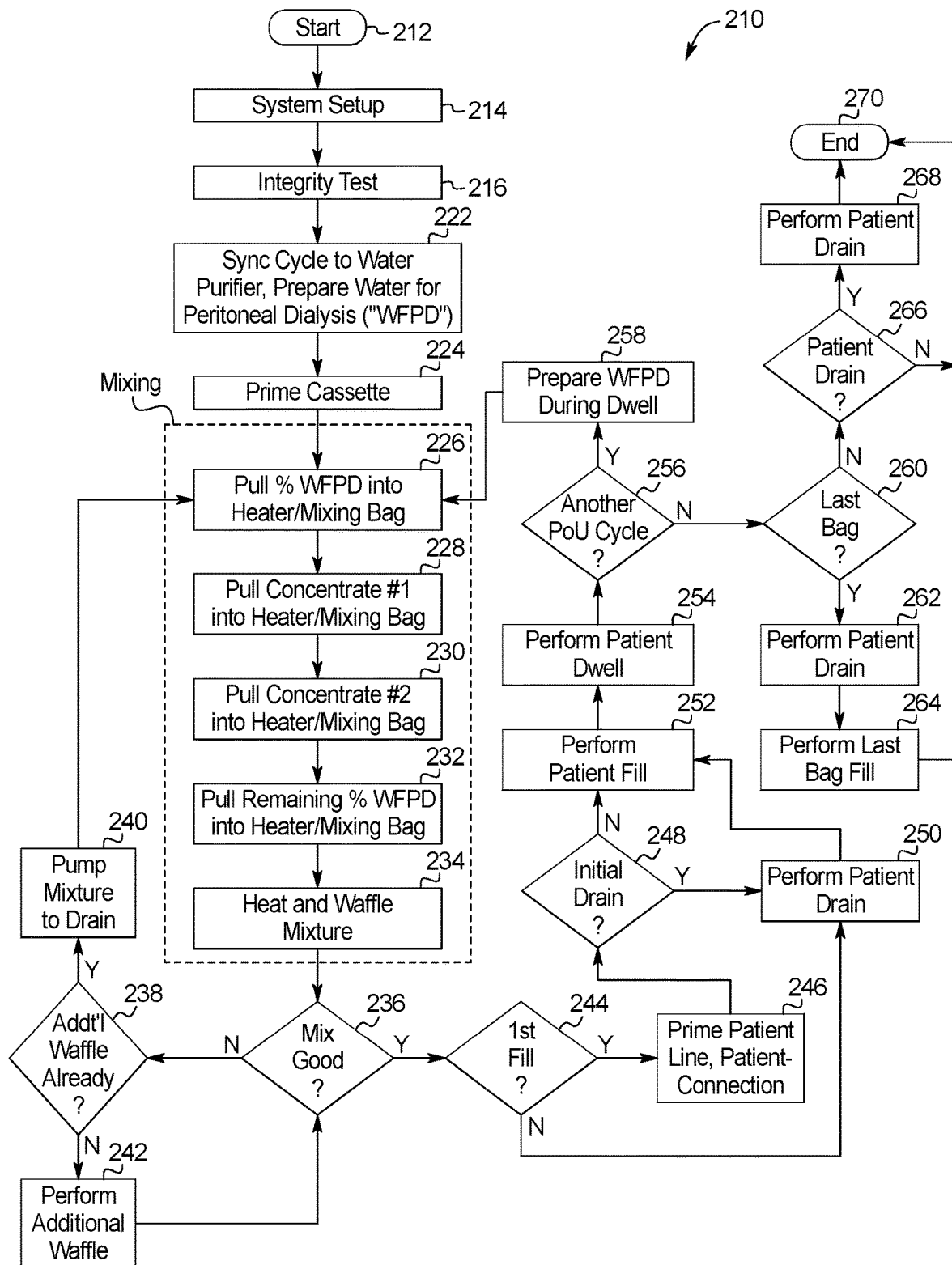
FIG. 5 is a process flow diagram illustrating one dialysis fluid mixing, dialysis fluid testing, and treatment method suitable for use with the system illustrated in FIG. 1.

Referring now to FIG. 5, one embodiment for mixing dialysis fluid at the point of use using multiple concentrates and WFPD is illustrated by method 210. At oval 212, method 210 begins. At block 214, patient P or other user performs setup for system 10 as discussed above, including (i) turning cycler 20 on, (ii) placing heater/mixing bag 62 onto cycler 20, (iii) connecting upstream water line segment 64a to water purifier 110, (iv) connecting drain line 56 to water purifier 110, (v) connecting first cassette concentrate connector 80a to first container concentrate connector 80b, and (vi) and connecting second cassette concentrate connector 82a to second container concentrate connector 82b.

At block 216, cycler 20 performs dry integrity tests which pressure check cassette 42, water accumulator 66 and heater/mixing bag 62, for example. At block 222, after determining that disposable set 40 passes the integrity tests, control unit 22 may turn water purifier 110 on automatically, sync wirelessly with its control unit 112, and tell control unit to prepare WFPD, e.g., specifying volume and temperature. To prepare WFPD, in one embodiment viewing FIG. 1, control unit 112 of water purifier 110 causes the water purifier to pump purified water at a desired pressure set by pressure regulator 130, at a desired temperature, e.g., at 20° C. to 30° C., through sterile sterilizing grade filters 70a and 70b, and through upstream water line segment 64a into water accumulator 66 via water inlet 66a. Pressure regulator 130 may set the water outlet pressure to on the order of 137.9 to 275.8 kPa (20 to 40 psig) to force purified water through sterile sterilizing grade filters 70a and 70b to produce WFPD residing within water accumulator 66. Water purifier 110 may for example pump 2 to 3 liters of purified water at 20° C. to 30° C. through sterile sterilizing grade filters 70a and 70b to water accumulator 66. Up until block 216, cycler 20 is not needed for fluid control, other than to close the fluid valve chamber 46 at cassette 42 to downstream water line segment 64b and/or close occluder 26 at patient line 50 and drain line 56, because water accumulator 66 decouples or isolates water purifier 110 from disposable set 40 in terms of fluid pressure and flowrate. It should be appreciated, however, that control unit 22 of cycler 20 may initiate the preparation of WFPD by sending a command wired or wirelessly to control unit 112 of water purifier 110 to prepare a desired quantity of WFPD at a certain temperature. The elevated temperature of WFPD lowers the heating burden on cycler 20.

At block 224, control unit 22 causes cycler 20 to perform a cassette 42 prime sequence. To prime cassette 42, control unit 22 causes cycler 20 to open fluid valves 46 at cassette 42 to (i) first concentrate container line 86 and (ii) drain line 56, allowing pump chambers 44 to prime (e.g., alternatingly to achieve somewhat continuous flow) first concentrate line 76/86 with first concentrate from first concentrate container 84a, pushing air in those lines to drain 116. Control unit 22 then causes cycler 20 to (i) close cassette fluid valve 46 to first concentrate line 76/86, (ii) maintain cassette fluid valve 46 to drain line 56 open, and (iii) open fluid valve 46 at cassette 42 to second concentrate line 78/88, allowing pump chambers 44 to prime (e.g., alternatingly to achieve somewhat continuous flow) second concentrate line 78/88 with second concentrate from second concentrate container 84b, pushing air from those lines to drain 116. Control unit 22 then causes cycler 20 to (i) close cassette fluid valve 46 to second concentrate line 78/88, (ii) maintain cassette fluid valve 46 to drain line 56 open, and (iii) open the fluid valve chamber 46 to downstream water line segment 64b, allowing fluid pump chambers 44 to prime (e.g., alternatingly to achieve somewhat continuous flow) line segment 64b and drain line 56 with WFPD from water accumulator 66, pushing air from those lines to drain 116.

Initially, drain line 56 will be filled with a combination of WFPD and concentrates due to the priming of concentrate lines 76/86 and 78/88 with concentrate. At priming block 224, or at some other step prior to testing the mixed dialysis fluid, control unit 22 causes cycler 20 to pump enough WFPD from water accumulator 66 so that drain line is primed completely with WFPD, and so that WFPD is flowed to a conductivity sensor 132. When WFPD is at conductivity sensor 132, control unit 112 of water purifier 110 may take one or more conductivity reading from conductivity sensor 132 for the WFPD and either (i) compare the reading(s) with an expected reading for WFPD and send, wired or wirelessly, a "conductivity sensor reading good" or "conductivity sensor reading fails" output to control unit 22 of cycler 20, which takes appropriate action, or (ii) sends the conductivity reading(s) wired or wirelessly to control unit 22 of cycler 20, so that control unit 22 may determine, e.g., compare the reading to a look-up table, if the conductivity sensor reading is good or not and take appropriate action. The above calibration procedure may be performed using any one or more fluid having a known conductivity.

At block 226 mixing begins, wherein control unit 22 causes cycler 20 to (i) close the fluid valve 46 of cassette 42 leading to drain line 56, (ii) open the fluid valve 46 of cassette 42 leading to downstream water line segment 64b and (iii) open the fluid valve 46 of cassette 42 leading to heater/mixing bag 62, allowing fluid pump chambers 44 to pump (e.g., alternatingly to achieve somewhat continuous flow) a desired amount of WFPD from water accumulator 66, through downstream water line segment 64b, through cassette 42, through heater/mixing line 60 and into heater/mixing bag 62 via heater/mixing bag connector 100. In one embodiment, the initial desired amount of WFPD is a percentage of a total desired amount of WFPD, which is based on the prescribed patient fill volume plus an additional volume, e.g., 300 to 500 milliliters over the prescribed fill volume. One suitable percentage is ten percent.

At block 228, control unit 22 causes cycler 20 to (i) close the fluid valve chamber 46 at cassette 42 to downstream water line segment 64b, (ii) maintain open the fluid valve chamber 46 at cassette 42 to heater/mixing bag 62, and (iii) open the fluid valve chamber 46 at cassette 42 to first, e.g., glucose, concentrate line 76/86, allowing fluid pump chambers 44 to pump (e.g., alternatingly to achieve somewhat continuous flow) a desired amount of first concentrate, e.g., glucose, from first concentrate container 84a, through first concentrate line 76/86, through cassette 42, through heater/mixing line 60 and into heater/mixing bag 62 via heater/mixing bag connector 100. In one embodiment, the desired amount of first concentrate, e.g., glucose, is a total desired amount of first concentrate, which is based on the prescribed patient fill volume (plus an extra 300 to 500 milliliters of margin) and the prescribed dialysis fluid chemistry. Example approved dialysis fluid chemistries include (i) 1.5% dextrose monohydrate (or glucose monohydrate)=1.36% anhydrous dextrose (or anhydrous glucose), (ii) 2.5% dextrose monohydrate (or glucose monohydrate)=2.27% anhydrous dextrose (or anhydrous glucose), and (iii) 4.25% dextrose monohydrate (or glucose monohydrate)=3.86% anhydrous dextrose (or anhydrous glucose).

At block 230, control unit 22 causes cycler 20 to (i) close the fluid valve chamber 46 at cassette 42 to first concentrate line 76/86, (ii) maintain open the fluid valve chamber 46 at cassette 42 to heater/mixing bag 62, and (iii) open the fluid valve chamber 46 at cassette 42 to second, e.g., buffer, concentrate line 78/88, allowing fluid pump chambers 44 to pump (e.g., alternatingly to achieve somewhat continuous flow) a desired amount of second concentrate, e.g., buffer, from second concentrate container 84b, through second concentrate line 78/88, through cassette 42, through heater/mixing line 60 and into heater/mixing bag 62 via heater/mixing bag connector 100. In one embodiment, the desired amount of second concentrate, e.g., buffer, is a total desired amount of second concentrate, which is again based on the prescribed patient fill volume (plus an extra 300 to 500 milliliters of margin) and the prescribed dialysis fluid chemistry.

At block 232, control unit 22 causes cycler 20 to (i) close the fluid valve chamber 46 at cassette 42 to second concentrate line 78, (ii) maintain open the fluid valve chamber 46 at cassette 42 to heater/mixing bag 62, and (iii) open the fluid valve chamber 46 at cassette 42 to downstream water line segment 64b, allowing fluid pump chambers 44 to pump (e.g., alternatingly to achieve somewhat continuous flow) the remaining amount, e.g., ninety percent, of WFPD from water accumulator 66, through downstream water line segment 64b, through cassette 42, through heater/mixing line 60 and into heater/mixing bag 62 via heater/mixing bag connector 100. At this point the correct amounts of WFPD, first concentrate, e.g., glucose, second concentrate, e.g., buffer, and . . . nth concentrate (method 210 is scalable for any desired number of concentrates, including only a single concentrate) to prepare the prescribed amount of the prescribed peritoneal dialysis solution. The prescribed amount will reside within heater/mixing bag 62 and cassette 42. That is, in one embodiment pumping the remaining percentage of WFPD ends when the final pump stroke of water reaches one of the fluid pump chambers 44.

At block 234, control unit 22 causes cycler 20 to (i) turn on the fluid heater within housing 24 to heat the WFPD and concentrates within heater/mixing bag 62 (although heating may begin earlier as long as there is some type of fluid within heater/mixing bag 62) and (ii) perform a "waffling" sequence. To perform the waffling sequence, control unit 22 in an embodiment causes cycler 20 to close all fluid valve chambers 46 at cassette 42 except for the fluid valve chamber 46 to heater/mixing line 60 and heater/mixing bag 62. Fluid pump chambers 44 are stroked sequentially and repeatedly to (i) pull WFPD and concentrates from heater/mixing bag 62 into the pump chambers and (ii) push WFPD and concentrates from the pump chambers to heater/mixing bag 62. Control unit 22 may be programmed to stroke fluid pump chambers 44 together so that they both pull and push at the same time, or alternatingly so that one pump chamber 44 pulls from heater/mixing bag 62, while the other pump chamber 44 pushes to heater/mixing bag 62, creating turbulence in heater/mixing line 60.

In an alternative waffling embodiments, control unit 22 is programmed to cause the first and second pump chambers 44 to pump to each other one or more time before pushing fluid back to heater/mixing bag 62. Additionally, to further create turbulence, it is contemplated in any of the waffling embodiments to program control unit 22 to cause the electrical input signal to one or more variable orifice pneumatic valve for pump chambers 44 to vary during the waffling sequence, e.g., in a pulse, cyclic or sinewave like manner, such as 3.5 kPa (0.5 psig) up and down from a mean pumping pressure, such as 24.8 kPa (3.6 psig). Moreover, for any of the waffling embodiments, it is contemplated to pump from and to heater/mixing bag 62 until, for example, 200 percent of the heater/mixing bag volume is pumped back and forth. The 200 percent or other desired percentage may be achieved within the time needed to properly heat the mixed dialysis fluid to, e.g., 35° C. to 37° C.

At diamond 236 after waffling, and remembering that drain line 56 is primed with WFPD, control unit 22 causes cycler 20 to close all fluid valve chambers 46 at cassette 42 except for the fluid valve chamber 46 to drain line 56, allowing fluid pump chambers 44 to pump (e.g., alternatingly to achieve somewhat continuous flow) a desired sample amount, e.g., 80 to 100 milliliters, of fresh mixed dialysis fluid down drain line 56 to conductivity sensor 132 to take one or more conductivity reading of the of fresh, mixed dialysis fluid. In an embodiment, control unit 22 is programmed to cause cycler 20 to then pump WFPD down drain line 56 to conductivity sensor 132 after the, e.g., 80 to 100 milliliters, slug of mixed dialysis solution to provide a clear conductivity sensing differentiation both before and after the slug. To provide the after-slug WFPD, control unit 22 is programmed in one embodiment to (i) close the cassette fluid valve 46 leading to heater/mixing line 60, open the cassette fluid valve 46 leading to downstream water line segment 64b and water accumulator 66, open the cassette fluid valve 46 leading to drain line 56, allowing fluid pump chambers 44 to pump (e.g., alternatingly to achieve somewhat continuous flow) a desired amount of WFPD from water accumulator 66, through downstream water line segment 64b, through cassette 42, down drain line 56 to conductivity sensor 132.

Different PD dialysis fluids are typically differentiated by dextrose or glucose levels. For example, there is a 4.25% dextrose monohydrate (or glucose monohydrate)=3.86% anhydrous dextrose (or anhydrous glucose) PD dialysis fluid. 4.25% dextrose may, depending on its chemical formulation, have a corresponding and repeatable conductivity measurement of 11.64 mS/cm. The other two common dialysis fluid types (1.5% dextrose and 2.5% dextrose) produce different corresponding and repeatable conductivity measurements. Control unit 22 can therefore verify if the dialysis fluid has been mixed properly by comparing its measured conductivity to an expected conductivity stored in a look-up table.

As part of block 234, and as described similarly at block 224, when conductivity sensor 132 reads the slug of freshly mixed dialysis fluid, control unit 112 of water purifier 110 takes one or more conductivity reading from conductivity sensor 132 for the mixed dialysis fluid slug and either (i) compares the reading(s) with an expected reading for WFPD and sends, wired or wirelessly, a "mixed dialysis fluid reading good" or "mixed dialysis fluid reading failed" output to control unit 22 of cycler 20 which takes appropriate action, or (ii) sends the conductivity reading(s) wired or wirelessly to control unit 22 of cycler 20, so that control unit 22 may determine, e.g., compare the reading to a look-up table, if the mixed dialysis fluid reading(s) is good or not. The comparison may be to a range, e.g., within five percent of the setpoint conductivity.

If the result at diamond 236 is that the measured dialysis fluid is outside the range of the setpoint conductivity, method 210 at diamond 238 inquires whether an additional amount of waffling has already been performed. If an additional amount of waffling has already been performed as determined at diamond 238, control unit 22 of cycler 20 at block 240 causes the current batch of mixed dialysis fluid to be sent to drain 116 and performs the mixing process again, starting at block 226. If an additional amount of waffling has not yet been performed as determined at diamond 238, control unit 22 of cycler 20 at block 242 causes an additional amount of waffling to occur, wherein another 50 percent of the heater/mixing bag volume, for example, is pumped back and forth, after which method 210 returns to diamond 236 to test the additionally waffled dialysis fluid again. In one embodiment, preceding the additional waffling at block 238, control unit 22 may cause a second sample of mixed dialysis fluid to be sent to conductivity sensor 132 for re-measurement (in case of an erroneous measurement in the first sample, e.g., due to air).

Figure 16:
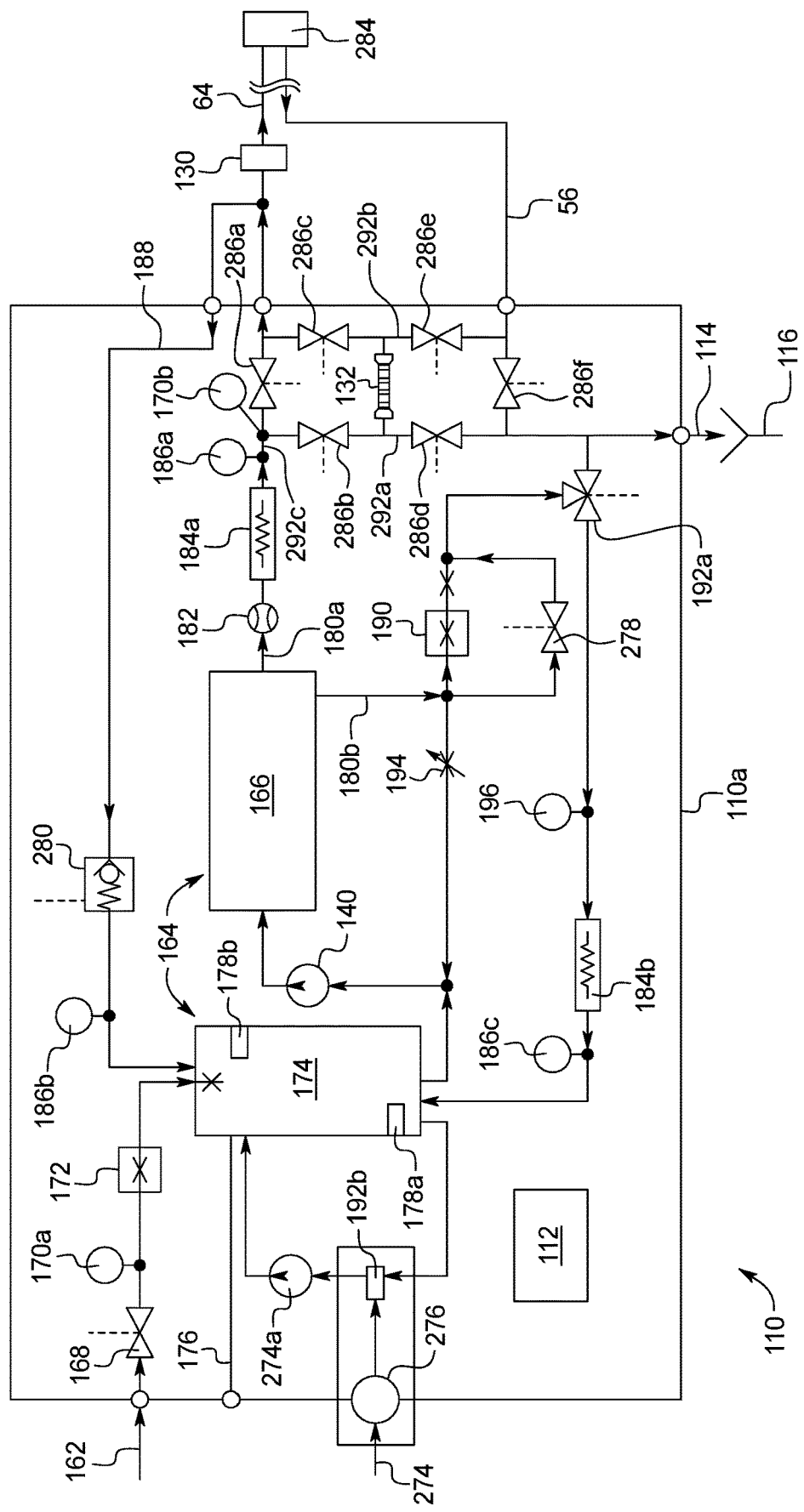
FIG. 16 is a schematic view of one embodiment of a water purifier that may be used with any of the peritoneal dialysis systems having point of use dialysis fluid production discussed herein.

It should be appreciated that when conductivity sensor 132 is not used for sampling, the sensor may be bypassed so it is not used at all or be used for a different purpose, e.g. in water purifier 110 to sample the conductivity of water being purified. FIG. 16 illustrates various embodiments for providing this functionality. FIG. 16 illustrates conductivity sensor surrounded by six valves 286a to 286e, which may be electrically actuated solenoid valves (e.g., normally closed, energized open) under the control of control unit 112. In a normal draining operation, when mixed fluid sample testing is not desired, control unit 112 causes valves 286b, 286c, 286d and 286e provided in parallel flow paths or lines 292a and 292b to be closed and valve 286f to be open, so that used dialysis fluid, WFPD, unused concentrate or combinations thereof may flow through drain line 56, valve 286f, to drain 116 at water purifier 110. Here, conductivity sensor 132 is bypassed completely and valve 286a may be opened or closed to allow or not allow purified water to flow out water line 64 as desired. Alternatively during a draining operation, when mixed fluid sample testing is not desired, control unit 112 causes (i) valves 286d and 286e to be closed and valve 286f to be open so that used dialysis fluid, WFPD, unused concentrate or combinations thereof may flow through drain line 56, valve 286f, to drain 116 at water purifier 110 and (ii) valve 286a to be closed and valves 286b and 286c to be open so that purified water flows past conductivity sensor 132 for sensing. It should be appreciated that control unit 112 may control valve 286a to be closed and valves 286b and 286c to be open to test the purified water output regardless of whether or not effluent is flowing through drain line 56 to drain 116. When mixed fluid sampling is desired, control unit 112 causes valves 286b, 286c and 286f to be closed and valves 286d and 286e to be open so that the mixed fluid sample flows past conductivity sensor 132 to drain. Here, valve 286a may be open or closed to allow or not allow purified water to flow through main water line 292c.

In an alternative embodiment, valve 286a is not provided and conductivity sensor 132 is moved to where valve 286a is located in FIG. 16, so that conductivity sensor 132 may replace downstream conductivity sensor 170b. Valves 286b and 286c are moved outside of the connections of parallel lines 292a and 292b to main water line 292c, so that control unit 112 can selectively allow conductivity sensor 132 to sense purified water flowing through main water line 292c. When valves 286b and 286c are closed, control unit 112 may close valve 286f and open valves 286d and 286e, so that sample mixed fluid may flow past conductivity sensor 132 to drain. In this alternative embodiment, sample mixed fluid may not flow past conductivity sensor 132 to drain when purified water is flowing through main water line 292c. Also, all purified water flowing through main water line 292c sees conductivity sensor 132, so that selective sampling of purified water flowing through main water line 292c is not possible.

Returning to method 210, if the result at diamond 236 is that the measured dialysis fluid is within the range of the setpoint conductivity, method 210 proceeds with treatment. Here, at diamond 244, control unit 22 of cycler 20 determines if the upcoming fill procedure for patient P is a first fill procedure for the current treatment. If so, at block 246, control unit 22 causes cycler 20 to open the fluid valve 46 of cassette 42 to patient line 50 and prime patient line 50 up to patient connector 52 with properly mixed dialysis fluid. Patient connector 52 may for example be fitted with a tip protector having a hydrophobic membrane that allows air to be pushed through the membrane by the properly mixed dialysis fluid filling patient line 50. Once patient line 50 is primed, user interface 30 prompts patient P to connect patient connector 52 to the patient P's transfer set 54, leading to patient P's indwelling catheter.

At diamond 248, control unit 22 determines if patient P is already full with used dialysis fluid. Control unit 22 and user interface 30 of cycler 20 may, for example, query patient P during treatment setup whether or not an initial drain is needed. If so, or if the upcoming fill procedure is not the first fill procedure as determined at diamond 244 (meaning patient P already has a fill volume plus an amount of ultrafiltration removed), method 210 performs a drain procedure for patient P at block 250. At block 250, control unit 22 causes cycler 20 to (i) maintain fluid valve 46 of cassette 42 to patient line 50 open and (ii) open the fluid valve 46 of cassette 42 to drain line 56, allowing fluid pump chambers 44 to pump (e.g., alternatingly to achieve somewhat continuous flow) used dialysis from the patient's peritoneum to drain 116 (either full drain for continuous cycling peritoneal dialysis ("CCPD") or a partial drain for a tidal PD treatment, whichever is prescribed), recording the drained amount for purposes of determining ultrafiltration removed over the previous twenty-four hours (assuming consecutive treatments start at the same time of the night).

At diamond 248, if patient P does not have used dialysis fluid to initially drain, or when the drain at block 250 is completed, method 210 performs a fill procedure for patient P at block 252. At block 252, control unit 22 causes cycler 20 to (i) maintain fluid valve 46 of cassette 42 to patient line 50 open and (ii) open the fluid valve 46 of cassette 42 to heater/mixing line 60, allowing fluid pump chambers 44 to pump (e.g., alternatingly to achieve somewhat continuous flow) properly mixed fresh dialysis fluid from heater/mixing bag 62 to patient P. The amount of properly mixed fresh dialysis fluid pumped is prescribed by a doctor or clinician. As discussed above, control unit 22 is programmed in one embodiment to prepare a greater amount of fresh dialysis fluid for storage in heater/mixing bag 62 than is delivered to patient P during the fill procedure, e.g., 2.5 liters when only 2 liters is pumped to the patient. There is accordingly likely to be some amount of fresh dialysis fluid, e.g., 500 milliliters, residing within heater/mixing bag 62 after the fill procedure.

At block 254, method 210 preforms a patient dwell procedure. During the dwell procedure, control unit 22 causes cycler 20 to close the fluid valve 46 of cassette 42 to patient line 50. The therapeutic effect of the newly mixed fresh dialysis fluid takes place during the dwell phase. Waste and toxins move osmotically from the blood of patient P, through patient P's peritoneal membrane, into the dialysis fluid. Excess fluid from patient P is also removed into the dialysis fluid as ultrafiltration ("UF"), typically seven percent of the fill volume, so roughly 140 milliliters for a 2 liter fill volume). The dwell period at block 254 may last one to two hours, for example.

At diamond 256, control unit 22 determines whether there is another point of use preparation cycle for the current treatment. If so, at block 258, control unit 22 causes cycler 20, during the dwell period, to instruct water purifier 110 to prepare another batch, e.g., 2 to 3 liters, of WFPD and deliver the batch at a desired temperature to water accumulator 66. Preparing WFPD at block 258 may be done according the valving procedure described in connection with block 222. Also, because water accumulator 66 decouples cycler 20 from water purifier 110 in terms of fluid flow and pressure, the procedure of block 258 does not have to wait until the dwell period and may in alternative embodiments begin during the patient fill procedure at block 252 or even at the patient drain procedure at block 250, providing additional time to prepare the next batch of dialysis fluid, which occurs during the dwell procedure, starting at block 226 and running through the mixing steps to block 234.

It should also be appreciated that control unit 22 knows how much WFPD resides in water accumulator 66 at any given time because it knows how much it told water purifier 110 to send to accumulator 66 and how much it caused cycler 20 to pump from accumulator 66. To not overfill water accumulator 66, control unit 22 is accordingly programmed to calculate how much additional WFPD is needed at block 258, which in combination with any residual WFPD residing in water accumulator 66 sums to a desired overall amount of WFPD in the accumulator.

Similarly, as discussed above, there is likely to be residual fresh dialysis fluid in heater/mixing bag 62 when the second, third, fourth, etc., batch of dialysis fluid is made at mixing steps 226 to 234. Control unit 22 knows how much dialysis fluid was delivered to heater/mixing bag 62 in the previous mixing and heating procedure and how much of that dialysis fluid was delivered to patient P at the previous fill procedure at block 252. Control unit 22 therefore knows how much residual properly mixed dialysis fluid remains in heater/mixing bag 62 and calculates how much new dialysis fluid to mix with the residual fluid to achieve the same desired extra amount, e.g., 300 to 500 milliliters. So for example, if 2.5 liters of fresh dialysis fluid were prepared initially in heater/mixing bag 62 and 2 liters were delivered to patient P in the previous fill, control unit 22 the next time around prepares only 2 liters of new dialysis fluid to reach the same desired 2.5 liters (including desired 500 milliliter margin) in heater/mixing bag 62 prior to the next patient fill procedure.

It is contemplated that a doctor or clinician may prescribe different dextrose or glucose levels for different patient fill procedures of the same treatment. For example, a first fill may be prescribed to use 1.5% dextrose monohydrate dialysis fluid, while a second fill uses 2.5% dextrose monohydrate dialysis fluid, and a third fill uses 4.25% dextrose monohydrate dialysis fluid. When this is done, and when there is a residual volume of dialysis fluid within heater/mixing bag 62 at a dextrose level different from what is prescribed for the current batch of dialysis fluid, control unit 22 may be programmed to cause cycler 20 perform any one of the following: (i) pump the residual dialysis fluid to drain 116 and prepare a new batch of dialysis fluid plus any desired surplus at the prescribed dextrose or glucose level, (ii) keep the residual dialysis fluid and prepare a new batch of dialysis fluid in an amount to maintain the desired surplus and at the prescribed dextrose or glucose level, knowing that the resulting mixture will be different than the prescribed dextrose or glucose level due to the residual dialysis fluid having the different dextrose or glucose level, or (iii) keep the residual dialysis fluid and prepare a new batch of dialysis fluid in an amount to maintain the desired surplus and at a dextrose or glucose level that in combination with the residual dialysis fluid having the different dextrose or glucose level will meet the prescribed dextrose or glucose level. Option (ii) is acceptable because the resulting dextrose or glucose level will be in a physiologically safe range for patient P, e.g., at or between the regulatorily accepted 1.5% to 4.25% dextrose monohydrate dialysis fluid levels. In an embodiment, the look-up table within control unit 22 or control unit 112 is programmed to store setpoint conductivity values for expected combinations, e.g., for a situation in (ii) where 500 milliliters of 1.5% dextrose monohydrate dialysis fluid is combined with 2 liters of 2.5% dextrose monohydrate dialysis fluid. Setpoint conductivity values for expected combinations also includes combinations that occur when a doctor or clinician prescribes an optimized, physiologically safe dextrose or glucose level for patient P, e.g., at or between the regulatorily accepted 1.5% to 4.25% dextrose monohydrate dialysis fluid levels.

If there is no additional point of use preparation cycle for the current treatment as determined at diamond 256, control unit at diamond 260 determines if patient P's treatment prescription calls for a last bag fill for patient P. The last bag is connected to connector 74 for the last bag or sample line 72 in one embodiment. The last bag typically includes a premixed and sterilized dialysis fluid having a higher dextrose or glucose level and a chemical formulation that cannot be prepared using the first and second concentrates in first and second concentrate containers 84a and 84b.

If there is a last bag fill for patient P, as determined at diamond 260, control unit 22 at block 262 causes cycler 20 to perform a patient drain, e.g., according to the drain valving sequence discussed at block 250. Control unit 22 at block 264 then causes cycler 20 to perform a patient fill using last bag dialysis fluid from the last bag connected to connector 74 and the fill valving procedure described at block 252 in one embodiment. After the last bag fill, method 210 ends at oval 270.

If there is not a last bag fill for patient P, as determined at diamond 260, control unit 22 at diamond 266 determines whether patient P's prescription calls for patient P to end treatment dry or with the last fill volume remaining in patient P's peritoneal cavity. That is, control unit 22 determines whether there is a final patient drain procedure or not. If not, treatment ends at oval 270. If so, control unit 22 at block 262 causes cycler 20 to perform a patient drain, e.g., according to the drain valving sequence discussed at block 250. After the final drain, method 210 ends at oval 270.

At the end of treatment at oval 270, control unit 22 is programmed in one embodiment to cause cycler 20 to pump as much remaining fresh dialysis fluid, used dialysis fluid, WFPD and concentrates to drain 116 as possible. Nevertheless, there will likely be some fluid remaining within disposable set 40. As described above, water line connector 68 and drain line connector 58 may be connected together at the end of treatment so that no fluid can spill out of those lines when disposable set 40 is removed from cycler 20 and water purifier 110.

In one alternative embodiment to method 210, when patient P is prescribed a relatively low fill volume, e.g., for a pediatric treatment, control unit 22 may be programmed to cause cycler 20 to prepare multiple fill volumes worth of dialysis fluid at once and store the multiple fill volumes plus perhaps an extra amount in heater/mixing bag 62. In such a situation, the steps of method 210 up to block 244 are the same. Afterwards, however, control unit is programmed to cause cycler 20 to perform at least one additional fill without the intermediate mixing steps set forth from block 226 to block 234.

Advantages of Water Accumulator

Water accumulator 66 provides many advantages, for example, the fluid flow and pressure decoupling of cycler 20 and water purifier 110 discussed above. Besides allowing WFPD to be made while cycler 20 is performing treatment, the pressure decoupling also protects cycler 20 and cassette 42 in a situation in which one or both sterile sterilizing grade filters 70a and 70b fail, which could allow the regulated operating pressure of water purifier 110 driving sterile sterilizing grade filters 70a and 70b to be seen downstream from the filters. If such pressure, e.g., 137.9 to 275.8 kPa (20 to 40 psig), were to reach cassette 42, which cycler 20 in various embodiments operates at pressures of up to only 48.3 kPa (7 psig) positive pressure and −34.5 kPa (−5 psig) suction pressure, closed cassette valves 46 would be forced open and pump chamber chambers 44 would be forced to an open end-of-stroke position. Cycler 20 would thereby become inoperable. Water accumulator 66 prevents this situation by providing a place to absorb the overpressure, providing enough time for water purifier 110 to sense a corresponding pressure drop and take appropriate action, such as entering a safe mode in which its pumps are shut down and an alert is sent wired or wirelessly to cycler 20, which in turn alarms audibly, visually or audio-visually at user interface 30.

Other advantages provided by water accumulator 66 include allowing sterile sterilizing grade filters 70a and 70b to be operated at lower pressures and to thus be more economical. Lower operating pressures within water purifier 110 also produces less wear on its components.

Alternative to Water Accumulator

Figure 6:
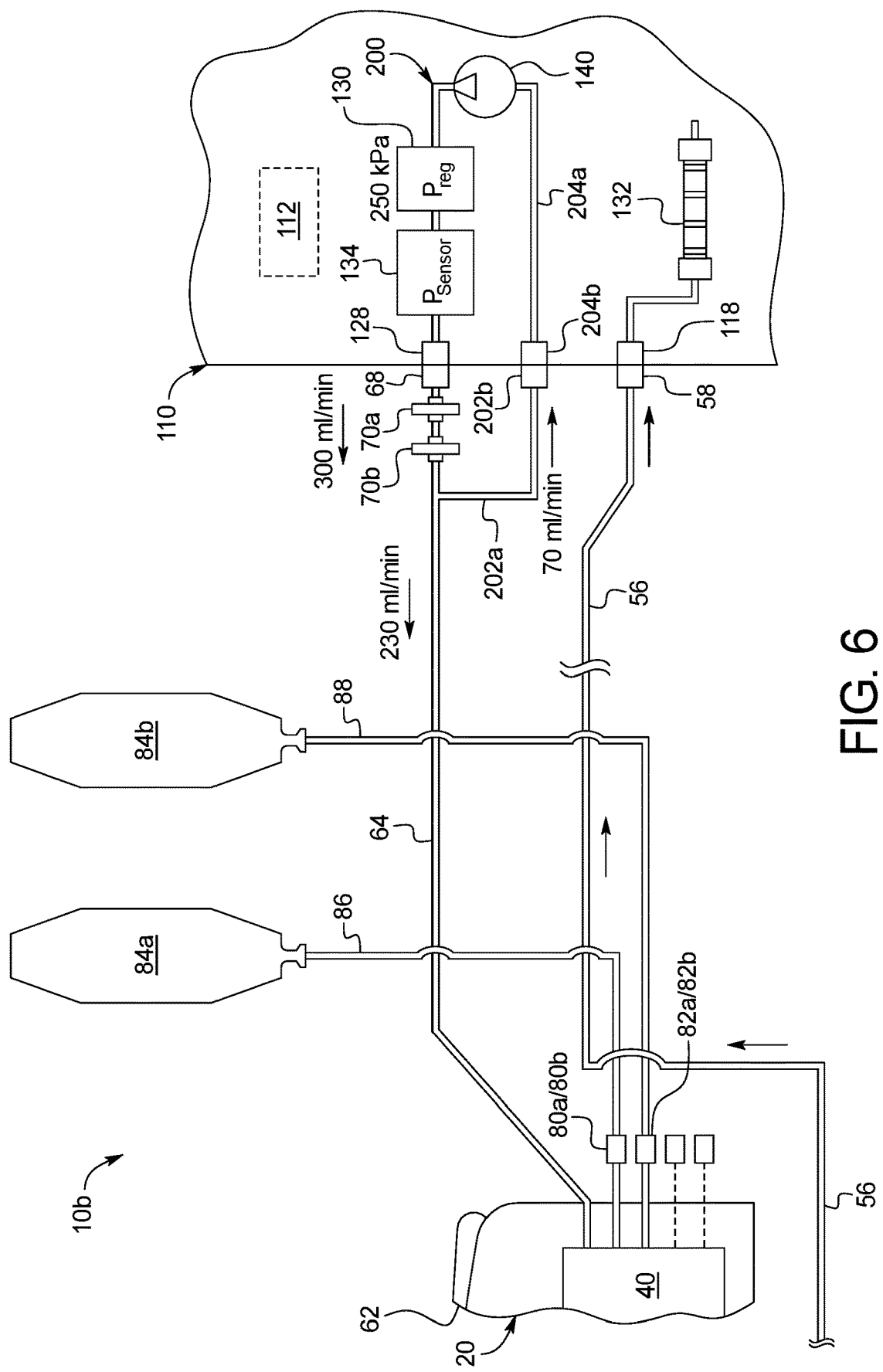
FIG. 6 is a front elevation view of another embodiment of a peritoneal dialysis system having point of use dialysis fluid production of the present disclosure.

Referring now to FIG. 6, one embodiment of an alternative dialysis system 10b having point of use dialysis fluid preparation is illustrated. System 10b has many of the same components as system 10a, and like elements, including all alternative embodiments discussed for such elements, are numbered the same. For ease of illustration, only a portion of cycler 20 and water purifier 110 are illustrated. The primary difference between systems 10a and 10b is that water accumulator 66 is not provided in system 10b. Instead, system 10b provides a recirculation loop 200 having a disposable portion including a disposable recirculation line 202a and a disposable recirculation connector 202b, and a water purifier portion including a water purifier recirculation line 204a and a water recirculation connector 204b.

Recirculation loop 200 is also provided with a pump 140, which is controlled by control unit 112 to recirculate a certain percentage of the WFPD exiting sterile sterilizing grade filters 70a and 70b. In the illustrated example, pump 140 pulls 70 milliliters per minute from 300 milliliters per minute exiting sterile sterilizing grade filters 70a and 70b. The resulting 230 milliliters per minute of flow to cassette 42 at cycler 20 is sufficient. The pressure in disposable recirculation line 202a and the portion of water purifier recirculation line 204a leading from water circulation connector 204b to the inlet of pump 140 is normally low because the line begins downstream of sterile sterilizing grade filters 70a and 70b, which have caused a large pressure drop. If there is a breach at one or more of sterile sterilizing grade filters 70a and 70b, the low pressure portion of recirculation loop 200 absorbs the increase in downstream pressure and provides enough time for water purifier 110 to sense a corresponding pressure drop and take appropriate action, such as entering a safe mode in which its pumps are shut down and an alert is sent wired or wirelessly to cycler 20, which in turn alarms audibly, visually or audio-visually at user interface 30.

Alternative to Drain Line Sensing

Figure 7:
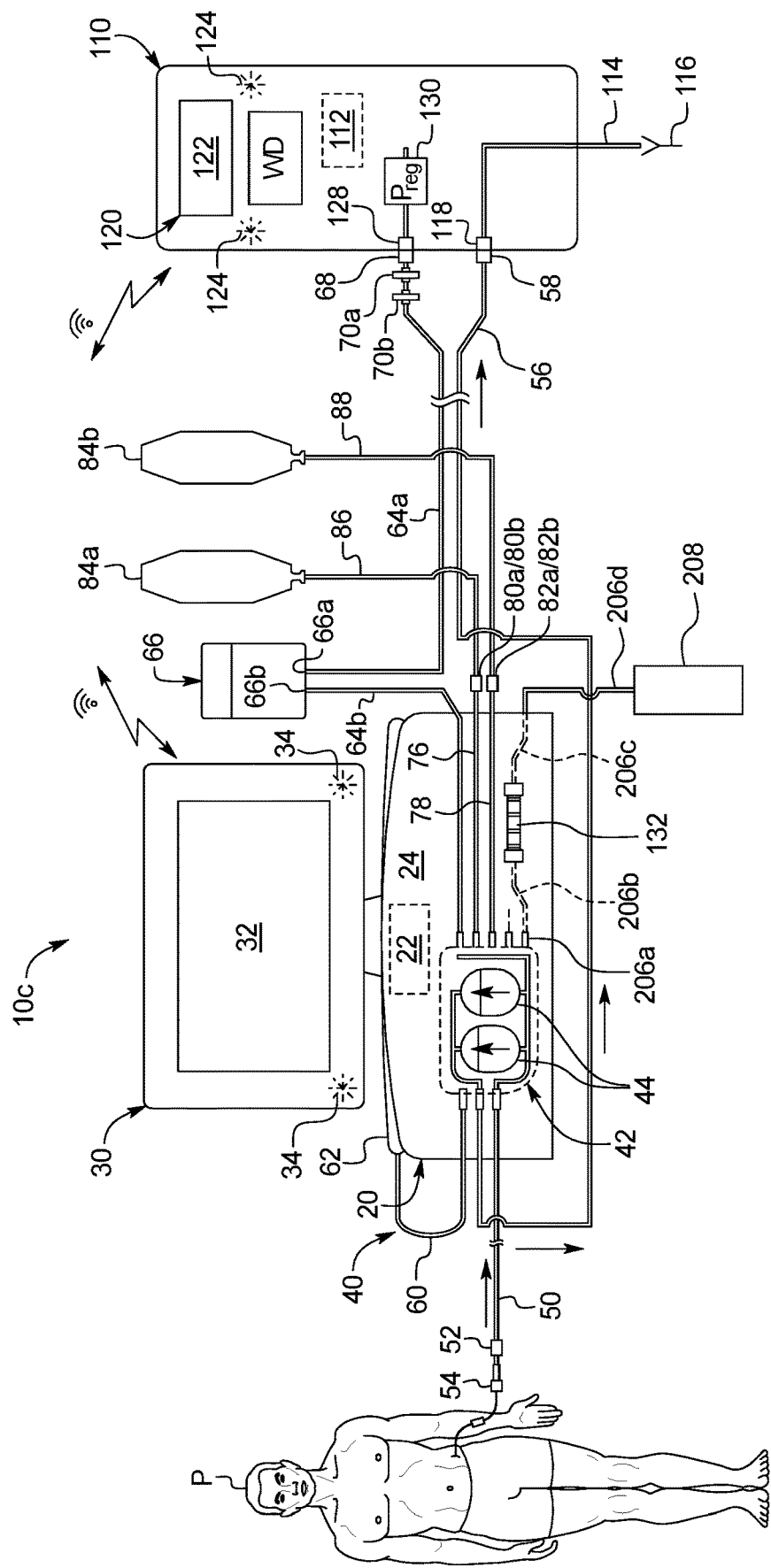
FIG. 7 is a front elevation view of another embodiment of a peritoneal dialysis system having point of use dialysis fluid production of the present disclosure.

Referring now to FIG. 7, one embodiment of an alternative dialysis system 10c having of point of use dialysis fluid preparation is illustrated. System 10c has many of the same components as system 10a and like elements, including all alternative embodiments discussed for such elements, are numbered the same. Point of use dialysis fluid preparation systems 10a, 10b and 10d each show conductivity sensor 132 located in drain line 56 at water purifier 110. System 10c locates conductivity sensor 132 instead inside cycler 20 and in a separate sample line 206a, 206b, 206c and 206d, not drain line 56. In the illustrated embodiment, sample line portions 206a and 206d are part of disposable set 40, while sample line portions 206b and 206c, placed in fluid communication with disposable sample line portions 206a and 206d, respectively, are connected to conductivity sensor 132 and are permanent within housing 24 of cycler 20.

Disposable sample line portion 206d leads to a sample bag 208. When loading disposable set 40 in system 10c, patient P or other user connects disposable sample line portions 206a and 206d to appropriate connectors located at housing 24 of cycler 20. The ends of sample line portions 206a and 206d may be configured to connect together after treatment like water line connector 68 and drain connector 58 described above, so that disposable set 40 may be disposed of easily without spillage.

Method 210 of FIG. 5 operates the same with system 10c except that when checking a mixed sample at diamond 236, control unit 22 of cycler 20 causes cassette fluid valves 46 leading to (i) heater/mixing line 60 and heater/mixing bag 62 and (ii) sample line 206a, 206b, 206c and 206d to open (instead of drain line 56), allowing fluid pump chambers 44 of cassette 42 to pump a desired sample amount of mixed dialysis fluid, e.g., 80 to 100 milliliters, from heater/mixing bag 62 to conductivity sensor 132. As before, the sample is preceded and followed by the pumping via cassette 42 of WFPD from water accumulator 66 to conductivity sensor 132. WFPD and the mixed dialysis fluid sample are collected in sample bag 208.

Alternative Mixing Regime and Dialysis Fluid Testing

Figure 8:
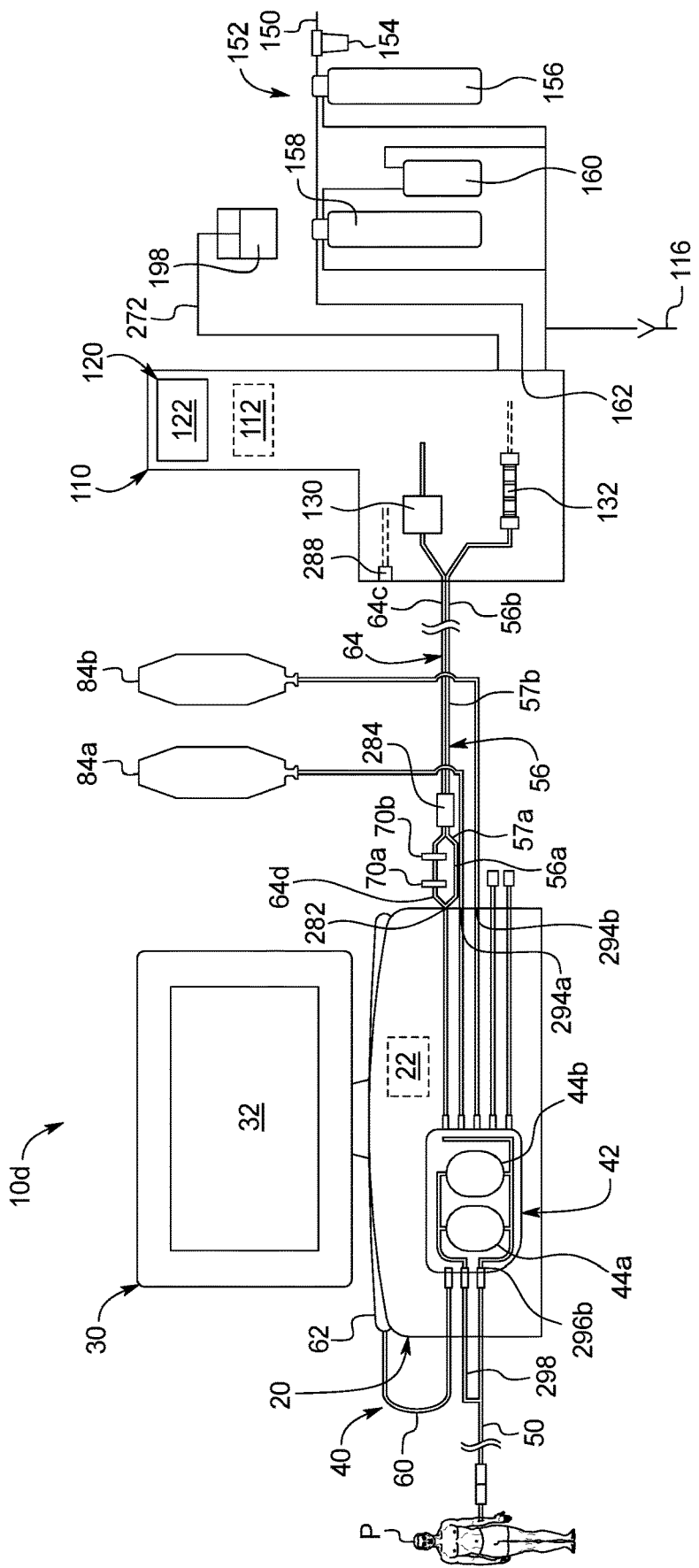
FIG. 8 is a front elevation view of a further embodiment of a peritoneal dialysis system having point of use dialysis fluid production of the present disclosure.

FIG. 8 illustrates a further alternative system 10d for proportioning fluids from WFPD and at least a first concentrate in an embodiment of the present disclosure. System 10d is generally intended for the on-site preparation of treatment fluids and for the treatment of the patient with the prepared fluids. In an embodiment, system 10d is configured to treat patients suffering from renal insufficiency, and in particular using peritoneal dialysis cycler 20. System 10d is also configured to prepare a peritoneal dialysis fluid by mixing purified water (on site prepared) and concentrates and for treating a patient in a peritoneal dialysis treatment.

System 10d as before includes a water purifier 110 and a cycler 20. A proportioning device may be said to be made of a peritoneal dialysis ("PD") cycler 20, which operates a circuit of disposable set 40, which includes a cassette 42 to which a plurality of lines and a container, such as a heater/mixing bag 62 configured to receive a treatment fluid, are connected.

In the illustrated embodiment of FIG. 8, water purifier 110 receives water from a house water source 150, such as a continuous source of pottable or drinkable water from a patient's home. In various embodiments, water purifier 110 may be installed in a room having access to the water source 150 to provide WFPD to cycler 20 as discussed herein.

A water softener module 152 may be provided in order to reduce/control water hardness. Water softener module in the illustrated embodiment includes a pre-filter 154 to remove dirt and sediment and a carbon filter 156 to further remove contaminants and impurities. Water softening may alternatively or additionally be achieved using lime softening or ion-exchange resins, as known in the art. FIG. 8 schematically shows an ion-exchange resin cartridge 158 and regenerating salts 160, such as NaCl salts.

It should be appreciated that water softener module 152 is optional and may not be present. It should also be appreciated that the water purifiers 110 of any of systems 10a to 10d discussed herein, and indeed with any of the alternative embodiments discussed herein, may be provided with water softener module 152 even though the module is not illustrated or described with those systems or embodiments.

An exemplary embodiment of water purifier 110 is discussed in connection with FIG. 16. Softened (or unsoftened) water enters water purifier 110 via a water intake 162. FIG. 16 illustrates that water purifier 110 includes a purifying circuit 164 that accepts water from water intake 162 and that includes a reverse osmosis module 166 to purify water from the intake 162. In particular, feed water enters water purifier 110 via the water intake 162 controlled by an inlet valve 168 (e.g., a solenoid valve) under control of control unit 112 of water purifier 110. A conductivity cell 170a located downstream of the inlet valve 168 along the flow path monitors the incoming water conductivity. Incoming water then passes a constant flow valve 172, which produces a steady flow of water into a reservoir or tank 174 providing that the water pressure is above a minimum pressure for constant flow valve 172.

Low and high-level switches 178a and 178b provided in reservoir or tank 174 detect its water level, while a computer program run on a control unit 112 of water purified 110 controls the opening and closed of inlet valve 168, which is open during the filling of tank 174, and closed when the water level in reservoir 174 activates its high-level switch 178b connected to control unit 112. Inlet valve 168 opens again when the water level falls below low-level switch 178a of reservoir 174, tripping the low-level switch connected to control unit 112. If the water level in the reservoir 174 rises too high, excess water is drained via a tank air vent 176 (overflow connection) to drain 116.

Water purifier 110 includes a reverse osmosis ("RO") pump 140. Control unit 112 causes pump 140 to stop if low level switch 178a in reservoir 174 detects air or a critically low water level. RO pump 140 provides the water flow and pressure requisite for the reverse osmosis process taking place at reverse osmosis module 166. Reverse osmosis module 166 filters water as is known to provide purified water at its purified water exit 180a. Reject water leaving reverse osmosis module 166 at a second exit 180b may be fed back into RO pump 140 to conserve water consumption or alternatively be pumped to drain 116.

Purified water leaving the RO module 166 passes any one or more of a flow meter 182, a heater 184a, and a first temperature sensor 186a. An additional conductivity cell 170b monitors the conductivity of purified water leaving reverse osmosis module 166. The purified water leaves water purifier 110 through a purified water outlet and flows to PD cycler 20 via a (purified) water line 64 shown also in FIG. 8. Pressure regulator 130 as discussed above is positioned at the purified water outlet upstream of water line 64 for regulating fluid pressure in the water line 64 downstream from pressure regulator 130.

Excess purified water, not used at cycler 20, returns to reservoir 174 via a recirculation line 188 provided with a one-way or check valve 280 that prevents water in reservoir 174 from flowing through recirculation line 188 into water line 64. In recirculation line 188, the purified water may also pass a second temperature sensor 186b before re-entering reservoir 174.

A portion of the rejected water leaving the RO module 166 via line 180b passes an auxiliary constant flow valve 190, which provides a steady flow of rejected water to a three-way valve 192a (e.g. a three-way solenoid valve) under control of control unit 112. A remaining portion of the rejected water returns to RO pump 140 via a valve 194 (e.g., a manual needle valve). Three-way valve 192a selectively diverts the rejected water either to drain 116 or back to reservoir 174. Before reaching reservoir 174, the rejected water may also pass one or more of a flow indicator 196, an additional heater 184b and a third temperature sensor 186c. All meters and sensors described in connection with water purifier 110 in FIG. 16 send their corresponding signals to control unit 112 in one embodiment.

Referring again to FIG. 8, system 10d in one embodiment includes a container 198 containing a microbiological growth inhibiting agent. As illustrated, container 198 is in fluid communication with water purifier 110 and/or cycler 20. In FIG. 8, line 272 connects container 198 to purifying circuit 164 (FIG. 16) of water purifier 110. Alternatively, container 198 may be connected via a line (not illustrated) leading directly to disposable cassette 42 operating with cycler 20, or be connected to water line 64, or be connected to drain line 56.

The agent inhibiting microbiological growth in the container 198 may be a suitable physiologically safe acid, such as citric acid, citrate, lactic acid, acetic acid, or hydrochloric acid (or a combination thereof). In one the preferred embodiment, container 198 contains citric acid, citrate or a derivative thereof. It is noted that container 198 may also include additives provided together with the acid (such as with citric acid).

Water purifier 110 shown in FIG. 16 may accordingly also include a disinfection circuit. Here, water purifier 110 presents a chemical intake 274, located for example at the front of purifier 110. When an external source of cleaning or disinfection solution (e.g., container 198) is connected to the chemical intake 274, a presence sensor 276 (e.g. an optical sensor) senses the external source connection. A three-way valve 192b under control of control unit 112 at chemical intake 274 opens towards a chemical intake pump 274a and reservoir 174. The chemical intake pump 274a feeds disinfecting solution into reservoir 174. Optical sensor 276 detects if the source of cleaning or disinfection solution is connected or disconnected. If/when the source is removed or is not detected by sensor 276, the chemical intake pump 274a is stopped or not activated and three-way valve 192b is closed towards the chemical intake 274 and instead allows for recirculation from reservoir 174, through valve 192b, back to the reservoir 174. Three-way valve 192a under control of control unit 112 may also be used to recirculate water and disinfectant from and to reservoir 174 during the phases of chemical disinfection, cleaning and/or rinse.

In a more detailed disinfection phase example, when chemical disinfection is initiated, the level in reservoir 174 is adjusted to a level just above low-level switch 178a. Control unit 112 causes RO pump 140 to start and run until empty level switch 178a indicates a presence of air. RO pump 140 is then stopped and inlet valve 168 is opened. Valve 168 is maintained open until empty level switch 178a indicates water. Chemical intake pump 274a is then run until a preset amount of chemical solution is metered into reservoir 174. When the level in reservoir 174 reaches high-level switch 178b via the intake of disinfectant, three-way valve 192a is opened to drain 116. RO pump 140 circulates the fluid in the flow path during the chemical intake phase and may be operated in two directions to create turbulent flow and to increase disinfection time and contact. At the end of the intake phase, bypass valve 278 is opened and the three-way valve 192a is actuated to open line 114 to drain 116 and to drain the water level in reservoir 174 to its low-level at switch 178a.

When the disinfection source (e.g., container 198 in FIG. 8) is removed, reservoir 174 is filled with water to high-level switch 178b, bypass valve 278 is closed and three-way valve 192a is closed in each direction. Control unit 112 then causes RO pump 140 to begin circulation through the RO module 166, while chemical intake pump 274a begins the circulation through chemical intake unit 274, while return overflow valve 280 is opened. Control unit 112 causes the circulation in the flow path to continue for a preset amount of time. The speed of RO pump 140 is then reduced, bypass valve 278 is opened and the three-way valve 192a is opened to drain 116. Control unit 112 causes both valves 192a and 278 to be deactivated and both pumps 140 and 274a to be stopped when the fluid level falls below low-level switch 178a.

Purifying circuit 164 in FIG. 16, including the disinfection components just described, may be enclosed inside of a single water purification cabinet 110a. As mentioned above, purified water is sent from water purifier 110 to disposable set 40 (FIG. 8) via water line 64. Referring again to FIG. 8, water line 64 feeds purified water to a water port 282 of cassette 42 of disposable set 40. Water line 64 is in one embodiment a flexible tube having a first end 64c connected to an exit of the purifying circuit 164 of the water purifier 110 (FIG. 16) and a second end 64d connected to the water port 282 of the cycler 20. Water line 64 may be at least 2 meters long and in one embodiment longer than 4 meters. Water line 64 allows water purifier 110 to be installed in a room having an available water source, while cycler 20 resides in a different room in which the patient resides, e.g., sleeps. Water tube 64 may accordingly be as long as necessary to connect water purifier 110 to cycler 20.

FIG. 8 also illustrates that system 10d includes a drain line 56 configuration to conduct fluid, such as used dialysis fluid, to a drain, for example drain 116 of water purifier 110. Drain line 56 may be a tube having a first end 56a connected to cassette 42 of cycler 20 and a second end 56b connected to purifying circuit 164 of the water purifier 110. Drain line 56 may also be a flexible tube, which may be more than 2 meters long and in one embodiment longer than 4 meters. Drain line 56 may be as long as necessary to connect between water purifier 110 and cycler 20. Water line 64 and drain line 56 in the illustrated embodiment run parallel using dual lumen tubing. It is also possible that water purifier 110 and PD cycler 20 are close together, such that the same two line fluid path including water line 64 and drain line 56 may for example be less than 0.5 meters. Moreover, while a dual lumen water line 64 and the drain line 56 are illustrated, it is possible that water line 64 and drain line 56 are separate.

In the illustrated embodiment of FIG. 8, water line 64 and drain line 56 are in direct fluid communication with one another. In particular, their respective ends 64d and 56a are connected to water port 282 of the cassette 42. Drain line 56 and the water line 64 accordingly both fluidly communicate with cycler 20 via water port 282. Drain line 56 in the illustrated embodiment is a tube having one end 56a connected to end 64d of water line 64. Again, water line 64 and drain line 56 may be made from a single dual lumen piece.

Figure 11:
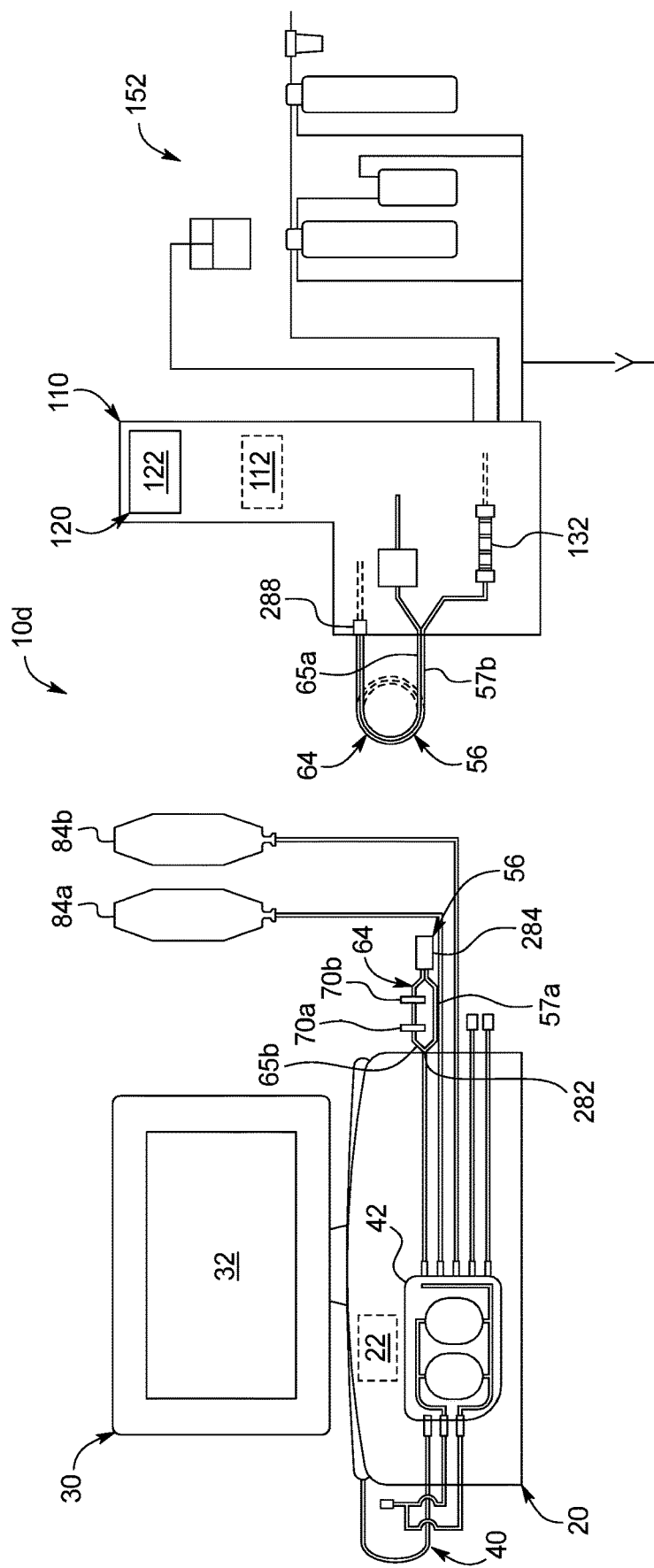
FIG. 11 is a front elevation view of the system of FIG. 8 prior to water purifier connection.
Figure 12:
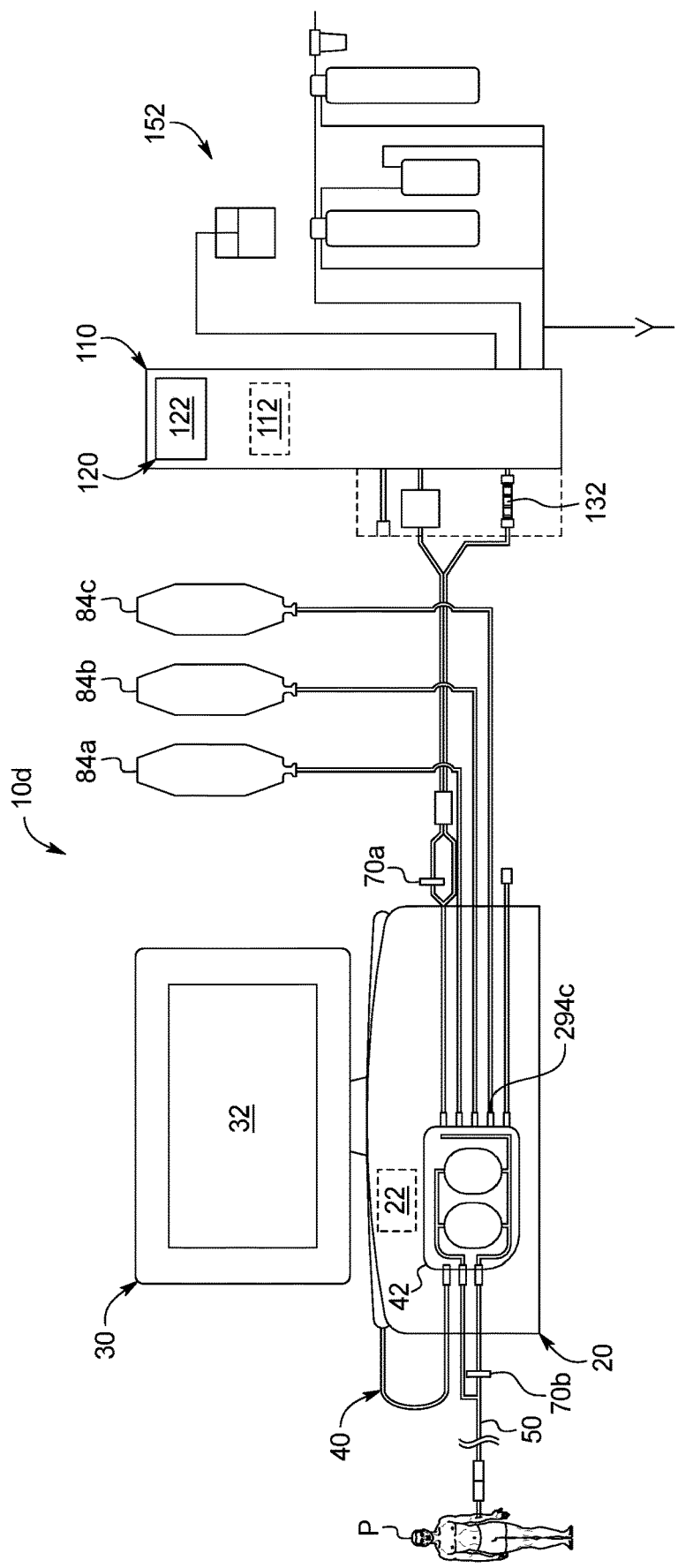
FIG. 12 is a front elevation view of the system of FIG. 8 having an additional concentrate and sterile sterilizing grade filters placed in separate locations along the disposable set.

Referring to FIGS. 8, 11 and 12, water line 64 (FIG. 11) includes a first tract 65a and a second tract 65b connected to the first tract via a connector 284. Second tract 65b is connected to said water port 282 and may present a first sterile sterilizing grade filter 70a. In the illustrated embodiment, second tract 65b is permanently or removeably connected to cassette 42 and thus a disposable part. In the illustrated embodiment, water line 64 may include a second redundant sterile sterilizing grade filter 70b placed in series with first sterile sterilizing grade filter 70a, for example positioned in the same disposable second tract 65b connected to cassette 42.

Sterile sterilizing grade filters 70a and 70b are disposable in one embodiment. Sterile sterilizing grade filters 70a and 70b may be less than 0.1 micron filters that create WFPD from the already highly purified water exiting water purifier 110. Suitable sterile sterilizing grade filter 70a and 70b are specified herein.

As illustrated in FIG. 11, the drain line 56 may include a first drain tract 57a and a second drain tract 57b connected to the first drain tract via a connector 284. First drain tract 57a is connected permanently or removeably to water port 282 of cassette 42 and forms part of water line 64. In one embodiment, first drain tract 57a of the drain line 56 is connected to second water tract 65b of the water line 64. The first drain tract 57a of the drain line 56 and the second water tract 65b of the water line 64 form a loop to connector 284 as illustrated in FIG. 11. FIG. 11 illustrates that the loop starts at connector 284, runs to a tube portion of water line 64, runs to a tube portion of drain line 56 and ends at connector 284.

Figure 10:
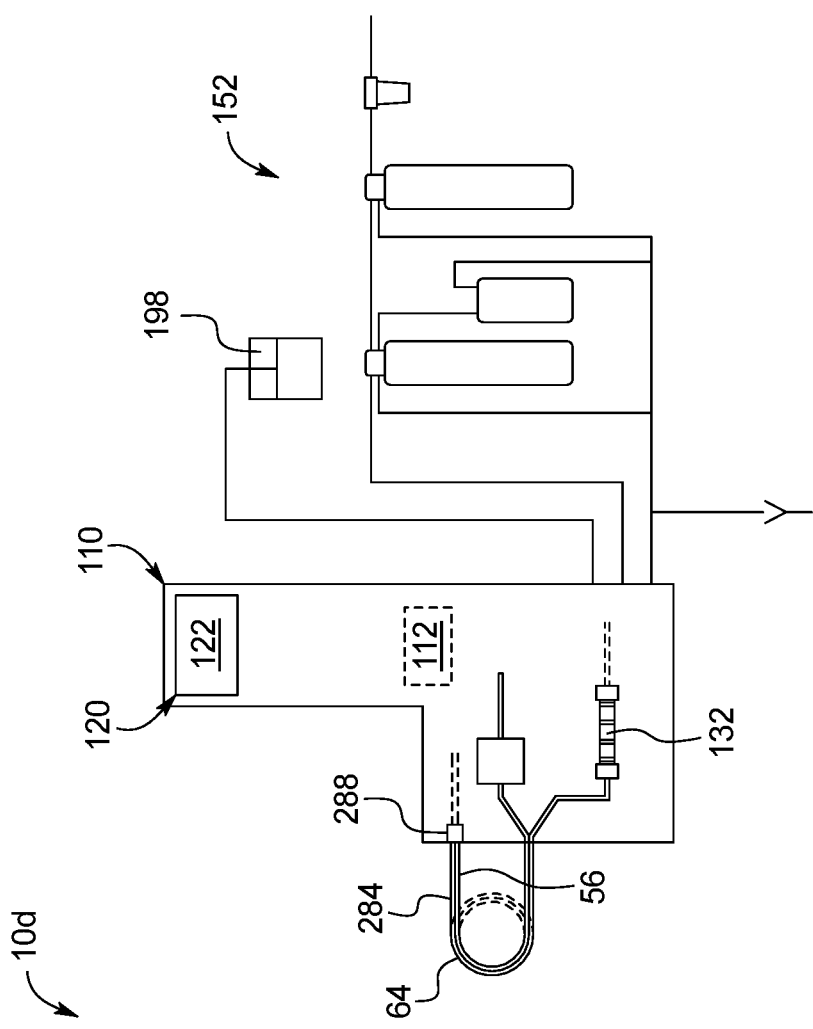
FIG. 10 is a front elevation view of the system of FIG. 8 prior to concentrate container connection.
Figure 10:
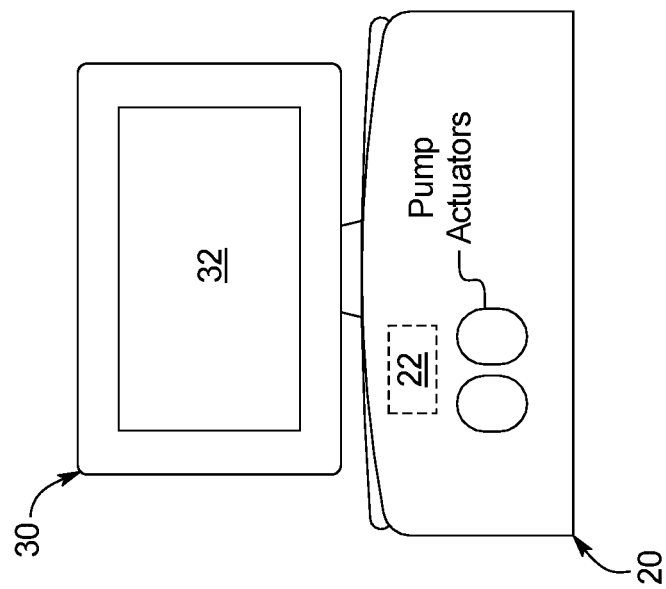

FIG. 10 illustrates that water line 64 and drain line 56 include terminal connector 284 configured for connecting free ends of the respective lines 64 and 56 to an intake 288 of the purifying circuit 164 of the water purifier 110 for disinfection of the water and drain lines.

Figure 9A:
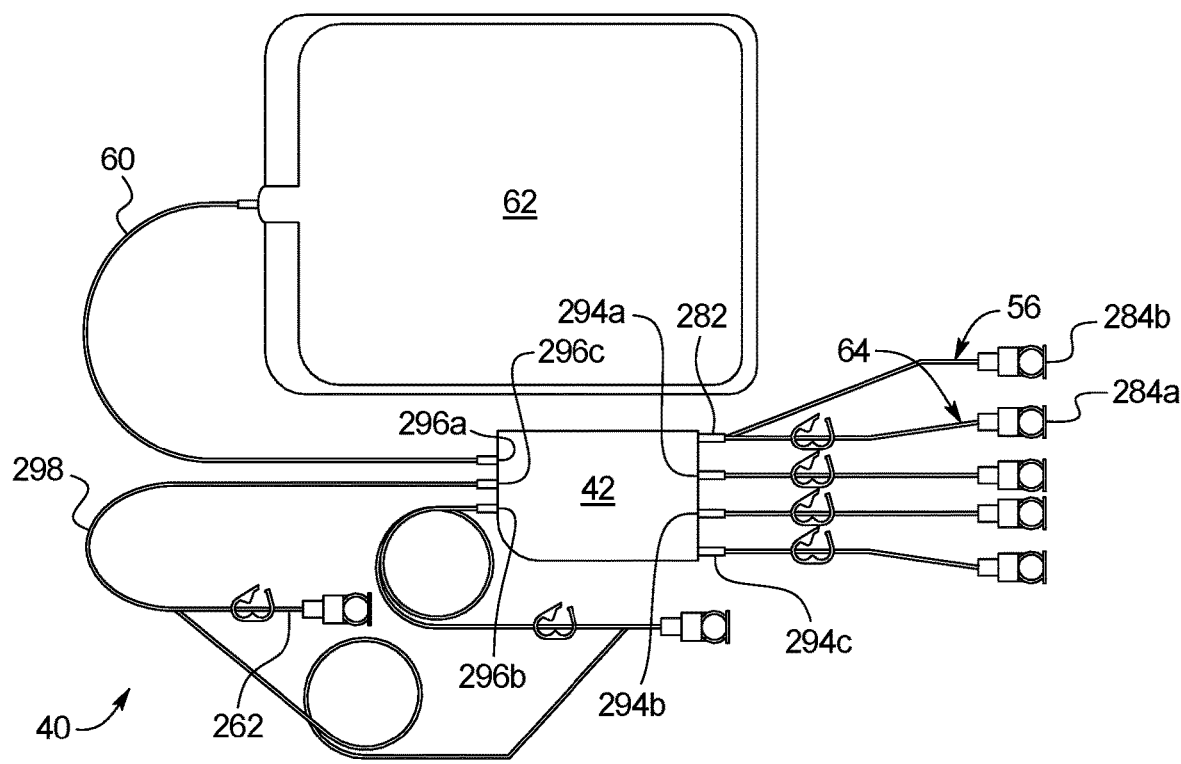
FIG. 9A is an elevation view of one embodiment of a disposable set used with the system illustrated in FIG. 8.
Figure 9B:
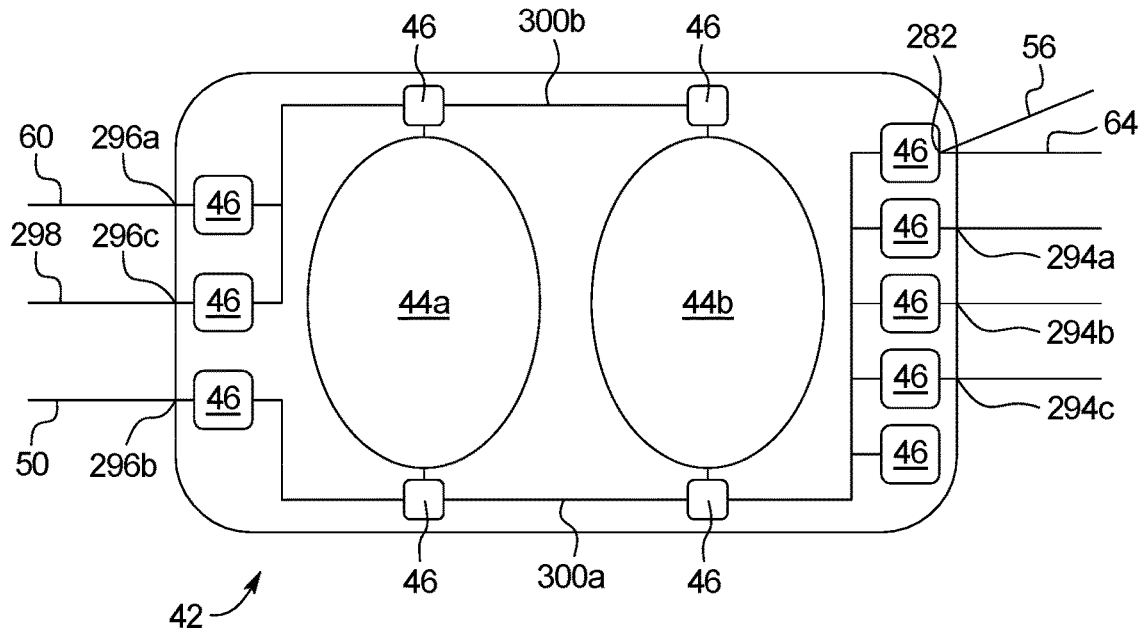
FIG. 9B is an elevation view illustrating the disposable cassette of the disposable set illustrated in FIG. 9A.

FIG. 9A illustrates a different embodiment, in which each of the water line 64 and of the drain line 56 has a separate respective connector 284a, 284b separated one from the other. FIG. 9B illustrates that regardless of whether a single connector 284 is used (FIG. 11) or separate connectors 284a, 284b are used (FIG. 9A), respective ends of water line 64 and of drain line 56 both connect to or run to water port 282 of cassette 42. Cassette 42 defines an internal fluid passageway communicating with port 282 to direct fluid within cassette 42 of disposable set 40.

FIG. 8 illustrates that water purifier 110 further includes at least one sensor 132 for detecting a property of a fluid flowing in the water line 64 and/or in drain line 56. Sensor 132 may be a conductivity sensor or a concentration sensor located in the drain line 56, and in one embodiment in the second drain tract 57b of drain line 56. In the illustrated embodiment, sensor 132 is included in the circuit inside the cabinet 110a (FIG. 16) of water purifier 110. In an alternative embodiment (not shown), sensor 132 may be located at the first end 56a of drain line 56, for instance, at first drain tract 57a.

Additionally, a second sensor (not illustrated) for detecting a property (e.g., the same property detected by first sensor 132, e.g. conductivity) of the fluid flowing in water line 64 and/or in the drain line 56 may be provided. The second sensor may be a conductivity sensor or a concentration sensor and may or may not be located in series with first sensor 132. The second sensor may be positioned in a different portion of the purifying circuit 164 of water purifier 110. Drained fluid may for example be directed from time to time to the second sensor to check proper working operation of first sensor 132.

As mentioned above, system 10d in one embodiment includes two additional filtration stages for purified water flowing downstream from purifying unit 110. In one embodiment, two disposable sterile sterilizing grade filters 70a and 70b on the water line 64 may be used. However, alternative configurations may be adopted. FIG. 12 illustrates one possible alternative configuration in which a first disposable sterile sterilizing grade filter 70a is still located along water line 64, while a second sterile disposable sterile sterilizing grade filter 70b is located along a patient line 50, extending from cassette 42 to patient P.

Figure 13:
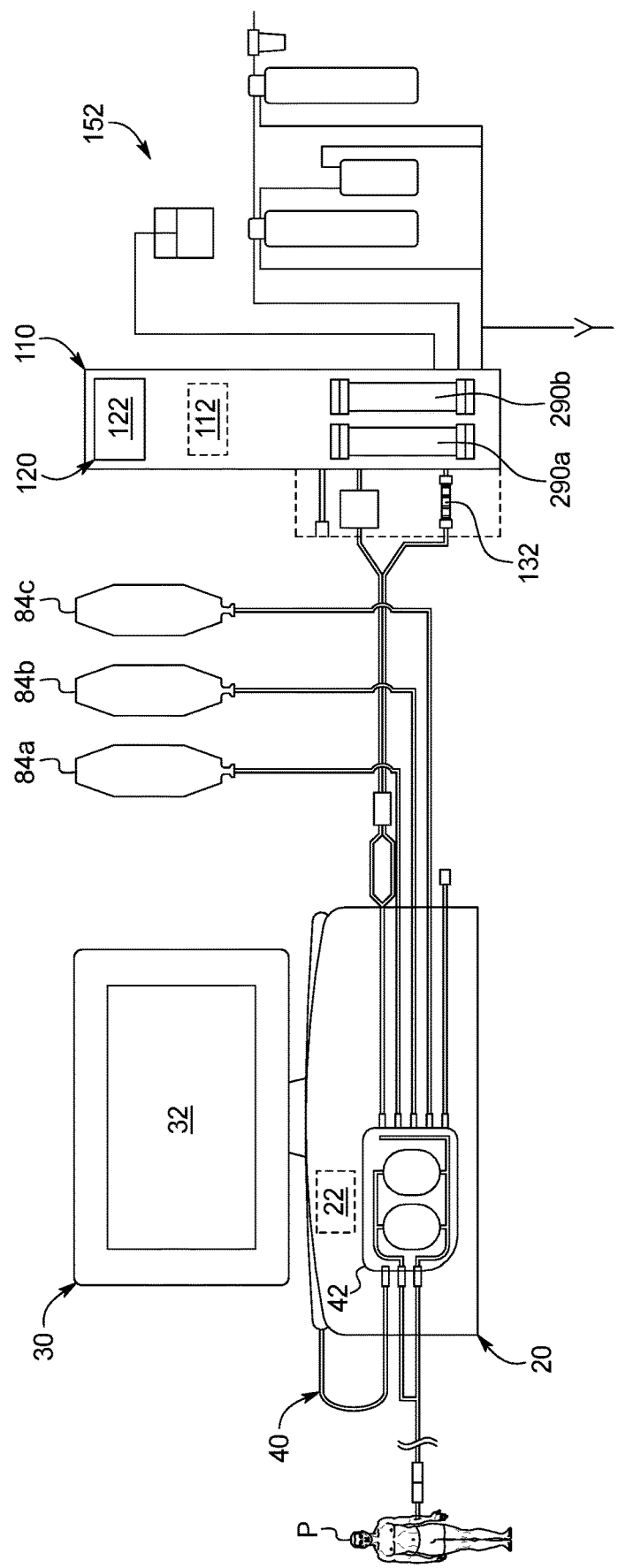
FIG. 13 is a front elevation view of the system of FIG. 8, but which uses ultrafilters instead of sterile sterilizing grade filters to produce water for peritoneal dialysis ("WFPD").

FIG. 13 illustrates an alternative configuration for water purifier 110 in which the water purifier 110 includes at least a first ultrafilter 290a and a second ultrafilter 290b, which are known to those of skill in the art. Water to be purified passes through the two ultrafilters 290a, 290b located at the end of purifying circuit 164 so that water purifier 110 itself provides WFPD. Ultrafilters 290a, 290b are not daily use disposables like disposable sterile sterilizing grade filters 70a, 70b but do need to be replaced after a given number of treatments or ours of service.

Figure 14:
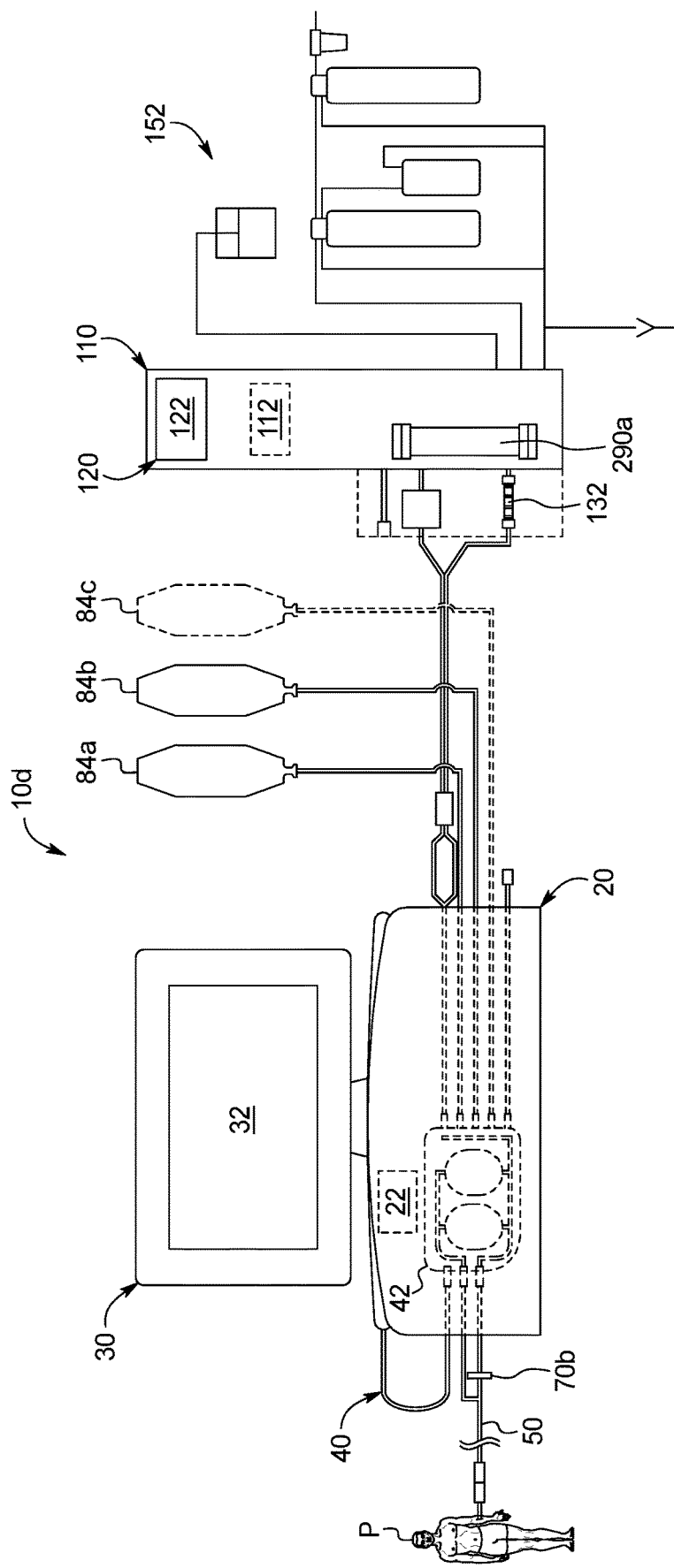
FIG. 14 is a front elevation view of the system of FIG. 8, but which uses an ultrafilter in combination with a sterilizing filter at a first location to produce WFPD.
Figure 15:
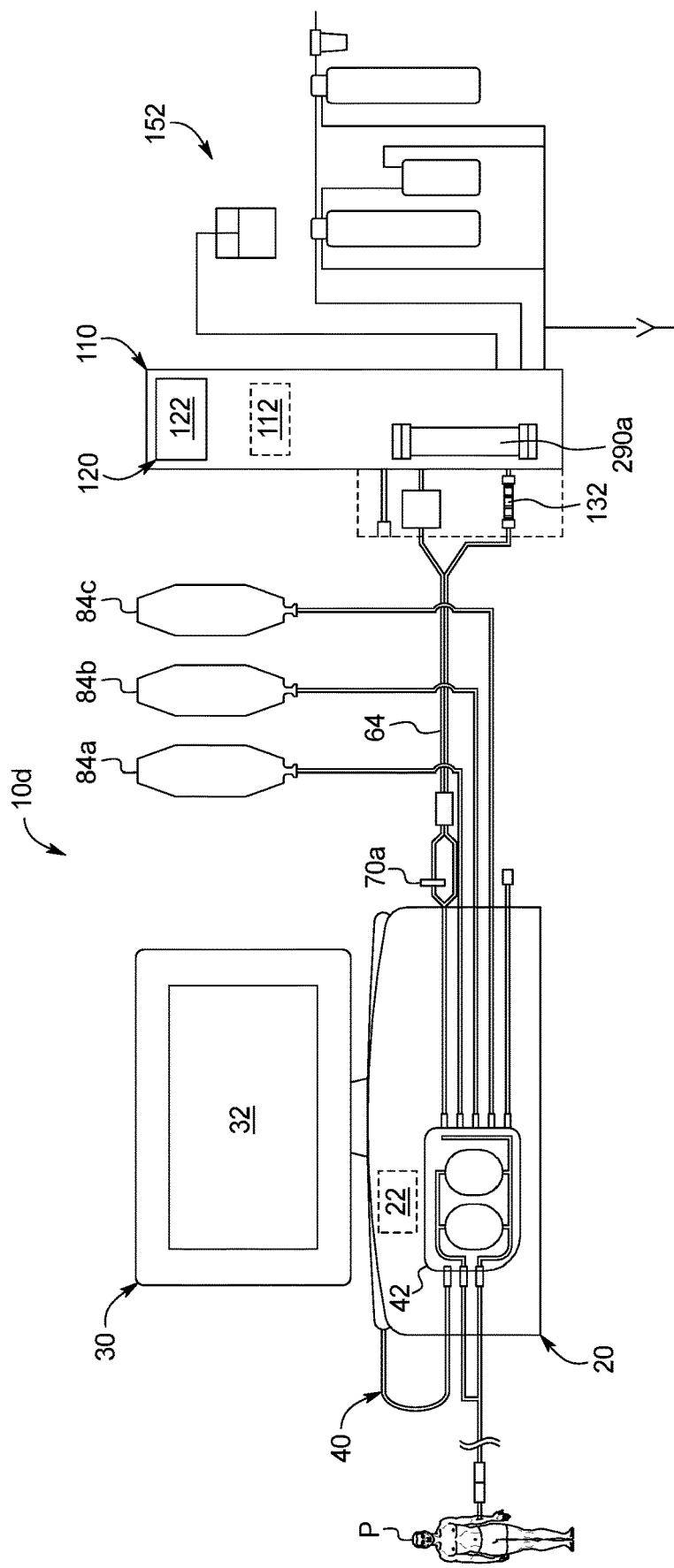
FIG. 15 is a front elevation view of the system of FIG. 8, but which uses an ultrafilter in combination with a sterilizing filter at a second location to produce WFPD.

FIG. 14 shows an additional alternative embodiment including at least one of the above-mentioned ultrafilters 290a and/or 290b located in water purifier 110 in combination with a disposable sterile sterilizing grade filter 70a, located along patient line 50. FIG. 14 shows an embodiment including only one ultrafilter 290a, located in water purifier 110 provided in combination with a disposable sterile sterilizing grade filter 70a located along patient line 50. It should be understood that both ultrafilters 290a and 290b may be used instead in combination with a disposable sterile sterilizing grade filter 70a located along patient line 50 (or water line 64). FIG. 15 shows yet another alternative embodiment including only one ultrafilter 290a located in water purifier 110 provided in combination with a disposable sterile sterilizing grade filter 70a located along water line 64. Other combinations include one ultrafilter with two sterile sterilizing grade filters, two ultrafilters with one sterile sterilizing grade filter, and two ultrafilters with two sterile sterilizing grade filters.

As illustrated in FIG. 8, system 10d further includes at least one source 84a of a first concentrate placed in fluid communication with a first inlet concentrate port 294a (e.g., via concentrate line 76/86) of disposable cassette 42. Source 84a of the first concentrate is provided as a first container, wherein first container 84a may be used for several PD fluid preparation cycles until all of the concentrate contained therein has been used. In one embodiment, first concentrate of container 84a contains an appropriate osmotic agent, such as dextrose. In a non-limiting example, the first concentrate includes 50% dextrose at pH between 2 and 3. The volume of the first concentrate may be from 1 to 4 liters.

System 10d further includes at least one source 84b of a second concentrate placed in fluid communication with a second inlet concentrate port 294b (e.g., concentrate line 78/88) of disposable cassette 42. Source 84b of the second concentrate may be provided in a second container, wherein second container 84b may be used for several PD fluid preparation cycles until all of the concentrate contained therein has been used. In one embodiment, the second concentrate contains electrolytes and a buffer agent, for example lactate. In a non-limiting example, the second concentrate includes sodium chloride, calcium chloride, magnesium chloride and sodium lactate at pH higher than 6. The volume of the second concentrate may be from 0.5 to 4 liters.

It is contemplated that two concentrates containers 84a, 84b will be used, however, three or more concentrates may be used alternative. For example, FIG. 12 shows a source 84c of a third concentrate placed in fluid communication with a third inlet concentrate port 294c of cycler 20. Source 84c of the third concentrate may be provided in a third container, wherein third container 84c may be used for several PD fluid preparation cycles until all of the concentrate contained therein has been used.

In the case of FIG. 12 in which three concentrates are used, the second concentrate may, as an example, include sodium chloride, sodium lactate and sodium bicarbonate, while the third concentrate may, as an example, include other electrolytes, such as calcium and magnesium chloride. In an alternative embodiments, the fluid in third container 84c may be a drug, a nutritional supplement, or combinations thereof. Of course different content for the concentrates may be adopted depending on the needs of patient P and his/her specific circumstances.

First, second and third concentrates 84a to 84c are in one embodiment pre-made and pre-sterilized. It is contemplated however that one or more or all of containers 84a to 84c may include a dry concentrate that receives a precise amount of WFPD prior to treatment via water purifier 110 pumped through cassette 42 into concentrates 84a to 84c.

As discussed above, disposable set 40 includes a disposable cassette 42, one embodiment for which is illustrated in FIG. 9A. Here, disposable set 40 includes disposable cassette 42, in combination with plural tubes. Tubing set 40 includes a heater/mixing line 60 emerging from a heater/mixing port 296a of cassette 42 and terminating at heater/mixing container 62, which is configured for receiving WFPD and mixing it to form dialysis fluid. Heater/mixing container 62 is one embodiment a collapsible bag sized to be positioned on a dedicated tray located at the top of cycler 20.

Disposable set 40 also includes a portion of the water line 64 and a portion of the drain line 56 both emerging from the water port 282 in FIGS. 9A and 9B and three (or more) line portions emerging from first, second and third concentrate ports 294a to 294c. Ports 294a to 294c are configured for connection to respective concentrate bags. FIG. 9A shows three line portions for connection to concentrates, while FIGS. 8 and 9B illustrate (on the right side of cassette 42) water port 282 and four additional ports in the cassette, where at least two of the four parts may be used for connection to concentrates.

Patient line 50 emerges from a patient port 296b of cassette 42 in FIGS. 9A and 9B. One end of patient line 50 is configured for connection to a transfer set worn by patient P. An additional line 298 extends from port 296c of cassette 42 in FIGS. 9A and 9B. Additional line 298 may be used as an additional drain line, as a sample line, or (as shown in FIG. 9A) may have one end connected to the patient line 50 to create a dialysis fluid loop. Cassette 42 may be provided with additional fluid lines as needed.

Cassette 42 in FIG. 9B is provided with first and second fluid pump chambers 44a, 44b. Pump chambers 44a and 44b are in selective fluid communication with ports 282, 294a to 294c, and 296a to 296c via fluid valve valves 46. Fluid pump chambers 44a and 44b and fluid valve chambers 46 are actuated pneumatically in one embodiment.

As illustrated in FIG. 9B, water port 282 (and thereby water line 64 and drain line 56), and the first, second and third ports 294a to 294c (and thereby the above-described concentrates) are selectively fluidly connected to common fluid passageways 300a and 300b formed in the rigid plastic portion of cassette 42. Fluid passageways 300a and 300b are also selectively fluidly connected to an inlet or an outlet port side of fluid pump chambers 44a and 44b. Patient port 296b is also connected to first common fluid passageway 300a.

Heater/mixing port 296a (and therefore heater/mixing container 62) and additional port 296c are in the illustrated embodiment fluidly connected to second common fluid passageway 300b formed in rigid cassette 42. Second common fluid passageway 300b is in turn in fluid communication with the opposite inlet or outlet ports of fluid pump chambers 44a and 44b.

First common fluid passageway 300a and second common passageway 300b communicate with each other by via fluid pump chambers 44a and 44b. In the case that main patient line 50 and additional patient or recirculation line 298 are connected to each other, a further communication path is created between fluid passageways 300a and 300b.

FIG. 9B illustrates that fluid valve chambers 46 are provided at the mentioned ports and also in fluid passageways 300a and 300b to direct dialysis fluid to or from fluid pump chambers 44a and 44b. Fluid valve chambers 46 are also provided at each of the fluid ports of cassette 42. In general, port valve chambers 46 decide which fluid flows to or from cassette 42, while fluid valve chambers 46 in passageways 300a and 300b decide which direction that the fluid flows. Fluid valves chambers 46 are actuated pneumatically in one embodiment. Here, positive and negative pressure acting on the valve chambers 46 (closing and opening the passages, respectively) allows for the selective changing of fluid flow inside cassette 42 of disposable set 40.

In FIG. 8, cycler 20 receives cassette 42 and its set of tubing. Cycler 20 is provided with a control unit 22, including one or more processor and memory programmed to drive respective pneumatic valve actuators (e.g., electrically activated pneumatic solenoid valves) to open or close each of fluid valve chambers 46 to create desired flow paths inside cassette 42 of disposable set 40.

Control unit 22 is also programmed to control pneumatic pump actuators, e.g., electrically activated pneumatic variable orifice valves, which selectively allow positive or negative pneumatic pressure to fluid pump chambers 44a and 44b. The valve and pump chambers are in one embodiment each covered by a membrane that is under positive and negative pressure. Positive pressure closes the membrane to occlude flow for fluid valve chambers 46 and pushes the membrane to expel fluid (WFPD, concentrate or dialysis fluid) for fluid pump chambers 44a and 44b. Negative pressure opens the membrane to allow flow through fluid valve chambers 46 and pulls the membrane to draw fluid (WFPD, concentrate or dialysis fluid) for fluid pump chambers 44a and 44b.

It should be appreciated that control unit 22 may be programmed such that either fluid pump chamber 44a and 44b may be used to pump any fluid to any desired destination. Fluid pump chambers 44a and 44b may be used to pump WFPD into cassette 42 individually or together, and/or back to water purifier 110. Fluid pump chambers 44a and 44b may be used alone or together to pump concentrates from containers 84a and 84b into cassette 42. Fluid pump chambers 44a and 44b may be used alone or together to pump mixed dialysis fluid to any one or more of water purifier 110, heating/mixing container 62, patient P or drain 116. Fluid pump chambers 44a and 44b may further be used to pump mixed dialysis fluid from heating/mixing container 62 to cassette 42. Each of the above operations is performed under the control of control unit 22 in one embodiment.

One example treatment setup for system 10d of the present disclosure is illustrated in the sequence of FIGS. 10 to 12. FIG. 10 shows system 10d between treatments, where water purifier 110 is disconnected from cycler 20, while water line 64 and drain line 56 are rolled into connection with water purifier 110. In one embodiment, water line 64 and drain line 56 are connected to an intake 288 of the purifying circuit 164 to create a properly closed fluid circuit in which disinfectant or hot water may be circulated during the disinfection of water purifier 110 prior to treatment.

FIG. 11 illustrates an initial setup step in which cycler 20 receives disposable set 40 including cassette 42, so that cycler 20 can actuate the pumping and valve membrane of the cassette. Cassette 42 and its associated set of lines is installed into the cycler 20. Cassette 42 is loaded into cycler 20 such that patient P may then be prompted by user interface 30 of cycler 20, which communicates with control unit 22, to connect concentrate containers 84a and 84b properly to cassette 42. As illustrated herein, the connectors of concentrate containers 84a and 84b may be made to be different so that it is ensured that the connectors are connected to the proper port of cassette 42.

FIG. 12 illustrates a next setup step, wherein interface 30 of cycler 20 prompts patient P to disconnect water and drain lines 64, 56 from the water purifier 110, unroll the water and drain lines, and connect the lines to cassette 42, e.g., by means of common connector 284. Again, water and drain lines 64, 56 are two separate lines, but may be provided as part of a single, dual lumen, tube.

Once the dialysis fluid is properly prepared, and disposable set 40 is properly primed, user interface 30 of cycler 20 notifies patient P of same and prompts patient P to connect to patient line 50 and begin treatment. The fluid circuit formed by disposable set 40 including cassette 42 may be reused for multiple treatments. In such a case, on days or for treatments in which the circuit of disposable set 40 is being reused, patient P need only wait until dialysis fluid is prepared properly and circuit of disposable set 40 is primed properly before reconnection to patient line 50 and the beginning of a new treatment. That is, the above connection steps between cycler 20 and water purifier 110 are not needed for reuse treatments. Discussed next is one embodiment for the online preparation of dialysis fluid.

Fluid Preparation for Alternative System 10d

Referring again to FIG. 8, fluid preparation begins when water purifier 110 feeds purified water to the water line 64. Here, water port 282 is closed via the appropriate fluid valve/actuator at cassette 42, forcing the purified water to flow through sterile sterilizing grade filters 70a, 70b and back through drain line 56 to the drain 116. This step fills the dual lumen tube 64, 56 connected to the cassette 42, including second tract 65b (FIG. 11) of water line 64 and first drain tract 57a of drain line 56.

In a second step, the water port 282 at cassette 42 is opened via an appropriate fluid valve 46 at cassette 42, allowing WFPD to be pumped via fluid pump chambers 44a and 44b into cassette 42 and heater/mixing bag 62 to prime same.

Next, concentrate checking is performed. Concentrate 84a is checked first in one embodiment. Water port 282 is closed and first inlet port 294a for concentrate 84a is opened at cassette 42. Control unit 22 causes pump chambers 44a and 44b and associated fluid valve chambers 46 of disposable cassette 42 to withdraw a prescribed amount of first concentrate from concentrate container 84a and pump said amount of concentrate into cassette 42, filling (at least partly) one of the fluid pump chambers 44a or 44b.

Control unit 22 causes first inlet port 294a to close and water port 282 to open. The fluid pump chamber 44a or 44b containing the first amount of concentrate 84a is actuated so that the first concentrate 84a is forced through water port 282 towards and into drain line 56. A sufficient amount of first concentrate reaches first drain tract 57a accordingly.

In a subsequent step, the control unit 22 (controlling all cycler 20 steps) drives cycler 20 to withdraw purified water from heater/mixing bag 62, and causes WFPD from heater/mixing bag 62 to be pumped to fill and flush first or second fluid pump chamber 44a or 44b, and then to push forward the WFPD from the fluid pump chamber to thereby push first concentrate 84a into drain line 56 and to remove first concentrate traces from the pump chamber 44a or 44b. First concentrate 84*a* is thereby forced through drain line 56 towards and past conductivity sensor 132.

In more detail, control unit 22 is in one embodiment programmed to cause cycler 20 to pump first concentrate 84*a* into first tract 57*a* of the drain line 56, wherein the first tract is positioned immediately downstream of water port 282. Control unit 22 causes cycler 20 to push first concentrate 84*a* along drain line 56 via WFPD from heater/mixing bag 62 and simultaneously flush the fluid pump chamber 44*a* or 44*b*. Water port 282 is then closed. As control unit 112 (including one or more processor or memory) of water purifier 110 causes the water purifier to pump purified water into the water line 64, the purified water from water purifier 110 pushes first concentrate 84*a* along drain line 56 to and past sensor 132. A property (e.g., conductivity) of first concentrate 84*a* is then measured and stored at control unit 112. Control unit 112 forwards the measurement property, e.g., wirelessly, to control unit 22 of cycler 20, which analyzes the measurement to identify and verify concentrate 84*a*.

Subsequent to identification and verification of first concentrate 84*a*, a similar procedure is adopted for second concentrate 84*b*. Here, second inlet port 294*b* is opened and at least one of pump chambers 44*a* and 44*b* is filled at least partially with second concentrate 84*b*. Control unit 22 causes membrane fluid pump chamber 44*a* or 44*b* to push second concentrate 84*b* towards drain line 56 and WFPD from the heater/mixing bag 62 to flush pump chamber 44*a* or 44*b* and to push second concentrate 84*b* further along the drain line 56. Water port 282 is closed and purified water from the water purifier 110 is caused to push second concentrate 84*b* to and past sensor 132. Second concentrate 84*b* is measured by sensor 132, stored at control unit 112 of water purifier 110, and sent to control unit 22 of cycler 20 to identify and confirm second concentrate 84*b*.

The identification steps may be optional or additional to personal container identification performed by the user and/or achieved through dedicated mechanical connectors as discussed herein, which prevent the incorrect connection of a concentrate containers 84*a* and 84*b* to cassette 42. System 10*d* is accordingly now ready for mixing the concentrates and water to produce PD fluid.

To prepare dialysis fluid in one embodiment, WFPD is pumped to heater/mixing bag 62 from water purifier 110, through sterile sterilizing grade filters 70*a* and 70*b*, through water port 282 via fluid pump chambers 44*a* and 44*b* and heater/mixing line 60. A first filling action pumps possible residual air present in disposable set 40 to heater/mixing bag 62 (or to drain 116). Control unit 22 then causes cycler 20 to pump first concentrate into heater/mixing bag 62 via the first inlet port 294*a*.

Control unit 22 may be programmed to cause cycler 20 to perform one or more additional mixing action. For example, any of fluid pump chambers 44*a* or 44*b* may be caused to withdraw into the pump chambers some amount of mixed fluid (e.g., made from one or both first and second concentrates 84*a*, 84*b* and WFPD) from heater/mixing bag 62, to send such mixture back to heater/mixing bag 62, and repeat this procedure multiple times (described herein as a "waffling").

Additional WFPD is then supplied via water line 64 to heater/mixing bag 62 so that fluid pump chambers 44*a* and 44*b* are rinsed with WFPD, and so that first mixed fluid in pump chambers 44*a* and 44*b* is pumped to heater/mixing bag 62. Control unit 22 then causes cycler 20 to pump second concentrate 84*b* to heater/mixing bag 62 via second inlet port 294*b*, fluid pump chambers 44*a* and 44*b* and heater/mixing line 60.

Again, control unit 22 may be programmed to cause cycler 20 to perform one or more additional mixing action. For example, any of fluid pump chambers 44*a* or 44*b* may be caused to withdraw into the pump chamber some amount of mixed fluid (e.g., fluid comprising the first and the second concentrate from the first and second concentrate containers 84*a*, 84*b* and WFPD) from heater/mixing bag 62, pump the mixture back to heater/mixing bag 62, and then repeat this procedure multiple times, to improve the mixing of the first and second mixed fluids (second "waffling" procedure).

Once the required quantities of first and second concentrates 84*a* and 84*b* have been suppled to the heater/mixing bag 62, control unit 22 in one embodiment starts a first dilution phase. Here, WFPD is added to heater/mixing bag 62 via water purifier 110 to reach about 90 to 95% (for example) of a final desired fluid volume of mixed dialysis solution.

Again, control unit 22 may be programmed to cause cycler 20 to perform an additional mixing action. For example, any of fluid pump chambers 44*a* or 44*b* may withdraw into the chambers an amount of diluted second mixed fluid (e.g., diluted fluid comprising first and second concentrates 84*a* and 84*b* and WFPD from heater/mixing bag 62), pump the mixture back to heater/mixing bag 62, and then repeat this procedure multiple times, to further mix the diluted second mixed fluid (third "waffling") procedure.

Control unit 22 then causes cycler 20 to verify that the diluted second mixed fluid has been mixed properly. To check proper mixing in one embodiment the conductivity of the mixed fluid in heater/mixing bag 62 is verified. Control unit 22 causes cycler 20 to actuate one or both of fluid pump chambers 44*a* or 44*b* to withdraw a desired amount of diluted second mixed fluid from heater/mixing bag 62 and direct the fluid into first drain tact 57*a* via water port 282.

In one embodiment, to not waste mixed treatment fluid, when the diluted second mixed fluid reaches the drain line 56, control unit 22 causes water port 282 to close and WFPD to be pushed by water purifier 110 in water line 64 towards drain line 56, thereby forcing the diluted second mixed fluid to flow past sensor 132 for a fluid property check. The sensed property measured at sensor 132 is received by control unit 112 of water purifier 110 and then sent to control unit 22 of cycler 20, e.g., wirelessly, to be analyzed against a setpoint valve as has been described herein.

Control unit 22 of cycler 20 in an embodiment then runs a second dilution step to fine tune the treatment solution composition. Here, additional WFPD is added to heater/mixing bag 62 to further dilute the mixture. The amount of added WFPD is calculated in one embodiment as a function of the measured property (e.g. conductivity) of the diluted second mixed fluid. In particular, control unit 22 may be programmed to determine the amount of additional WFPD as a function of the measured property in combination with the previously filled amount of mixed dialysis fluid (water and first and second concentrates 84*a* and 84*b*).

Again, control unit 22 may be programmed to cause cycler 20 to perform an additional mixing action. For example, any of fluid pump chambers 44*a* or 44*b* may withdraw into the chambers some additionally diluted second mixed fluid (e.g., diluted fluid comprising first and second concentrates 84*a*, 84*b* from the first and second concentrate containers 84*a*, 84*b* and WFPD) from heater/mixing bag 62, push the mixture back to heater/mixing bag 62, and then repeat this procedure multiple times, to improve the mixing of the additionally diluted second mixed fluid (fourth "waffling" procedure).

Control unit 22 is in one embodiment programmed to check the conductivity of the additionally diluted second mixed fluid to confirm correct preparation of the treatment fluid. Here, some additionally diluted second mixed fluid is withdrawn via cycler 20 pumping action from heater/mixing bag 62 and fed to drain line 56. Water purifier 110 then pushes WFPD through water line 64 to in turn push the additionally diluted second mixed fluid past sensor 132 for a final (e.g., conductivity or concentration) check. A sensor reading is sent, e.g., wirelessly, from control unit 112 to control unit 22 and analyzed at cycler 20 as discussed herein to verify the proper mixing of the dialysis fluid for treatment.

System 10d is now ready for treating a patient according to a doctor or clinician prescribed procedure programmed into control unit 22 via user interface 30. In one embodiment, patient P is connected to cassette 42, and used dialysis fluid from a prior treatment if present is removed from the patient's peritoneal cavity and delivered to drain 116 via drain line 56. Cycler 20 pumps a prescribed fill volume amount of on-site prepared dialysis fluid to the patient's peritoneal cavity, which is allowed to dwell within patient P for a preset or variable duration, after which cycler 20 causes fluid pump chambers 44a and 44b to pump used dialysis fluid including an amount of ultrafiltration removed from patient P to drain 116. The above draining, filling and dwelling steps are repeated one or more time to complete the prescribed treatment. Once all treatment steps are concluded, patient P is disconnected from disposable set 40, set 40 is removed from cycler 20 and water purifier 110 and discarded in one embodiment.

Disinfection Using Growth Inhibiting Agent

In an alternative embodiment, a procedure for extended life of disposable set 40 is performed, and may be used with any of systems 10a to 10d and any of their alternative embodiments described herein. Here, semi-disposable set 40 is used with cycler 20 for more than one treatment. Instead of removing disposable set 40 from cycler 20 and water purifier 110 after treatment, an agent formulated to inhibit microbiological growth is pumped from container 198 (FIG. 8) and diluted at water purifier 110. The diluted agent is pumped by water purifier 110 and/or cycler 20 into semi-disposable set 40, including cassette 42 and the associated line portions and heater/mixing bag 62 connected to the cassette 42.

The growth inhibiting agent may in one embodiment be or include citric acid, citrate or a derivative thereof, and may be pumped from container 198, diluted in a portion of the purifying circuit of water purifier 110, and then pushed into semi-disposable set 40, for example via water line 64. In an alternative embodiment, patient line 50 may be connected to a port of water purifier 110 to receive the diluted growth inhibiting agent for circulation within semi-disposable set 40.

Further alternatively, growth inhibiting agent container 198 may be in direct fluid communication with semi-disposable set 40, for example, via a connection from container 198 to patient line 50. Control unit 22 here causes citric acid or citrate (or other suitable acid with or without additives) to be withdrawn from container 198 and be pumped into cassette 42, lines connected thereto and heater/mixing bag 62.

Control unit 22 is in one embodiment programmed to perform one or more mixing step, e.g., the waffling as described herein, so that the agent inhibiting microbiological growth is diluted with the fluid already contained in the circuit, which may be WFPD. In this manner, semi-disposable set 40 is able to be used for more than one treatment instead of being discarded after a single use.

In one embodiment, diluted agent is left to reside in semi-disposable set 40 until the start of preparation for a next treatment. At the beginning of the next treatment, control unit 22 performs a rinsing step to remove the diluted growth inhibiting agent from semi-disposable set 40, wherein the rinsing may be performed using WFPD from water purifier 110 and the sterile sterilizing grade filters 70a and 70b.

It should be appreciated that the above-described procedure is not a disinfection procedure; rather, the citric acid, citrate, etc., acts a bacteriostatic solution to avoid bacterial growth between treatments and extend the use of cassette 42, associated lines and heater/mixing bag 62. It should also be appreciated that if traces of the citric acid or citrate remain in semi-disposable set 40 even after rinsing, the minor amount will not harm the patient considering that human beings commonly and safely metabolize citric acid and citrate for example.

Hot Water Disinfection

In an alternative multiple use of disposable set 40 embodiment, which may be used with any of systems 10a to 10d and any of their alternative embodiments described herein, the anti-growth inhibiting agent just described is replaced by or enhanced using hot water disinfection. Heaters 184a and 184b of water purifier 110 (FIG. 16), under control of control unit 112, heat its water to 70° C. for example to heat disinfect water purifier 110. This is done on a regular, e.g., daily or between treatment, basis to disinfect semi-disposable set 40.

In an embodiment, control unit 22 of cycler 20 is programmed to cause cycler to perform the waffling sequences described above to push and pull the heated water (possibly including an agent configure to inhibit microbiological growth) repeatedly throughout cassette 42 and heater/mixing bag 62, and repeatedly through water line segments 64a and 64b. The hot water is also cycled through drain line 56 and patient line 50, e.g., up to a hydrophobic membrane located in patient line connector 52. When the hot water disinfection of semi-disposable set 40 is completed, the hot water is sent to drain 116 at water purifier 110. Again, the hot water disinfection of semi-disposable set 40 may be performed with or without the growth inhibiting agent described above.

Alternative to Pneumatic Pumping

Each of systems 10a to 10d is illustrated above using pneumatic pumping. In an alternative embodiment, cycler may use one or more peristaltic pump instead. Peristaltic pumping alone may not be accurate enough to mix WFPD and the concentrates to produce a mixed dialysis fluid properly. It is accordingly contemplated to add a balance chamber type structure downstream from each peristaltic pump to greatly improve accuracy. The balance chamber includes an internal membrane or sheet that flexes back and forth due to fluid pressure. The tube from each peristaltic pump splits into two tube segments, one to each of first and second inlets to the balance chamber located on either side of the membrane or sheet. Two corresponding outlet tube segments are connected to first and second outlets of the balance chamber located on either side of the membrane or sheet.

Each of the four tube segments is positioned in a cycler in operable connection to a separate pinch valve. The pinch valves are sequenced alternatingly and repeatedly to allow WFPD or a concentrate from the peristaltic pump to flow alternatingly to either side of the membrane or sheet of the balance chamber, each time expelling a like volume of WFPD or concentrate out of the balance chamber from the other side of the membrane or sheet. Knowing the volume of each balance chamber stroke and counting strokes results in an accurate amount of WFPD and one or more concentrate being delivered to a heater/mixing chamber.

It is contemplated to provide three peristaltic pumps, including (i) a peristaltic WFPD and concentrate pump for pushing WFPD and concentrate to heater/mixing bag 62, (ii) a peristaltic mixed dialysis fluid pump for pushing mixed dialysis fluid from heater/mixing bag 62 to patient P, and (iii) a peristaltic used dialysis fluid pump for pushing used dialysis fluid from patient P to drain 116. Each of the three pumps operates with a corresponding downstream balance chamber as described to provide accurate mixing, accurate fresh dialysis fluid delivery to patient P, and accurate used dialysis fluid removal from patient P, resulting in accurate UF.

The mixing regimes (including waffling using the peristaltic pump between heater/mixing bag 62 and patient P) and dialysis fluid testing using conductivity sensing as described above for the pneumatic systems are equally applicable to the alternative peristaltic pump version of the point of use dialysis system. Concentrate connectors 80a/80b and 82a/82b illustrated and described above in connection with FIGS. 3A to 3D may be used with the peristaltic pump system. Heater/mixing bag connector 100 illustrated and described above in connection with FIGS. 4A to 4G may also be used with the peristaltic pump system.

Cycler/Water Purifier Communication

As discussed above at method 210 of FIG. 5, block 222 describes that cycler 20 pairs or syncs with water purifier 110. Once wirelessly paired, cycler 20 may order WFPD as needed from water purifier 110. As discussed above, cycler 20 may specify a quantity and temperature for the WFPD. Additionally, cycler 20 may specify a maximum WFPD supply pressure. If needed, cycler 20 may also tell water purifier 110 to abort the previously ordered delivery, e.g., if cycler 20 has experienced an alarm that is currently being addressed or if patient P has ended treatment for whatever reason.

As discussed above, to verify that dialysis fluid has been mixed properly, a sample or slug may be delivered via drain line 56 to a conductivity sensor 132 located at water purifier 110. In an embodiment, after the sample or slug is delivered to water purifier 110, cycler 20 requests from water purifier 110 that conductivity reading(s) from conductivity sensor 132 be sent to cycler 20. Water purifier 110 sends the conductivity reading(s) to cycler in response. In another embodiment, after the sample or slug is delivered to water purifier 110, cycler 20 puts itself into a wait mode and looks for the conductivity reading(s) from water purifier 110, which are sent automatically to cycler 20. Here, if the wait mode times out with no conductivity reading(s) having been delivered to cycler 20, the cycler may then request that the conductivity reading(s) be delivered.

As discussed above, in one reuse embodiment heated water is delivered from water purifier 110 to disposable set 40 operated by cycler 20 for disinfection. In one embodiment, water purifier 110 will not deliver the heated water to disposable set 40 until receiving a "ready for hot water disinfection" notice from cycler 20. For example, cycler 20 may want to confirm that patient P is disconnected from patient line 50, e.g., via a pressure check and/or manual confirmation via user interface 30 by patient P, before sending the "ready for hot water disinfection" notice to water purifier 110. In another example, cycler 20 may want to confirm that all fluids, e.g., residual fresh dialysis fluid, used dialysis fluid, concentrates, and/or WFPD have been delivered to drain 116 before sending the "ready for hot water disinfection notice" to water purifier 110.

Conductivity Estimating Algorithms

As discussed above, after the PD fluid is prepared by the cycler 20, a sample of the fluid (e.g., a slug of freshly mixed dialysis fluid) is pushed from the cycler 20 to and past conductivity sensor 132 in the water purifier 110. To reduce the amount of waste, the PD fluid sample (e.g., slug) is preferably pushed to the conductivity sensor 132 using pure water. For example, the PD fluid slug may be pushed through a drain line 56 that is as long as 10 to 20 meters, which may requires approximately 125 to 250 mL of fluid to push the slug past the conductivity sensor 132. Also, the PD fluid slug is preferably preceded by pure water from water purifier 110 to ensure that the prepared PD fluid slug is only mixing with pure RO water when passing the conductivity sensor 132. By preceding the PD fluid slug with RO water, the RO water may advantageously flush any residual waste fluid that may be in the drain line 56, thereby preventing the waste fluid from distorting the conductivity measurement at the conductivity sensor 132. The slug may be preceded by a predetermined volume of WFPD to sufficient to ensure that the slug does not mix with waste fluid at the head of the sample. As described above, the water purifier 110 may pump WFPD down the water line 64 and into the drain line 56 to fully prime the drain line 56. Then, the cycler 20 may pump a slug of prepared PD fluid from the heater/mixing bag 62 into the drain line 56. After a sufficient slug volume has been pumped, the water purifier 110 may then pump enough WFPD to the drain line to ensure that an amount sufficient to reach and pass the conductivity pulse maximum is pumped through the conductivity sensor 132.

Due to the water preceding the slug of freshly mixed dialysis fluid, some of the slug (e.g., leading edge or head of the slug) is mixed with the water preceding it, and therefore, a sufficient amount of sample fluid (e.g., slug) is pushed to the conductivity sensor 132 to ensure the conductivity reading of the slug reflects the conductivity of the mixed PD fluid. Depending on the amount of the sample sent to the conductivity sensor 132, the conductivity signal may or may not reach an asymptotic value 402. For example, smaller samples are less likely to generate a conductivity signal that reach an asymptotic value 402.

Figure 18:
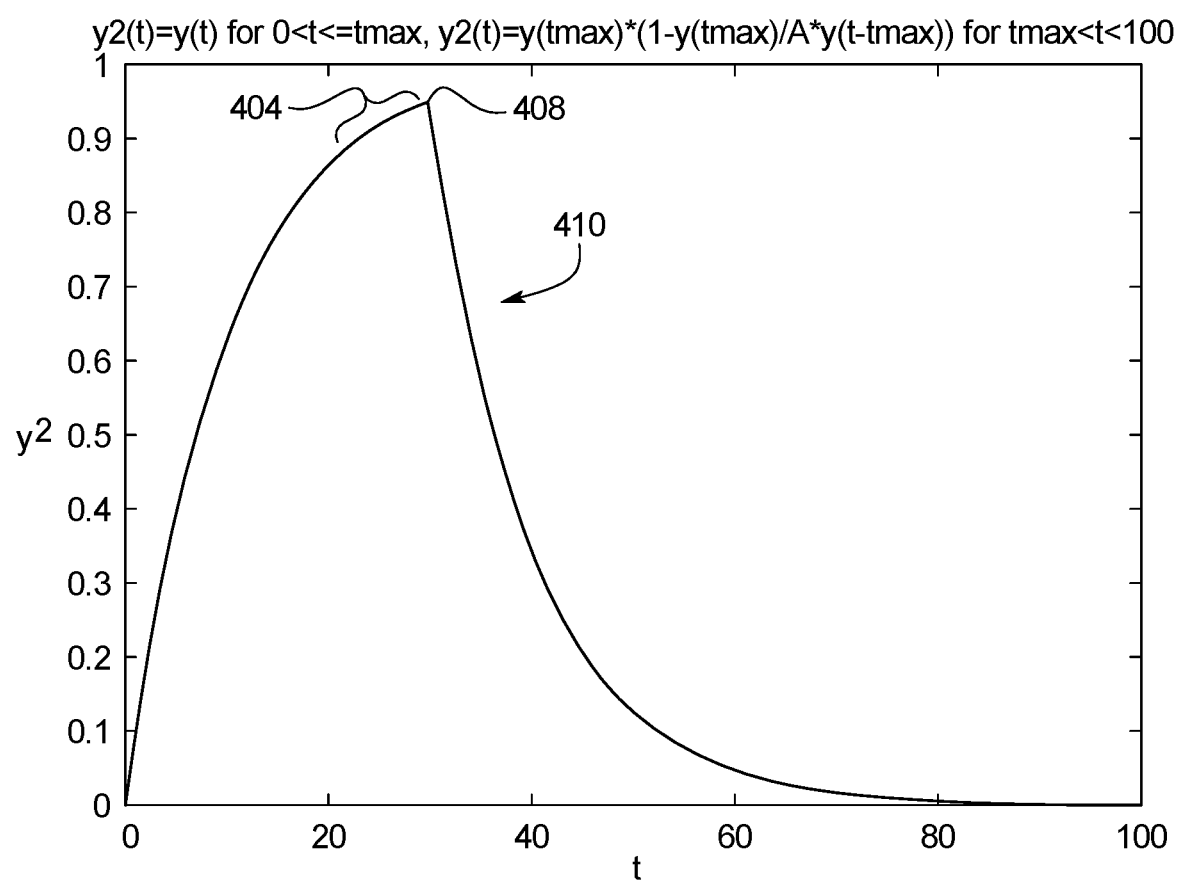

In an example, conductivity measurements, or other measurements to ensure the prepared PD fluid is mixed properly, may be made using data from the end of the slug pulse (a slug pulse 410 is illustrated in FIG. 18). For example, conductivity measurements 404 may use the last few seconds of the top of the conductivity pulse 410 to ensure that readings closest to the asymptotic conductivity value 402 are used. However, conductivity readings are sensitive to air (e.g., air bubbles), which may result in a sudden spike (e.g., dip) in the conductivity reading, thereby leading to improper readings such as false positives. Inaccurate readings may require additional measurements or discarding otherwise good fluid, which wastes time and concentrate.

By applying the conductivity function as discussed below, much more conductivity data is used and air bubbles will have less of an effect on the measurement, thereby advantageously minimizing false positives. Additionally, as further discussed below, using the difference between the unknown asymptotic value 402 and the measurement and by taking the natural logarithm value of the difference further reduces the effect of air bubbles on the conductivity measurement and asymptote estimate. Moreover, by using the least mean square fit, the "swing" or spikes in data due to air bubbles will be further reduced, thereby further reducing the likelihood of a false positive.

Measured conductivity data may be manipulated to predict the asymptotic value without actually reaching the asymptotic value of the conductivity signal from the sample fluid, thereby advantageously minimizing the amount of PD fluid used to determine the conductivity of the prepared PD fluid and thus reducing waste of PD concentrates. In an example embodiment, predicting conductivity may result in a 25% reduction in the amount of prepared PD fluid used for a conductivity reading. For example, by predicting conductivity, a smaller sample (e.g., 60 to 70 milliliters) may be used. Conversely, without predicting conductivity, a larger sample (e.g., 80 to 100 milliliters) may be required for the conductivity signal to reach an asymptotic value 402. For example, a large enough sample of prepared PD fluid ensures that the conductivity signal reaches an asymptotic value 402 for a sufficient period of time, thereby ensuring that the reading is based on a series of readings at or near the asymptotic value 402, which may minimize the risk that possible air bubbles within the line compromise the result. Additionally, conductivity data may be manipulated to enhance the conductivity readings or larger PD fluid samples. In other examples, the inside diameter of a drain tube 56 may be decreased to reduce the volume needed to test the conductivity of the sample fluid.

Figure 17:
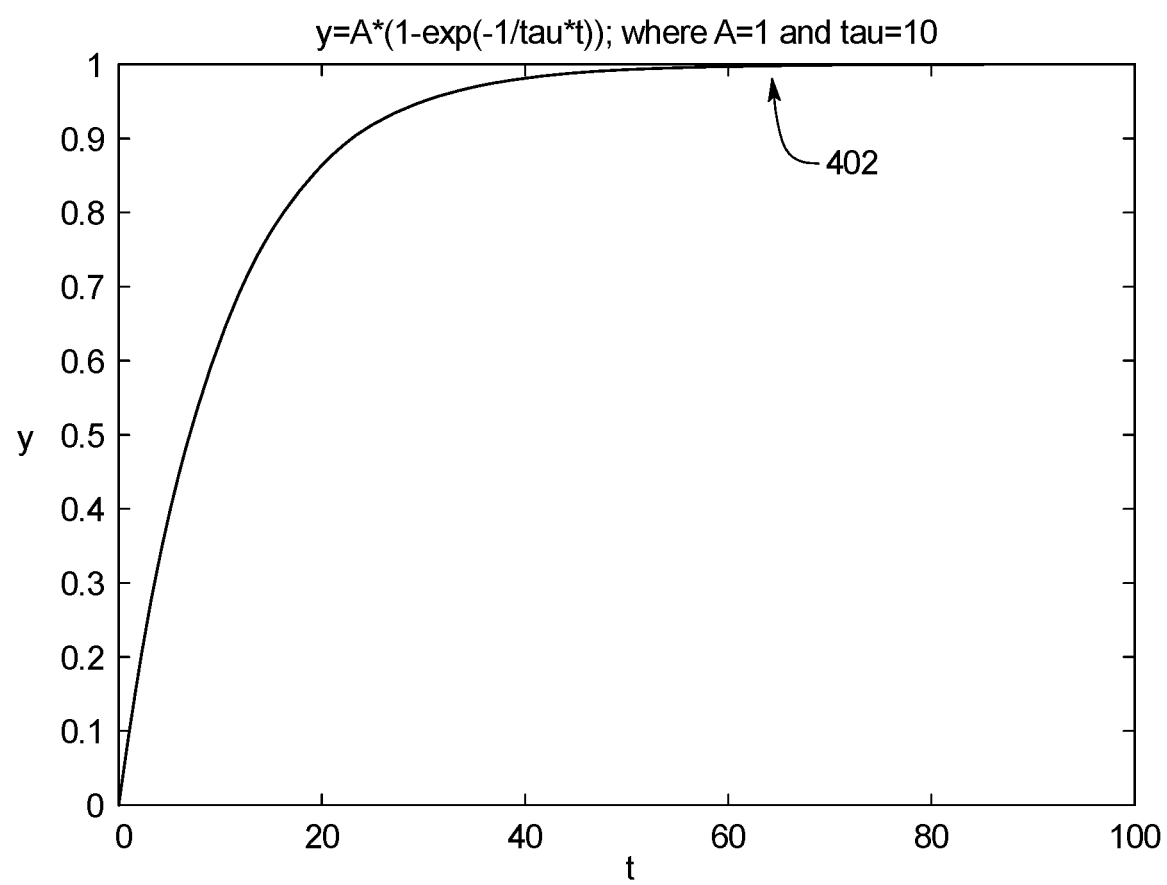
FIGS. 17 to 19 illustrate various plots associated with one embodiment of an estimating algorithm of the present disclosure, which may be used with any of the peritoneal dialysis systems having point of use dialysis fluid production discussed herein, wherein the estimating algorithm enables the amount of mixed dialysis fluid needed to obtain a suitable conductivity reading to be lessened.

If there is enough sample fluid such that the conductivity signal stabilizes, a conductivity signal may represent a function similar to (A-1) below, and as illustrated in FIG. 17, where A is the asymptotic value 402 and τ is the time constant:

$$y(t) = A \cdot \left(1 - e^{-\frac{1}{\tau} \cdot t}\right) \quad (A\text{-}1)$$

However, if the sample is smaller and does not fully stabilize, the signal may represent the signal illustrated in FIG. 18. By subtracting the function y(t) in (A-1) from the asymptotic value A and further taking the natural logarithm of the difference gives:

$$\ln(A - y(t)) = \quad (A\text{-}2)$$
$$\ln\left(A - A \cdot \left(1 - e^{-\frac{1}{\tau} \cdot t}\right)\right) = \ln(A) - \frac{1}{\tau} \cdot t \cdot \ln(e) = \ln(A) - \frac{1}{\tau} \cdot t$$

Thus, (A-2) is a linear expression with a slope represented by $-1/\tau$. Even though the asymptotic value A is unknown, a value can be guessed (called $A_g$) based on the visual representation of the pulse 410 or from other information. For example, the guess may be what the expected conductivity value is (e.g., from a look-up table). By using the guess, the resulting expression becomes:

$$\ln(A_g - y(t)) = \ln\left(A_g - A \cdot \left(1 - e^{-\frac{1}{\tau} \cdot t}\right)\right) = \ln\left((A_g - A) + A \cdot e^{-\frac{1}{\tau} \cdot t}\right) \quad (A\text{-}3)$$

Figure 19:
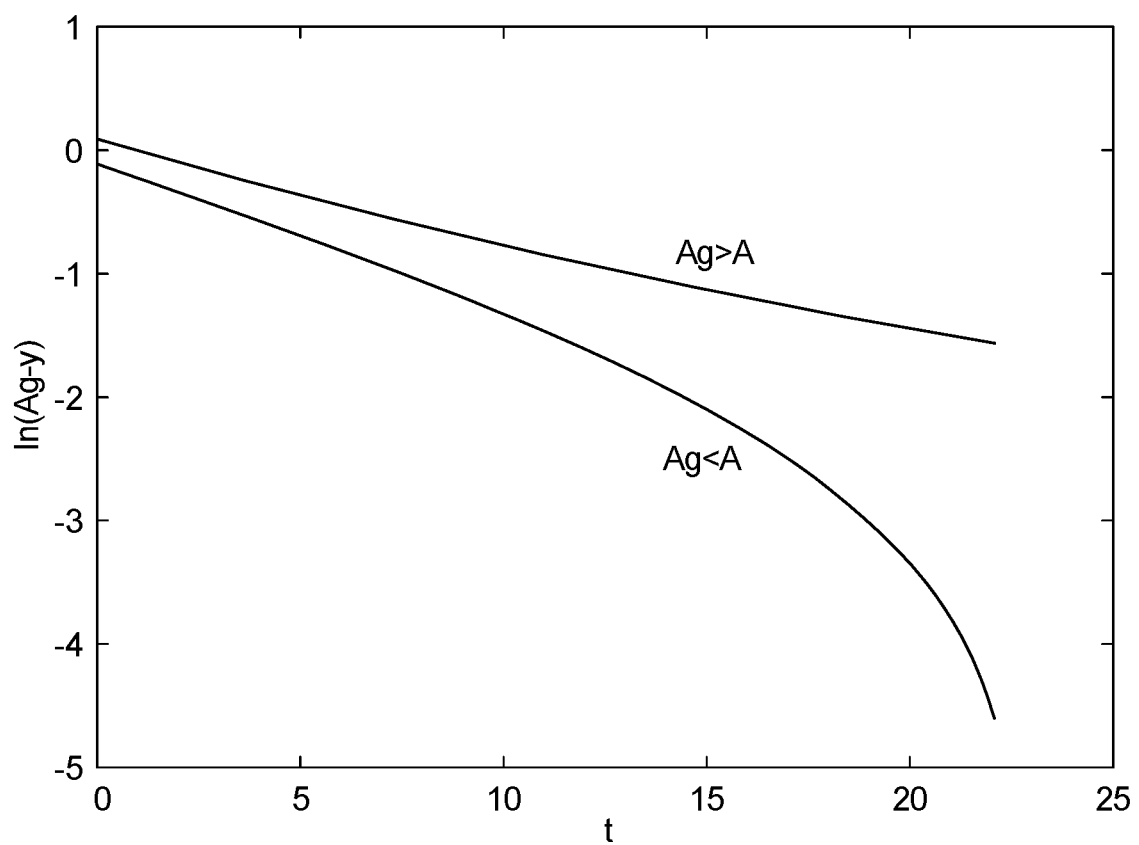

When $A_g = A$, the resulting expression in (A-3) will become linear. However, when the guess for $A_g$ does not equal A, and thus does not equal the true asymptotic value 402, the resulting expression of (A-3) is no longer linear. For example, plotted values where guesses for $A_g$ are greater than or less than the asymptotic value are represented in FIG. 19.

In order to estimate the asymptotic value 402, several guesses may be used to determine which guessed asymptotic value gives a straight, or the straightest line. Once a guess value ($A_g$) is selected, the measured conductivity data is subtracted from the guess value ($A_g$) and the natural logarithm of the difference is calculated. Then, to determine how "straight" the obtained result is when plotted against time, a least mean square fit to the data may be conducted. An absolute difference between the least mean square line and the test function may be created and the sum of the absolute differences may be calculated. The guess value ($A_g$) that results in the lowest sum value is the straightest line, and thus the best predicted conductivity value (e.g., the predicted asymptotic value that most closely represents the asymptotic value had more sample fluid been pushed past the conductivity sensor 132).

Guesses may be chosen using several different techniques. Additionally, guesses may be based on conductivity data that is measured from the slug (e.g., conductivity measurements 404) or based on expected conductivity data (e.g., from a look-up table). In one embodiment, an initial guess ($A_g$) may be selected from what the expected conductivity is. Then, subsequent guesses may alternate on opposite sides of the initial guess, until the sum value from the least mean square fit produces a larger number on both sides of the initial guess (e.g., thereby indicating that the guess is worse than the previous guess), which gives one or more different intervals or "valleys" where the best guess fits. For example, if the expected conductivity is 11.64 mS/cm, the initial guess ($A_g = 11.64$) may be used and the sum value from the least mean square fit may be calculated. Then, guesses on opposite sides of the initial guess (e.g., $A_g > 11.64$ and $A_g < 11.64$) may be used until the sum value from the least mean square fit stops producing smaller sums. For example, guesses of 11.65, 11.63, 11.66, 11.62, 11.67, etc. may be used until a minimum value of the sum from the least mean square fit is determined. For example, the smallest sum from the initial guesses may be 11.67 where guesses using $A_g = 11.66$ and $A_g = 11.68$ both produced larger sums. Then, the asymptotic value is somewhere between 11.66 and 11.68, and as discussed in more detail below, guesses may be refined within that range using smaller step sizes.

Guesses may be made using various predetermined increments. For example, each iterative guess may be stepped by 0.1, 0.01, 0.001, etc. In other examples, larger increments may be used until the two or three best guesses have been determined. Then, smaller incremental guesses may be used between those guesses. For example, if incremental guesses of 11.66, 11.67, and 11.68 (e.g., using 0.01 as a step) produce the three lowest sums from the least mean square fit described above, then guesses between 11.66 and 11.68 may be used to refine the guess using a step of 0.001, which may advantageously cut down on processing time by reducing the amount of calculations by control unit 112 of water purifier 110. For example, if the control unit 112 runs all calculations using an initial of step size of 0.001, then many more iterations may be required before estimating the best asymptotic value.

In another example, the maximum value 408 of the measured pulse may be used as a starting point for the initial guess. For example, if the maximum value 408 of the pulse is measured as 11.612 mS/cm, 11.612 may be used as an initial guess. As mentioned above, to avoid imaginary numbers, an initial guess above the maximum value may be used. For example, a range of guesses may be used between a lower end guess (e.g., maximum measured conductivity value) and an upper end guess (e.g., expected value of conductivity plus a safety factor) that takes into account that the fluid may be mixed incorrectly. For example, if the expected conductivity value is 11.64 mS/cm, upper and lower end guesses may be:

$$11.612 + 0.001 < A_g < 11.612 + 2 \cdot (11.64 - (11.612 + 0.001))$$

Then, guesses may be stepped from the lower end guess of 11.613 to the higher end guess of 12.613 in a predetermined step interval, such as 0.001. After the sum of the absolute difference of the curve to their respective least mean square fit, the lowest sum of the absolute difference results in the estimate asymptotic value of the conductivity.

Temperature Estimating Algorithm

Similar to the conductivity measurement, the temperature of the fluid sample may also be estimated. Conductivity is dependent on temperature and the conductivity reading may need to be temperature compensated to be comparable to other conductivity readings. For example, conductivity readings may be normalized to 25° C. such that multiple readings may be accurately compared to each other and also compared to appropriate values in a look-up table.

Temperature at conductivity sensor 132a used for measuring the prepared PD fluid may not be constant. For example, water sent from the accumulator bag 66 to the drain and prepared PD fluid may have different temperatures, such as 18° C. to 25° C. and 37° C. respectively. The water from the accumulator bag 66 may be affected by the room temperature and/or environment where the system is positioned.

Figure 20:
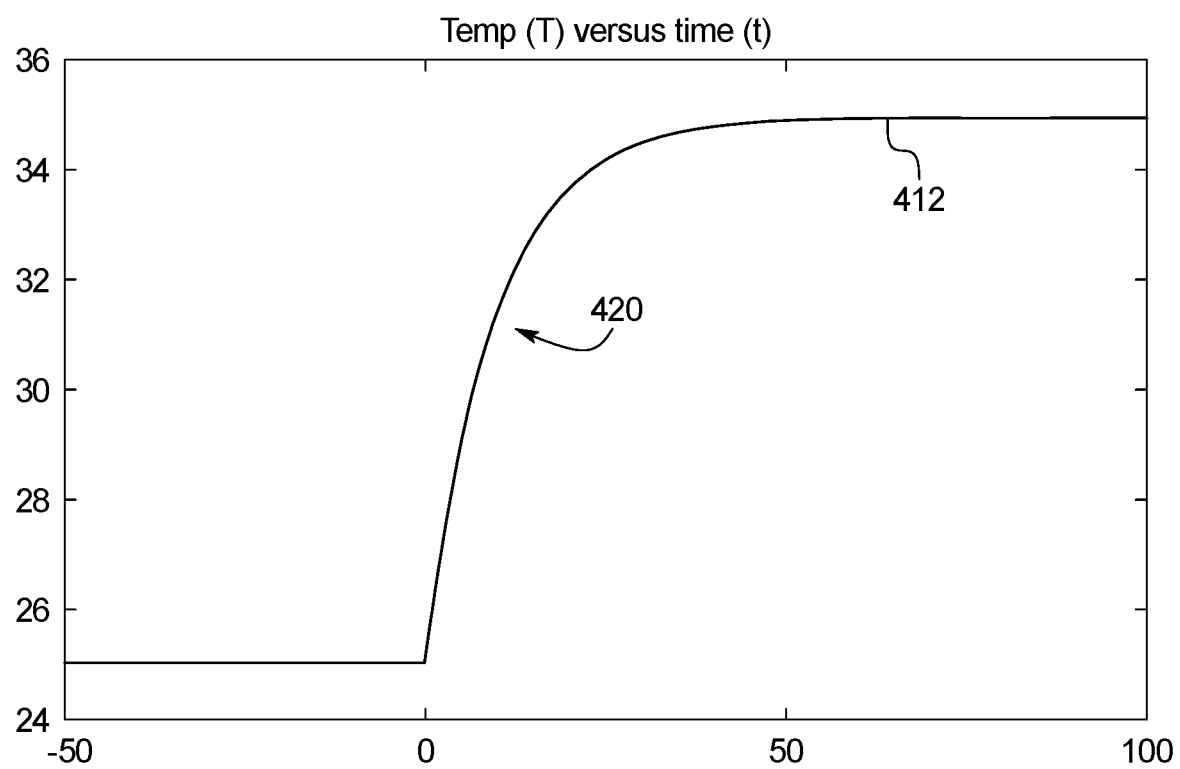
FIG. 20 illustrates a plot associated with another embodiment of an estimating algorithm of the present disclosure, here showing tested, e.g., dialysis, fluid temperature over time, and which may be used with any of the peritoneal dialysis systems having point of use dialysis fluid production discussed herein, wherein the estimating algorithm enables the amount of mixed dialysis fluid needed to obtain a suitable conductivity reading to be lessened.

Similar techniques as discussed above with reference to conductivity may be used to estimate the asymptotic value 412 of the temperature for the fluid sample of the prepared PD fluid. A temperature pulse 420, illustrated in FIG. 20, represents temperature measurements in which water from an accumulator bag 66 is followed by a sufficiently large amount of the prepared PD fluid, such that the temperature reaches an asymptotic value 412.

The temperature pulse 420 may be described by the following function:

$$T(t) = T_0 + (T_A - T_0) \cdot \left(1 - e^{-\frac{1}{\tau} \cdot t}\right) \quad \text{(B-1)}$$

In expression (B-1), $T_0$ is the initial temperature, $T_A$ is the asymptotic temperature, and $\tau$ is the time constant. By subtracting the function T(t) in (B-1) from the asymptotic value $T_A$ gives:

$$T_A - T(t) = T_A - \left(T_0 + (T_A - T_0) \cdot \left(1 - e^{-\frac{1}{\tau} \cdot t}\right)\right) = (T_A - T_0) \cdot e^{-\frac{1}{\tau} \cdot t} \quad \text{(B-2)}$$

Taking the natural logarithm of the difference in (B-2) gives:

$$\ln(T_A - T(t)) = \ln(T_A - T_0) - \frac{1}{\tau} \cdot t \quad \text{(B-3)}$$

The resulting expression (B-3) is linear expression with a slope represented by $-1/\tau$. Similar to the techniques discussed above with respect to the conductivity value, the temperature value $T_A$ may be estimated by using several different guess temperature values until the lowest sum value of the least mean squares line is obtained.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A peritoneal dialysis system comprising:
   a cycler including a pump actuator, a heater and a heating pan operable with the heater, wherein the heating pan includes a sidewall forming a slot; and
   a disposable set operable with the cycler, the disposable set including
      a pumping cassette including a pump chamber configured to be actuated by the pump actuator, and
      a heater/mixing container in fluid communication with the pumping cassette and sized to be received at the heating pan, the heater/mixing container including a port configured such that when the port is slid into the slot of the heater pan sidewall, the port is prevented from rotating about an axis transverse to a direction of flow through the port, wherein the slot includes an angled section through which a portion of the port is inserted and a circular section for receiving the portion of the port, and wherein a transition from the angled section to the circular section is sized so that the portion of the port press-fits through the transition to provide tactile feedback.

2. The peritoneal dialysis system of claim 1, wherein the port includes first and second flanges which abut first and second sides of the sidewall when the port is slid into the slot to prevent the port from rotating about an axis transverse to the direction of flow through the port.

3. The peritoneal dialysis system of claim 1, wherein the port includes a member that abuts first and second sides of the slot when the port is slid into the slot to prevent the port from rotating about an axis inline with the direction of flow through the port.

4. The peritoneal dialysis system of claim 3, wherein the member is positioned and arranged to prevent the heater/mixing container from being loaded upside down onto the heating pan.

5. A peritoneal dialysis system comprising:
   a cycler having a heating pan that includes a sidewall forming a slot;
   a disposable set operable with the cycler; and a heater/mixing container sized to be received at the heating pan, the heater/mixing container including a port configured such that when the port is slid into the slot of the heater pan sidewall, the port is prevented from rotating about an axis transverse to a direction of flow through the port, wherein the slot includes an angled section through which a portion of the port is inserted and a circular section for receiving the portion of the port, and wherein a transition from the angled section to the circular section is sized so that the portion of the port press-fits through the transition to provide tactile feedback.

6. The peritoneal dialysis system of claim 5, wherein the port includes first and second flanges which abut first and second sides of the sidewall when the port is slid into the slot to prevent the port from rotating about an axis transverse to the direction of flow through the port.

7. The peritoneal dialysis system of claim 5, wherein the port includes a member that abuts first and second sides of the slot when the port is slid into the slot to prevent the port from rotating about an axis inline with the direction of flow through the port.

8. The peritoneal dialysis system of claim 7, wherein the member is positioned and arranged to prevent the heater/mixing container from being loaded upside down onto the heating pan.

\* \* \* \* \*